(12) United States Patent
Knight

(10) Patent No.: US 12,257,358 B2
(45) Date of Patent: *Mar. 25, 2025

(54) DISINFECTION SYSTEMS AND METHODS

(71) Applicant: SOCLEAN, INC., Peterborough, NH (US)

(72) Inventor: James Knight, Bedford, NH (US)

(73) Assignee: SOCLEAN, INC., Peterborough, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/780,026

(22) Filed: Jul. 22, 2024

(65) Prior Publication Data

US 2024/0374772 A1 Nov. 14, 2024

Related U.S. Application Data

(63) Continuation of application No. 18/368,598, filed on Sep. 15, 2023, now Pat. No. 12,064,527.

(60) Provisional application No. 63/458,578, filed on Apr. 11, 2023, provisional application No. 63/458,527, filed on Apr. 11, 2023, provisional application No. 63/375,992, filed on Sep. 16, 2022.

(51) Int. Cl.
*A61L 2/20* (2006.01)

(52) U.S. Cl.
CPC ........... *A61L 2/202* (2013.01); *A61L 2202/11* (2013.01); *A61L 2202/15* (2013.01); *A61L 2202/24* (2013.01)

(58) Field of Classification Search
CPC ...................................................... A61L 2/202
See application file for complete search history.

(56) References Cited

U.S. PATENT DOCUMENTS

| | | | |
|---|---|---|---|
| 4,019,986 | A | 4/1977 | Burris |
| 4,035,657 | A | 7/1977 | Carlson |
| 4,110,419 | A | 8/1978 | Miller |
| 4,207,291 | A | 6/1980 | Byrd |
| 4,465,522 | A | 8/1984 | Taldo |
| 4,517,159 | A | 5/1985 | Karlson |
| D295,074 | S | 4/1988 | Jerge |
| 4,743,275 | A | 5/1988 | Flanagan |

(Continued)

FOREIGN PATENT DOCUMENTS

| | | |
|---|---|---|
| CN | 1377708 | 11/2002 |
| CN | 2659447 Y | 12/2004 |

(Continued)

OTHER PUBLICATIONS

English Translation of International Document No. WO 2021/228682 A1 provided by the European Patent Website espacenet.com: Kromker, Wilfried; Disinfection Device; Nov. 18, 2021 (Year: 2021).*

(Continued)

*Primary Examiner* — Kevin Joyner
(74) *Attorney, Agent, or Firm* — Grossman, Tucker, Perreault & Pfleger, PLLC

(57) ABSTRACT

A disinfection device may include a disinfection chamber, an ozone generator configured to generate ozone, and a humidifier configured to generate humidity and configured to be fluidly coupled to the disinfection chamber and the ozone generator, the humidifier being configured to encourage a mixing of generated ozone with generated humidity.

30 Claims, 45 Drawing Sheets

(56) References Cited

U.S. PATENT DOCUMENTS

| | | |
|---|---|---|
| 4,787,980 A | 11/1988 | Ackermann |
| 5,029,879 A | 7/1991 | Strang |
| 5,120,512 A | 6/1992 | Masuda |
| 5,207,237 A | 5/1993 | Langford |
| 5,344,622 A | 9/1994 | Faddis |
| 5,508,006 A | 4/1996 | Gabele |
| 5,520,893 A | 5/1996 | Kasting |
| D371,203 S | 6/1996 | Deeds |
| D390,645 S | 2/1998 | Hanrahan |
| 5,761,069 A | 6/1998 | Webber |
| 5,920,075 A | 7/1999 | Whitehead |
| 6,024,066 A | 2/2000 | Nakayama |
| 6,092,794 A | 7/2000 | Reens |
| 6,134,806 A | 10/2000 | Dhaemers |
| 6,158,784 A | 12/2000 | Lavender |
| 6,276,304 B1 | 8/2001 | Tai |
| 6,280,633 B1 | 8/2001 | Conrad |
| 6,365,601 B1 | 4/2002 | Fournier |
| 6,379,617 B1 | 4/2002 | Spickermann |
| 6,379,632 B1 | 4/2002 | Kinoshita |
| D476,423 S | 6/2003 | Picot |
| 6,576,190 B1 | 6/2003 | Park |
| 6,605,260 B1 | 8/2003 | Busted |
| D487,315 S | 3/2004 | Picot |
| 6,752,151 B2 | 6/2004 | Hill |
| 7,022,225 B1 | 4/2006 | Clawson |
| 7,491,321 B1 | 2/2009 | Maas et al. |
| 7,520,910 B2 | 4/2009 | Tilley |
| 7,527,603 B2 | 5/2009 | An |
| 7,608,217 B2 | 10/2009 | Champagne |
| 7,676,276 B2 | 3/2010 | Karell |
| 7,767,168 B2 | 8/2010 | Namespetra |
| 7,794,522 B2 | 9/2010 | Bliss |
| 7,845,350 B1 | 12/2010 | Kayyali |
| 8,051,853 B2 | 11/2011 | Berthon-Jones |
| 8,146,946 B1 | 4/2012 | Emond |
| 8,176,771 B2 | 5/2012 | Onishi |
| 8,215,465 B2 | 7/2012 | Iceberg |
| 8,431,075 B2 | 4/2013 | Fraundorfer |
| D692,155 S | 10/2013 | Matoba |
| 8,677,842 B2 | 3/2014 | Devine |
| 8,770,198 B2 | 7/2014 | Yee |
| 8,815,164 B1 | 8/2014 | Al Azemi |
| D719,673 S | 12/2014 | Leyva |
| D719,674 S | 12/2014 | Leyva |
| 8,915,380 B2 | 12/2014 | Sowerby |
| 9,022,247 B2 | 5/2015 | Enigmann |
| D733,315 S | 6/2015 | Lui |
| D733,316 S | 6/2015 | Lui |
| D748,280 S | 1/2016 | Lui |
| 9,358,311 B2 | 6/2016 | Leyva |
| D761,142 S | 7/2016 | Golta |
| 9,402,928 B2 | 8/2016 | Tremblay |
| 9,452,274 B2 | 9/2016 | Addington et al. |
| D776,290 S | 1/2017 | Wan |
| 9,610,373 B2 | 4/2017 | Leyva |
| 9,616,147 B2 | 4/2017 | Leyva |
| 9,669,124 B2 | 6/2017 | Leyva |
| D802,788 S | 11/2017 | Cormier |
| 9,814,795 B2 | 11/2017 | Dufresne et al. |
| 9,895,461 B2 | 2/2018 | Leyva |
| 9,907,872 B2 | 3/2018 | Schmidt |
| D819,190 S | 5/2018 | Cormier |
| 9,956,309 B1 | 5/2018 | Leyva |
| 10,052,397 B2 | 8/2018 | Leyva |
| 10,232,072 B2 | 3/2019 | Leyva |
| 10,264,913 B2 | 4/2019 | Leyva |
| 10,293,125 B2 | 5/2019 | Jeha et al. |
| 10,398,797 B2 | 9/2019 | Leyva |
| 10,427,961 B2 | 10/2019 | Leyva |
| 10,434,204 B2 | 10/2019 | Leyva |
| 10,434,205 B2 | 10/2019 | Leyva |
| 10,456,492 B2 | 10/2019 | Leyva |
| 10,485,888 B2 | 11/2019 | Schmidt |
| 10,842,897 B2 | 11/2020 | Schwartz |
| 10,980,905 B2 | 4/2021 | Bohman |
| 11,000,611 B1 | 5/2021 | He |
| 11,484,613 B2 | 11/2022 | Maw et al. |
| 2002/0139124 A1 | 10/2002 | Palermo |
| 2003/0000966 A1 | 1/2003 | Shelton |
| 2003/0063997 A1 | 4/2003 | Fryer |
| 2003/0065292 A1 | 4/2003 | Darouiche |
| 2003/0065297 A1 | 4/2003 | Davis |
| 2003/0071069 A1 | 4/2003 | Shelton |
| 2004/0007000 A1 | 1/2004 | Takeda |
| 2004/0028583 A1 | 2/2004 | Hedman |
| 2004/0202570 A1 | 10/2004 | Nadkarni |
| 2004/0251125 A1 | 12/2004 | Yu |
| 2005/0017380 A1 | 1/2005 | Namespetra |
| 2005/0019237 A1 | 1/2005 | Riley |
| 2005/0168907 A1 | 8/2005 | Sekoguchi |
| 2005/0186108 A1 | 8/2005 | Fields |
| 2005/0191219 A1 | 9/2005 | Uslenghi et al. |
| 2005/0220665 A1 | 10/2005 | Ding |
| 2006/0034737 A1 | 2/2006 | Beam et al. |
| 2006/0130834 A1 | 6/2006 | Chen |
| 2006/0272682 A1 | 12/2006 | Langford |
| 2007/0031778 A1 | 2/2007 | Helfenbein |
| 2007/0065335 A1 | 3/2007 | Bedard |
| 2007/0110611 A1 | 5/2007 | Teran et al. |
| 2008/0050290 A1 | 2/2008 | Yui |
| 2008/0118411 A1 | 5/2008 | D'Arinzo |
| 2009/0004047 A1 | 1/2009 | Hunter et al. |
| 2009/0080809 A1 | 3/2009 | Pham |
| 2009/0267242 A1 | 10/2009 | Nichols |
| 2010/0047116 A1 | 2/2010 | Garner |
| 2010/0059431 A1 | 3/2010 | Cho |
| 2010/0111792 A1 | 5/2010 | Nelson |
| 2010/0112677 A1 | 5/2010 | Onishi |
| 2010/0147302 A1 | 6/2010 | Selvarajan |
| 2011/0031081 A1 | 2/2011 | Iceberg |
| 2011/0226868 A1 | 9/2011 | Modlin et al. |
| 2012/0164025 A1 | 6/2012 | Stockley, III et al. |
| 2012/0189490 A1 | 7/2012 | Van Den Bossche et al. |
| 2012/0227745 A1 | 9/2012 | Arcilla |
| 2012/0230880 A1 | 9/2012 | Dunkley et al. |
| 2013/0177475 A1 | 7/2013 | Finch |
| 2013/0239994 A1 | 9/2013 | Przyjemski |
| 2014/0112837 A1 | 4/2014 | Huang |
| 2014/0154134 A1 | 6/2014 | Leyva |
| 2014/0193294 A1 | 7/2014 | Kain et al. |
| 2015/0004061 A1 | 1/2015 | Kain |
| 2015/0017059 A1* | 1/2015 | Arlemark ............... A61L 9/015 422/119 |
| 2016/0235875 A1 | 8/2016 | Schmidt |
| 2016/0235876 A1 | 8/2016 | Leyva et al. |
| 2016/0243268 A1 | 8/2016 | Leyva |
| 2017/0157278 A1 | 6/2017 | Schmidt et al. |
| 2017/0165443 A1 | 6/2017 | Leyva |
| 2017/0202990 A1 | 7/2017 | Leyva |
| 2017/0209610 A1 | 7/2017 | Leyva |
| 2017/0224857 A1 | 8/2017 | Leyva |
| 2017/0225985 A1 | 8/2017 | Leyva |
| 2017/0370013 A1 | 12/2017 | Bahar |
| 2018/0028770 A1 | 2/2018 | Parrish |
| 2018/0161466 A1 | 6/2018 | Schmidt |
| 2018/0169283 A1 | 6/2018 | Stratman et al. |
| 2018/0207307 A1 | 7/2018 | Schwartz |
| 2018/0250431 A1 | 9/2018 | Eide et al. |
| 2018/0264157 A1 | 9/2018 | Benedek |
| 2018/0311391 A1 | 11/2018 | Leyva |
| 2018/0311595 A1 | 11/2018 | Leyva |
| 2019/0076561 A1 | 3/2019 | Leyva |
| 2019/0076562 A1 | 3/2019 | Schmidt |
| 2019/0083668 A1 | 3/2019 | Schmidt |
| 2019/0151487 A1 | 5/2019 | Leyva |
| 2019/0167828 A1 | 6/2019 | Leyva |
| 2019/0336627 A1 | 11/2019 | Lucio |
| 2019/0388575 A1 | 12/2019 | Leyva et al. |
| 2020/0000950 A1 | 1/2020 | Bohman |
| 2020/0024167 A1 | 1/2020 | Leyva et al. |
| 2020/0069362 A1 | 3/2020 | Paesch |
| 2021/0023250 A1 | 1/2021 | Golkowski et al. |

(56) References Cited

U.S. PATENT DOCUMENTS

| | | | |
|---|---|---|---|
| 2021/0196850 | A1 | 7/2021 | Maw et al. |
| 2023/0007917 | A1 | 1/2023 | Maw et al. |
| 2023/0320542 | A1 | 10/2023 | Asahi et al. |

FOREIGN PATENT DOCUMENTS

| | | | |
|---|---|---|---|
| CN | 2710637 | | 7/2005 |
| CN | 1951507 | | 4/2007 |
| CN | 2905066 | | 5/2007 |
| CN | 201156965 | | 12/2008 |
| CN | 102497916 | A | 6/2012 |
| CN | 103781498 | | 5/2014 |
| CN | 204261187 | U | 4/2015 |
| CN | 105031693 | | 11/2015 |
| CN | 107441598 | A | 12/2017 |
| CN | 108671253 | | 10/2018 |
| CN | 109069675 | A | 12/2018 |
| CN | 213910114 | U | 8/2021 |
| CN | 114796745 | A | 7/2022 |
| CN | 217138746 | U | 8/2022 |
| DE | 102020112847 | A1 | 11/2021 |
| EP | 2731632 | B1 | 8/2017 |
| EP | 2841208 | B1 | 2/2018 |
| ES | 2362426 | T3 | 7/2011 |
| ES | 2704136 | T3 | 3/2019 |
| JP | S62230601 | | 10/1987 |
| JP | H0724064 | | 1/1995 |
| JP | 2000288091 | | 10/2000 |
| JP | 2004148075 | A | 5/2004 |
| JP | 2005270589 | | 10/2005 |
| JP | 2009131354 | | 6/2009 |
| JP | 2012020207 | A | 2/2012 |
| JP | 2014523327 | | 1/2013 |
| JP | 5423813 | B2 | 2/2014 |
| JP | 6397764 | B2 | 9/2018 |
| KR | 20040098412 | | 11/2004 |
| KR | 101839063 | | 3/2018 |
| WO | 03068274 | | 8/2003 |
| WO | 2008116165 | | 9/2008 |
| WO | 2011058472 | | 5/2011 |
| WO | 2013012696 | | 1/2013 |
| WO | 2015171730 | | 11/2015 |
| WO | 2017189915 | | 11/2017 |
| WO | 2017189916 | | 11/2017 |
| WO | 2017189916 | A1 | 11/2017 |
| WO | 2018200525 | | 11/2018 |
| WO | 2020191194 | A1 | 9/2020 |
| WO | WO-2021228682 | A1 * | 11/2021 ............ A61B 90/80 |
| WO | 2022034395 | | 2/2022 |
| WO | 2022198222 | A1 | 9/2022 |

OTHER PUBLICATIONS

Preliminary Report on Patentability mailed Nov. 8, 2018, issued in PCT International Patent Application No. PCT/US2017/029949, 9 pages.

Preliminary Report on Patentability mailed Nov. 8, 2018, issued in PCT International Patent Application No. PCT/US2017/029950, 9 pages.

Office Action mailed Jan. 16, 2019, issued in Korean Patent Application No. 10-2018-7009274, 5 pages. English language translation provided.

Notice of Allowance mailed Jan. 18, 2019, issued in U.S. Appl. No. 15/441,929, 7 pages.

Office Action mailed Jan. 22, 2019, issued in U.S. Appl. No. 16/190,996, 10 pages.

Examination Report dated May 15, 2019, issued in Australian Patent Application No. 2017228723, 5 pages.

Notice of Allowance mailed May 17, 2019, issued in U.S. Appl. No. 16/270,141, 7 pages.

Notice of Allowance mailed May 22, 2019, issued in U.S. Appl. No. 15/499,456, 5 pages.

Notice of Allowance mailed May 28, 2019, issued in U.S. Appl. No. 15/499,378, 7 pages.

Notice of Allowance mailed Jun. 20, 2019, issued in U.S. Appl. No. 16/257,898, 8 pages.

U.S. Office Action mailed Jul. 26, 2019, issued in U.S. Appl. No. 16/190,996, 11 pages.

International Search Report and Written Opinion mailed Jul. 13, 2018, issued in PCT International Patent Application No. PCT/US18/29140, 11 pages.

Office Action mailed Aug. 9, 2018, issued in Japanese Patent Application No. 2014-520352, 4 pages.

Office Action mailed Sep. 5, 2018, issued in Chinese Patent Application No. 2016105175158, 10 pages.

Office Action mailed Sep. 17, 2018, issued in U.S. Appl. No. 15/441,929, 10 pages.

Examination Report mailed Sep. 26, 2018, issued in Australian Patent Application No. 2017228723, 6 pages.

U.S. Final Office Action mailed Feb. 4, 2018, issued in U.S. Appl. No. 15/141,152, 14 pages.

U.S. Office Action mailed Apr. 3, 2018, issued in U.S. Appl. No. 15/873,506, 7 pages.

U.S. Notice of Allowance mailed Apr. 27, 2018, issued in U.S. Appl. No. 15/142,085, 8 pages.

U.S. Office Action dated Jun. 13, 2017, issued in U.S. Appl. No. 15/481,919, 10 pages.

International Search Report and Written Opinion dated Aug. 2, 2017, issued in PCT Patent Application No. PCT/US17/29949, 11 pages.

U.S. Office Action dated Aug. 3, 2017, issued in U.S. Appl. No. 15/141,152, 14 pages.

International Search Report and Written Opinion dated Aug. 16, 2017, issued in PCT Patent Application No. PCT/US17/29950, 11 pages.

International Search Report and Written Opinion dated Sep. 17, 2012, issued in PCT Application No. PCT/US12/46593, 6 pages.

International Search Report and Written Opinion dated Jul. 24, 2015, issued in PCT Application No. PCT/US15/29418, 9 pages.

U.S. Office Action dated Jun. 30, 2016, issued in U.S. Appl. No. 15/141,216, 13 pages.

U.S. Office Action dated Jul. 13, 2016, issued in U.S. Appl. No. 15/142,060, 18 pages.

U.S. Office Action dated Jul. 14, 2016, issued in U.S. Appl. No. 15/142,111, 10 pages.

U.S. Office Action dated Jul. 28, 2016, issued in U.S. Appl. No. 15/142,085, 15 pages.

U.S. Office Action dated Oct. 6, 2016, issued in U.S. Appl. No. 15/141,152, 11 pages.

U.S. Office Action dated Nov. 23, 2016, issued in U.S. Appl. No. 15/141,216, 9 pages.

U.S. Office Action dated Nov. 23, 2016, issued in U.S. Appl. No. 15/142,085, 8 pages.

U.S. Office Action dated Feb. 23, 2017, issued in U.S. Appl. No. 29/562,755, 8 pages.

U.S. Office Action dated Feb. 27, 2017, issued in U.S. Appl. No. 29/562,756, 7 pages.

U.S. Office Action dated Mar. 17, 2017, issued in U.S. Appl. No. 15/141,152, 14 pages.

Office Action mailed Sep. 21, 2017, issued in U.S. Appl. No. 15/142,085, 9 pages.

Notice of Allowance mailed Oct. 13, 2017, issued in U.S. Appl. No. 15/481,919, 7 pages.

Office Action mailed Mar. 4, 2019, issued in U.S. Appl. No. 15/444,916, 16 pages.

English translation. Office Action dated Apr. 28, 2019, issued in Chinese Patent Application No. 2017101790491.

Office Action mailed Sep. 17, 2019, issued in U.S. Appl. No. 15/444,916, 17 pages.

Office Action mailed Apr. 15, 2020, issued in U.S. Appl. No. 15/444,916, 16 pages.

Office Action mailed May 17, 2021, issued in Indonesian Patent Application No. PID201808782, 2 pages.

ResMed Vpap III ST-A with QuickNav Clinical Guide, copyright 2008 ("ResMed Guide"). Cited by opposing counsel in connection

(56) References Cited

OTHER PUBLICATIONS with *SoClean Inc. v. Sunset Healthcare Solutions, Inc.*, Civil action No. 1:20-cv-10351-IT (U.S. Dist. Ct. Massachusetts).
Office Action mailed Oct. 20, 2021 in U.S. Appl. No. 17/025,634. 9 pages.
Office Action mailed Mar. 23, 2020, issued in Chinese Patent Application No. 2017101790491, 8 pages. English translation attac.
Goodknight 420G Patient Manual, 2005 Nellcor Puritan Bennett Inc., Ref. M0139DFU02-10, Revision C., 30 pages.
SoClean 2 PAP Disinfecting Device User Guide Copyright 2011-2014, Better Rest Solutions, a division of Inceptus, Inc., pp. 1-20.
CPAP Guardian TB-316, America Tyson Industrial Group (Asia Pacific) Limited, http://www.ecvv.com/products/2314441.html, Nov. 19, 2009, downloaded from Internet Jul. 8, 2016, 3 pages.
Chaunet et al., "The Sterilization Technology for the 21st Century," TS03, Inc. 2007, 3 pages.
Ohkawa et al. "High Grade Disinfection Using High-Density Ozone," J. Adv. Oxid. Technol., 7, 2004, 8 pages.
Office Action dated Apr. 28, 2021 in JP 2019-201674, 3 pages.
First Examination Report issued in Indian Patent Application No. 60/MUMNP/2014, mailed Jul. 10, 2019, 6 pages.
Office Action dated Nov. 18, 2020 in CN 201780025983.6.
Office Action dated May 18, 2021 in CN 201780025983.6.
Office Action dated Nov. 1, 2020 in KR 10-2020-7026960.
Office Action mailed Jul. 26, 2021, issued in Chinese Patent Application No. 2017101790472, 4 pages.
Office Action mailed May 29, 2020, issued in Chinese Patent Application No. 2017101795495, 4 pages.
Office Action mailed Jul. 1, 2020, issued in Chinese Patent Application No. 2017101790472.
Office Action mailed Jul. 3, 2020, issued in Chinese Patent Application No. 2017101786388, 8 pages.
Restriction Requirement issued in related U.S. Appl. No. 17/025,634, mailed Aug. 2, 2021 (6 pages).
Office Action dated May 11, 2021 in BR112018-071444-5.
China Office Action from related matter CN201780025983.6 mailed May 9, 2020.
China Office Action from related matter CN201710179459.5 mailed May 29, 2020.
International Search Report and Written Opinion from related matter PCT/US20/23631 mailed Jun. 3, 2020.
China Office Action from related application CN 201710186091 dated Jul. 1, 2020.
China Office Action from related application CN 20171017904.2 dated Jul. 1, 2020.
US Office Action from related matter U.S. Appl. No. 16/191,059 mailed Jun. 11, 2020.
US Final Office Action from related matter U.S. Appl. No. 16/294,097 mailed Jun. 11, 2020.
US Office Action from related matter U.S. Appl. No. 15/880,962 mailed Jun. 11, 2020.
Office Action mailed Jul. 29, 2019, issued in Chinese Patent Application No. 2017101786091, 10 pages.
Office Action mailed Jul. 29, 2019, issued in Chinese Patent Application No. 2017101790472.
Office Action mailed Aug. 6, 2019, issued in Chinese Patent Application No. 2017101795495, 9 pages.
Notice of Allowance mailed Aug. 8, 2019, issued in U.S. Appl. No. 15/141,152, 8 pages.
Examination Report mailed Aug. 13, 2019, issued in Australian Patent Application No. 2018200514, 6 pages.
Notice of Acceptance mailed Aug. 14, 2019, issued in Australian Patent Application No. 2017228723, 4 pages.
Notice of Allowance mailed Oct. 8, 2019, issued in Japanese Application No. 2017-149891, 4 pages.
Examination Report mailed Jun. 7, 2019, issued in Canadian Patent Application No. 3,005,981, 3 pages.
Office Action mailed Jan. 8, 2021, issued in Chinese Patent Application No. 2017101786388, 8 pages.
Notice of Allowance mailed Nov. 15, 2019, issued in Australian Patent Application No. 2018200514, 4 pages.
Extended Search Report mailed Nov. 29, 2019, issued in European Patent Application No. 17790471.1, 9 pages.
Examination Report mailed Jan. 13, 2020, issued in Chilean Patent Application No. 201803063, 17 pages. English language machine translation included.
Office Action mailed Feb. 3, 2020, issued in U.S. Appl. No. 16/190,996, 9 pages.
Office Action mailed Feb. 18, 2020, issued in Canadian Patent Application No. 3,005,981, 3 pages.
Office Action mailed Mar. 19, 2020, issued in Korean Patent Application No. 10-2020-7003298, 4 pages.
Office Action mailed Apr. 7, 2020, issued in U.S. Appl. No. 16/780,492, 13 pages.
Office Action mailed Apr. 13, 2020, issued in U.S. Appl. No. 16/782,892, 15 pages.
Notice of Allowance mailed Apr. 28, 2020, issued in U.S. Appl. No. 16/780,492, 7 pages.
Office Action mailed Apr. 23, 2020, issued in U.S. Appl. No. 16/780,355, 14 pages.
Final Office Action mailed Feb. 5, 2019, issued in U.S. Appl. No. 15/141,152, 14 pages.
Examination Report mailed Feb. 15, 2019, issued in Australian Patent Application No. 2018200514, 5 pages.
Notice of Allowance mailed Apr. 30, 2019, issued in U.S. Appl. No. 15/441,929, 5 pages.
Office Action mailed Mar. 4, 2019, issued in U.S. Appl. No. 16/257,898, 13 pages.
Office Action mailed Mar. 14, 2019, issued in U.S. Appl. No. 16/270,141, 12 pages.
Notice of Allowance mailed Mar. 19, 2019, issued in U.S. Appl. No. 15/499,456, 12 pages.
Extended European Search Report from related Application No. 20773414.6 mailed Nov. 17, 2022. 4 pages.
Office Action mailed Apr. 2, 2019, issued in Japanese Patent Application No. 2017-0149891, 7 pages.
Office Action mailed Oct. 30, 2018, issued in U.S. Appl. No. 15/499,456, 13 pages.
Notice of Allowance mailed Oct. 31, 2018, issued in U.S. Appl. No. 15/873,506, 8 pages.
Office Action amendment mailed Oct. 31, 2018, issued in U.S. Appl. No. 15/499,456, 13 pages.
Office Action mailed Nov. 6, 2018, issued in U.S. Appl. No. 15/499,378, 18 pages.
Keep your CPAP machine clean and safe, Oct. 18, 2010—Available at https://www.cpap.co.uk/2010/10/keep-your-cpap-machine-clean-and-safe. 5 pages.
GoodKnight H20 Heated Humidifier User's Manual, 2006 Nellcor Puritan Bennett, Ref.: M-146DFU00-20, Revision D, 22 pages.
Hoffrichter Trend II User's Manual (date unknown), Germany, pp. 1-80.
Hudson RCI Product Catalog, 2004-2005, pp. 1-87.
KnightStar(R) 330 User's Manual, 2006, Nellcor Puritan Bennett, Y-500009-00 Rev. J., 68 pages.
DeVilbiss® DV54 AutoAdjust CPAP Series (DeVilbiss® SleepCube Positive Airway Pressure Device) User Manual (2009). Available at https://www.manualslib.com/manual/1577762/Devilbiss-Intellipap-Dv54.html, pp. 1-17.
Sunset Healthcare Solutions, Inc's Preliminary Patent Disclosures Pursuant to Local Rule 16.6(d)(4) in *SoClean, Inc. v. Sunset Healthcare Solutions, Inc*, in Civil Action No. 1:20-cv-10351-IT, 60 pages.
Sunset Healthcare Solutions, Inc's Second Amended Counterclaims in *SoClean, Inc. v. Sunset Healthcare Solutions, Inc*, in Civil Action No. 1:20-cv-10351-IT and Consolidated Case No. 1:21-cv-1013IT, 30 pages.
Memorandum in Support of SoClean's Motion to Dismiss Counts Eight and Nine of Sunset's Second Amended Counterclaims, *SoClean, Inc. v. Sunset Healthcare Solutions, Inc*, in Civil Action No. 1:20-cv-10351-IT and Consolidated Case No. 1:21-cv-1013IT. 165 pages.

(56) References Cited

OTHER PUBLICATIONS

Defendant Sunset's Memorandum in Opposition to SoClean's Motion to Dismiss Counts Eight and Nine of Sunset's Second Amended Counterclaims. C.A. No. 1:20-cv-10351-IT. Filed Aug. 6, 2021. 39 pages.
Preliminary Report on Patentability mailed Nov. 7, 2019, issued in PCT Patent Application No. PCT/US2018/029140, 11 pages.
VPAP IV and VPAP IV ST Product Training ("ResMed Presentation"). Cited by opposing counsel in connection with *SoClean Inc. v. Sunset Healthcare Solutions, Inc*, Civil action No. 1:20-cv-10351-IT (U.S. Dist. Ct. Massachusetts). Publication Date is unknown to Applicant, but was asserted by opposing counsel in the noted litigation to be in 2008.
Lenntech "Ozone Generation", Wayback Machine Capture, Mar. 28, 2010, pp. 1-3.
Ozone MSDS (Material Safety Data Sheets), Ozone Solutions, Jun. 1, 2000, http://www.ozoneapplications.com/info/ozone_msds.htm, pp. 1-5 .
Tornado, New Kind of CPAP Guardian, User Manual, 8 pages.
Murphy, "Ozone—The Latest Advance in Sterilization of Medical Developments", Canadian Operating Room Nursing Journal; Jun. 2006, pp. 28, 30-32, 37 and 38.
9055 Series DeVilbiss RPM Bilevel CPAP System Instruction Manual, pp. 1-66.
Ishizaki, et al., "Inactivation of Bacillus spores by gaseous ozone", Journal of Applied Bacteriology 1986:60, 67-72.
Al Ashry, et al., "Humidification during Mechanical Ventilation in the Adult Patient", vol. 2014, Article ID 715434, Hindawi Publishing Corporation, BioMed Research International, pp. 1-12.
Office Action from related Japanese Appln. No. 2021-131430, dated Jun. 10, 2022. English translation attached. 9 pages.
International Search Report and Written Opinion from corresponding PCT Appln. No. PCT/US2023/032840, dated Nov. 7, 2023. 7 pages.
SoClean Sterisafe PowerPoint Presentation, "Mission Booster Feasability Study Conclusions", Sep. 14, 2022, 31 slides.
SoClean Humidifier PowerPoint Presentation, "Bettering Lives Through the Power of a Better Clean", Sep. 16, 2022, 16 slides.
SoClean Purpose, Scope & Executive Summary PowerPoint Presentation, 52 slides.
Final Office Action mailed Jul. 12, 2023, issued in U.S. Appl. No. 17/013,280, 13 pages.
Office Action from related Chinese Appln. No. 2020800368587, dated Jan. 20, 2023. English translation attached. 10 pages.
Office Action mailed Jan. 23, 2023, issued in U.S. Appl. No. 17/013,280,14 pages.
Office Action mailed Dec. 28, 2023, issued in U.S. Appl. No. 17/239,112, 10 pages.
Office Action mailed Apr. 22, 2022, issued in U.S. Appl. No. 17/464,154, 12 pages.
International Search Report and Written Opinion from corresponding PCT Appln. No. PCT/us2024/022497, dated Oct. 28, 2024. 14 pages.
Office Action from related U.S. Appl. No. 18/623,620 dated Aug. 21, 2024. 15 pages.

* cited by examiner

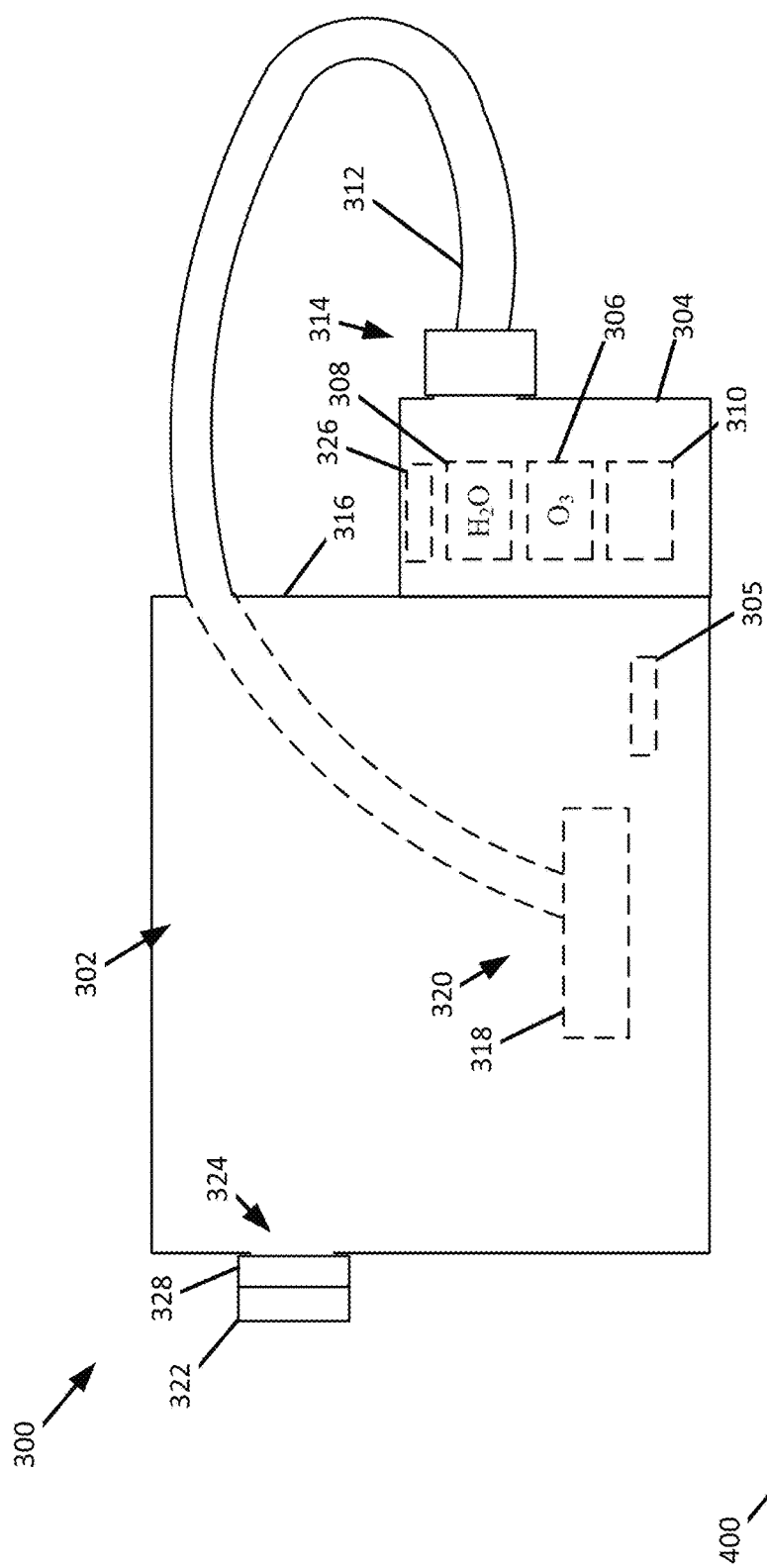
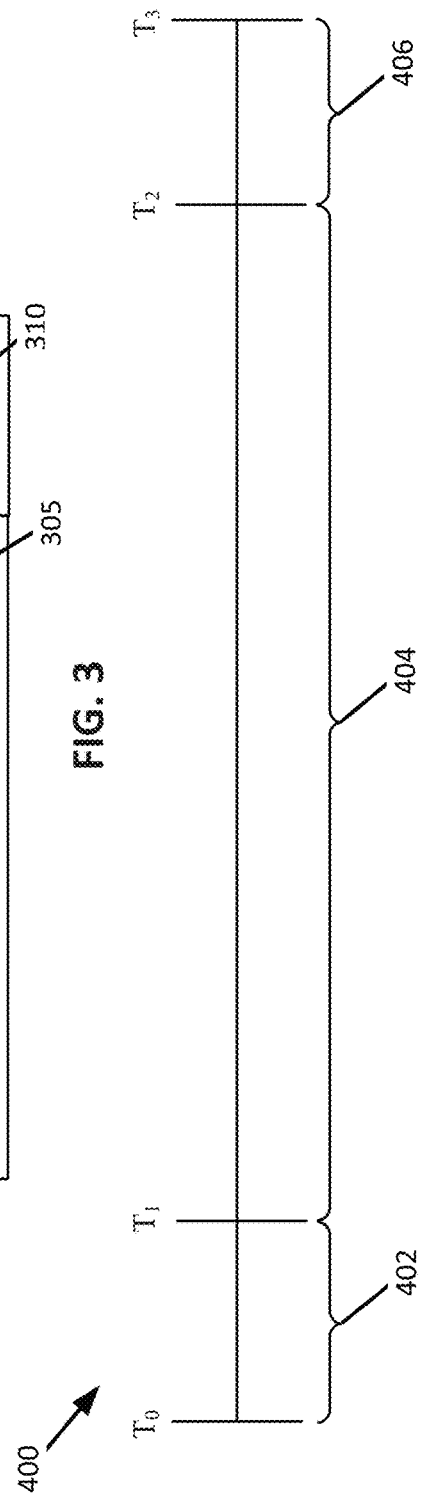
FIG. 3
FIG. 4

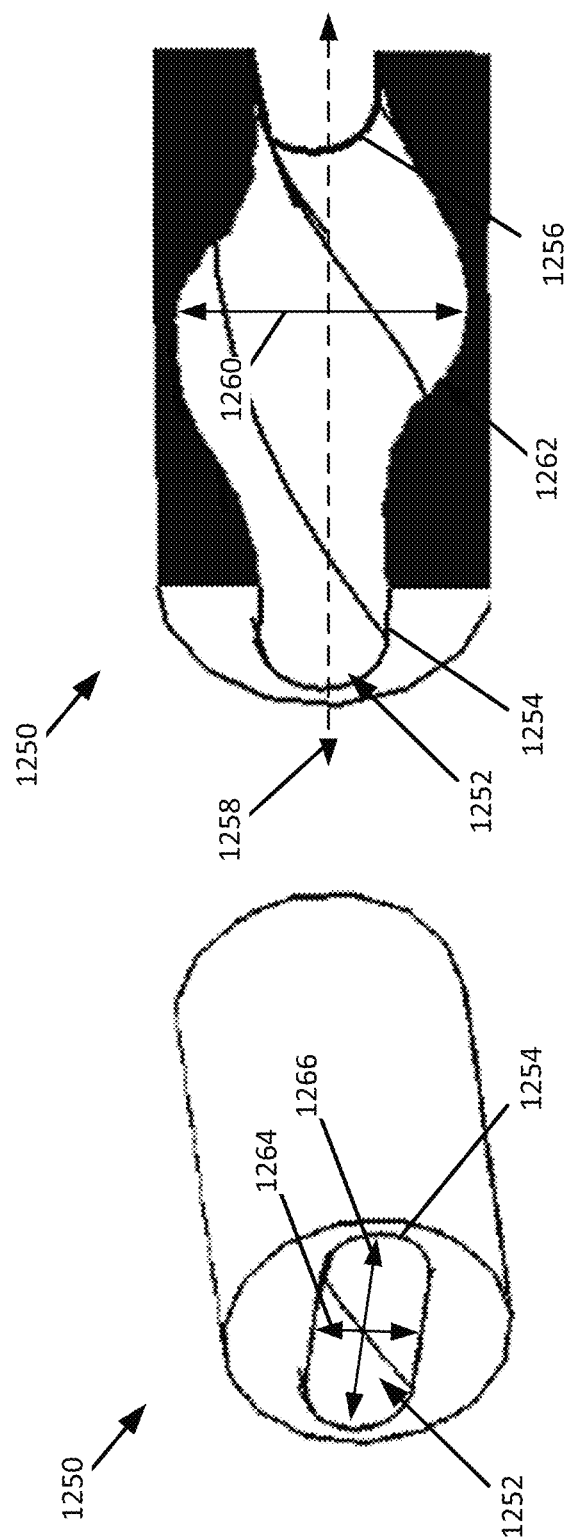

DISINFECTION SYSTEMS AND METHODS

CROSS-REFERENCE TO RELATED APPLICATIONS

The present application is a continuation of U.S. application Ser. No. 18/368,598 filed on Sep. 15, 2023, entitled Disinfection Systems and Methods, which claims the benefit of U.S. Provisional Application Ser. No. 63/458,578 filed on Apr. 11, 2023, entitled Disinfection Systems and Methods, U.S. Provisional Application Ser. No. 63/458,527, filed on Apr. 11,2023, entitled Disinfection Systems and Methods, and U.S. Provisional Application Ser. No. 63/375,992 filed on Sep. 16, 2022, entitled Technologies for Sanitizing Medical Devices, each of which are fully incorporated herein by reference.

TECHNICAL FIELD

The present disclosure is generally directed to disinfection systems and methods and more specifically to disinfection systems and methods using ozone.

BACKGROUND INFORMATION

Devices (e.g., medical devices, such as a mask, consumer devices, nebulizers etc.) are exposed to numerous environments in which pathogens (e.g., harmful bacteria and/or viruses) can come into contact with and reside on the devices. Without proper disinfection, further use of these devices after exposure can result in the spread of the pathogens. Accordingly, before reuse, devices may be disinfected in order to reduce the risk of spreading an infection to a user.

One example of a medical device is a mask, which may be coupled to one or more hoses (e.g., a continuous positive airway pressure mask and hose, a respirator mask, and/or any other type of mask). Masks are worn on a user's face and any hoses connected to the mask may come into direct contact with bodily fluids exhaled from a user's mouth and/or nose. These fluids may include pathogens. Accordingly, reuse of a mask, without proper disinfection, may increase a risk of infection.

Further, a hose coupled to the mask may include one or more crevices formed by a helical rib extending at least a substantial length of the hose and one or more pathogens may reside throughout the hose. The hose and/or the mask may include one or more regions (e.g., the crevices) which are difficult to disinfect. For example, a CPAP hose may include several crevices along the about 1.5 meter (m) to about 3 m length of the CPAP hose and/or the CPAP mask may have one or more difficult to disinfect places around the nasal passageways. The difficulty associated with disinfecting these regions may result in a build-up of one or more pathogens that may eventually pass to a user. Additionally, in some instances, a length of the CPAP hose may increase a difficulty in getting a disinfection fluid to traverse the entire length of the CPAP hose while achieving a desired disinfection performance, which may also lead to a build-up of one or more pathogens.

BRIEF DESCRIPTION OF THE DRAWINGS

These and other features advantages will be better understood by reading the following detailed description, taken together with the drawings wherein:

FIG. 3 shows a schematic example of a disinfection device with humidity control configured to disinfect one or more components of a continuous positive air pressure (CPAP) machine, consistent with embodiments of the present disclosure.

FIG. 4 shows a schematic example of an operational timeline for the disinfection device of FIG. 3, consistent with embodiments of the present disclosure.

FIG. 12B shows an example of an insert configured to be coupled to (or formed from) a humidification chamber ozone inlet of the humidifier assembly of FIG. 11, consistent with embodiments of the present disclosure.

FIG. 12C shows a cross-sectional view of the insert of FIG. 12B, consistent with embodiments of the present disclosure.

DETAILED DESCRIPTION

Figure 1:
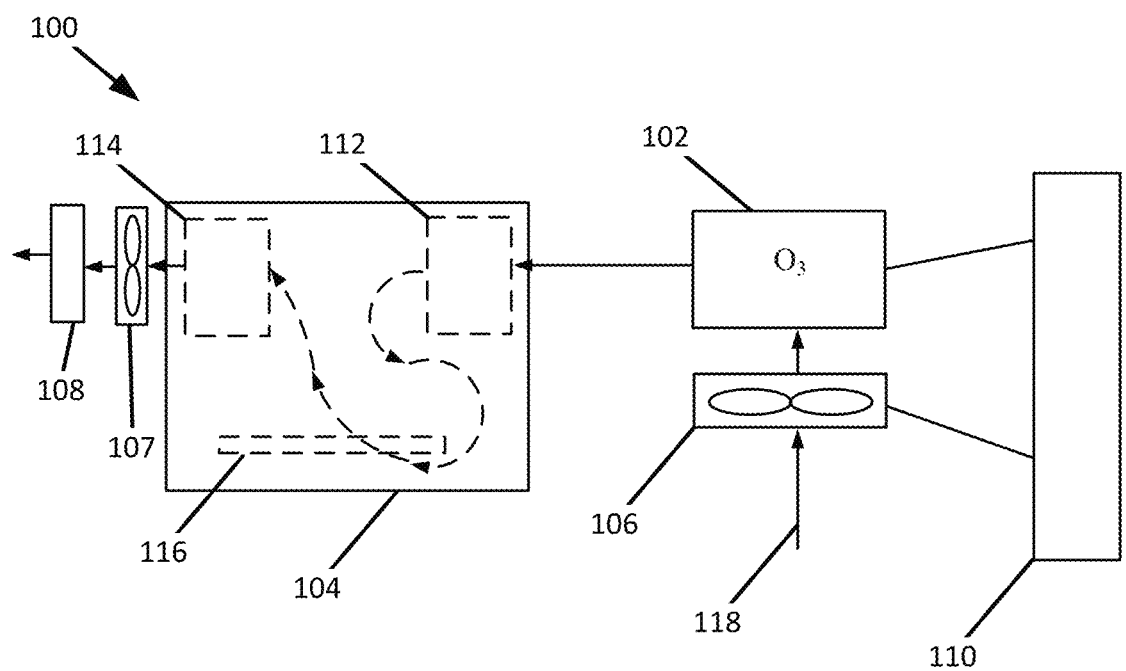
FIG. 1 shows a schematic block diagram of an example of a disinfection device, consistent with embodiments of the present disclosure.

The present disclosure is generally directed to a disinfection device having humidity and/or disinfection performance control. The disinfection device includes an ozone generator, a humidifier, and a disinfection chamber. The ozone generator is configured to generate ozone such that generated ozone can become entrained within air passing through the ozone generator to create ozonated air. Ozonated air may pass through the humidifier and into the disinfection chamber. The ozone generator and the humidifier may be selectively enabled and disabled according to an operation profile. In one example, humidified ozonated air may pass from the humidifier and into the disinfection device via a medical device (e.g., a continuous positive air pressure (CPAP) hose and/or mask).

In some instances, the disinfection device may be configured to disinfect a CPAP hose and CPAP mask. For example, the disinfection device may be configured to achieve a disinfection performance of at least 4-$Log_{10}$ (at least a 99.99% reduction) for a given one or more pathogens (e.g., viruses, bacteria, and/or any other pathogen) disposed on at least a portion of the CPAP hose and CPAP mask. In one example, the CPAP hose may have a length in a range of about 1.5 meters (m) to about 3 m, a diameter of about 3.8 centimeters (cm) to about 5 cm, and a connection point at a distal end at which the CPAP mask is coupled (e.g., removably coupled). As the CPAP mask is worn by a user, pathogens may be present in the greatest quantities at the CPAP mask and/or at a region of the CPAP hose proximate to the connection point. As such, in some instances, the disinfection device may be configured such that disinfection performance at a region of the CPAP hose proximate to the connection point, at the CPAP mask (e.g., internal and/or external surfaces of the CPAP mask), and/or for an entire length of the CPAP hose is at least 4-$\text{Log}_{10}$.

In some instances, the humidifier may be configured to humidify the disinfection chamber prior to (or after) the generation of ozone. In these instances, ozone may not pass through the humidifier prior to entering the disinfection chamber. For example, the disinfection device may be configured to undergo a pre-humidification step in which a relative humidity within the disinfection chamber is achieved prior to the generation of ozone.

Addition of humidity to ozonated air may improve the disinfection performance of the ozonated air. Further, how the humidity is generated (e.g., using a bubbler system, a piezo-electric atomizer, a sprayer, a heat source, evaporation, and/or the like) may influence the disinfection performance of the ozonated air. Additionally, or alternatively, a size of water droplets generated by the humidifier that become entrained within the ozonated air may also influence the disinfection performance of the ozonated air. Further, the flow rate of the ozonated air, relative humidity of the environment, and/or exposure time to ozonated air may influence the disinfection performance.

One example operation profile may include a first period, a second period, and a third period. During the first period both the ozone generator and the humidifier may be operated continuously. During the second period, the humidifier may be disabled and the ozone generator may be pulsed (e.g., selectively enabled/disabled) according to a constant (or non-constant) pulse rate. During the third period, both the humidifier and the ozone generator may be disabled.

In some instances, the disinfection device, when operated according to an appropriate operation profile, may achieve at least a 4-$\text{Log}_{10}$ kill rate for at least one pathogen (e.g., bacterial or viral) on an object within the disinfection chamber and/or within a flow path of the ozonated air (e.g., humidified ozonated air). In other words, the disinfection device may be configured to cause at least a 99.99% reduction of at least one pathogen. In other instances, the disinfection device, when operated according to an appropriate operation profile, may achieve at least a 6-$\text{Log}_{10}$ kill rate for a pathogen on an object within the disinfection chamber and/or within a flow path of the ozonated air (e.g., humidified ozonated air). In other words, the disinfection device may be configured to cause at least a 99.9999% reduction of at least one pathogen. One example method for determining whether the disinfection device achieves a desired kill rate includes generating an inoculate having a sufficient quantity of one or more pathogens suspended therein to establish the desired reduction of the one or more pathogens was achieved and applying the inoculate to an object to be disinfected (e.g., a CPAP hose and/or a CPAP mask).

Although the technologies described herein can be used with many disinfection fluids, the present disclosure focuses on the use of ozone as a disinfecting gas. This is because ozone ($O_3$) gas is a relatively powerful disinfector yet can be safely used within a consumer product. Because of its strong oxidizing properties, ozone can effectively kill or otherwise remove a wide range of organic and inorganic contaminants such as yeasts, bacteria, molds, viruses, other pathogens, and/or pollutants with which it comes into contact (e.g., via oxidation). Naturally over time and/or as it oxidizes contaminants, ozone is chemically reduced to oxygen ($O_2$), which is safe for human consumption and for release into the environment. Ozone is also relatively easy to generate on site (and, thus, does not require the use of a storage tank), and leaves little or no chemical residue. For those and other reasons, ozone has been identified as a safe and effective disinfecting gas for use in the present disclosure. It should be understood, however, that the technologies described herein are not limited to the use of ozone and may be employed with a wide variety of disinfection fluids.

FIG. 1 shows a schematic block diagram of a disinfection device 100. The disinfection device 100 includes an ozone generator 102, a disinfection chamber 104, at least one pump 106 configured to cause air to pass into the ozone generator 102 and into the disinfection chamber 104, an ozone reduction filter 108 configured to breakdown ozone into oxygen, and a controller 110 configured to control operations of one or more of the ozone generator 102 and/or the pump 106.

The disinfection chamber 104 may include a disinfection chamber inlet 112, a disinfection chamber outlet 114, and define a volume (e.g., a selectively enclosable volume) that is configured to receive at least a portion of an object 116 (e.g., a medical device). The ozone reduction filter 108 can be positioned at (e.g., upstream of or downstream of) the disinfection chamber outlet 114. The ozone reduction filter 108 can be made of an ozone porous material that is configured to reduce ozone to oxygen. For example, the ozone reduction filter 108 may be a reticulated foam that is formed from, includes, and/or is coated with a material that reduces ozone to oxygen. Non-limiting examples of filter materials include activated carbon, magnesium oxide, and/or magnesium dioxide (either alone or in combination with activated carbon); however, other materials may be used.

In operation, the ozone generator 102 is caused to generate ozone and the pump 106 is configured to cause air to flow along a flow path 118. The flow path 118 passes through the ozone generator 102 into the disinfection chamber 104 and passes through the disinfection chamber outlet 114. The generated ozone is carried with the flow of air (which may generally be referred to as ozonated air) into the disinfection chamber 104. Once in the disinfection chamber 104, the ozone acts to disinfect the object 116 present within the disinfection chamber 104.

The rate of ozone generation and the flow rate of the air passing through the ozone generator 102 is controlled by the controller 110. For example, the controller 110 may cause the pump 106 and/or a fan 107 to generate a desired flow rate of air through the disinfection device 100. In this example, the pump 106 and the fan 107 may be operated at different speeds such that air flows through the disinfection device according to a flow rate. In this example, when the pump 106 generates a different (e.g., greater) flow rate than the fan 107, the disinfection performance may be improved. For example, the pump 106 generating a greater flow rate than the fan 107 may encourage a disinfection performance of at least 4-$\text{Log}_{10}$. In some instances, the controller 110 may be configured to control the disinfection device 100 such that a pressure and/or a vacuum is generated within the disinfection chamber 104. In other words, the controller 110 is configured to control the environment within the disinfection chamber 104 (e.g., the rate with which ozone is delivered to and/or removed from the disinfection chamber 104 may be used to adjust an amount of ozone within the disinfection chamber 104).

Varying the condition of the environment within the disinfection chamber 104 may influence an effectiveness of the disinfection of the object 116 within the disinfection chamber 104. For example, an amount of moisture within the air flow (humidity) may have an impact on disinfection effectiveness. In this example, humidified air may improve the disinfection effectiveness, potentially, allowing less ozone to be generated to achieve a desired amount of disinfection (e.g., a bacterial and/or viral kill rate). Generation of less ozone may, for example, improve the longevity of the ozone reduction filter 108.

Figure 2:
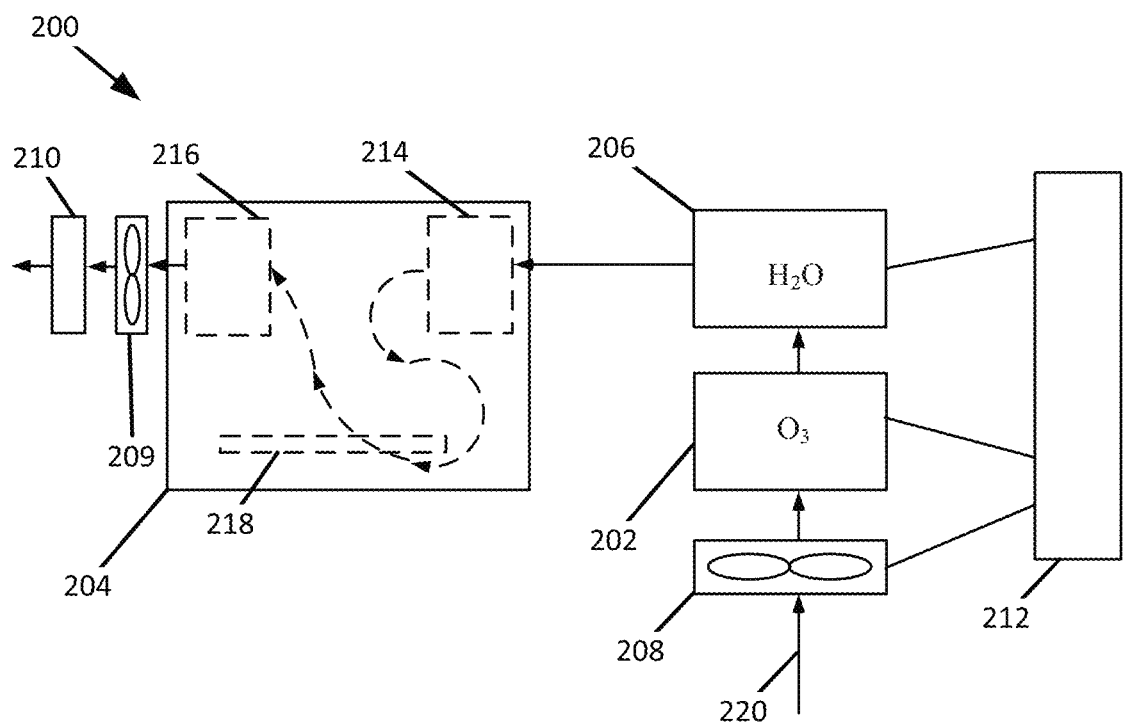
FIG. 2 shows a schematic block diagram of an example of a disinfection device with humidity control, consistent with embodiments of the present disclosure.

FIG. 2 shows a schematic block diagram of a disinfection device 200 with humidity control. The disinfection device 200 includes an ozone generator 202, a disinfection chamber 204, a humidifier 206, at least one pump 208 configured to cause air to pass through the ozone generator 202 and the humidifier 206 and into the disinfection chamber 204, an ozone reduction filter 210 configured to breakdown ozone into oxygen, and a controller 212 configured to control operations of one or more of the ozone generator 202, the humidifier 206, and/or the pump 208. In some instances, the disinfection device 200 may further include a fan 209 downstream of the pump 208 and upstream of the ozone reduction filter 210. The controller 212 may be further configured to control operation of the fan 209. For example, the controller 212 may be configured to cause the fan 209 to operate at a different (e.g., slower) flow rate than the pump 208.

The disinfection chamber 204 may include a disinfection chamber inlet 214, a disinfection chamber outlet 216, and define a volume (e.g., a selectively enclosable volume) that is configured to receive at least a portion of an object 218 (e.g., a medical device). The ozone reduction filter 210 can be positioned at (e.g., upstream of or downstream of) the disinfection chamber outlet 216. The ozone reduction filter 210 can be an ozone porous material that is configured to reduce ozone to oxygen. For example, the ozone reduction filter 210 may be a reticulated foam that is formed from, includes, and/or is coated with a material that reduces ozone to oxygen. Non-limiting examples of filter materials include activated carbon, magnesium oxide, and/or magnesium dioxide (either alone or in combination with activated carbon); however, other materials may be used.

In operation, the pump 208 is configured to cause air to flow along a flow path 220. The flow path 220 extends through the ozone generator 202, the humidifier 206, the disinfection chamber 204, and the ozone reduction filter 210. The ozone generator 202 is configured to generate ozone as air passes through the ozone generator 202. When the ozone generator 202 is generating ozone, air exiting the ozone generator 202 includes ozone entrained therein (which may generally be referred to as ozonated air). The ozonated air enters the humidifier 206, wherein the humidifier 206 is configured to mix or combine the ozonated air with humidity. In some instances, ozone may become entrained within droplets of moisture generated by the humidifier 206. In some instances, the humidifier 206 may be configured to selectively humidify the ozonated air. For example, the humidifier 206 may be selectively operated such that ozonated air can pass therethrough without humidification. Such a configuration, may allow the controller 212 to regulate the humidity within the disinfection chamber 204 independently of the amount of ozone. Additionally, or alternatively, the humidifier 206 may be positioned upstream of the ozone generator 202 such that the humidifier 206 adds humidity to non-ozonated air.

In some instances, when the disinfection device 200 includes the fan 209, the fan 209 may be configured to cooperate with the pump 208 to deliver ozonated air to the disinfection chamber 204. The pump 208 may be configured to push ozonated air into the disinfection chamber 204 (e.g., the pump 208 may be fluidly coupled to the disinfection chamber 204 at a location upstream of the disinfection chamber 204) and the fan 209 may be configured to pull ozonated air into the disinfection chamber 204 (e.g., the fan 209 may be fluidly coupled to the disinfection chamber at a location downstream of the disinfection chamber 204). For example, the fan 209 may be configured to pull ozonated air into the disinfection chamber 204 at a first flow rate and the pump 208 may be configured to push ozonated air into the disinfection chamber 204 at a second flow rate, the second flow rate being different the first flow rate. In this example, during a disinfection cycle, the second flow rate may be greater than the first flow rate and, during a purge cycle (e.g., after completion of the disinfection cycle), the first flow rate may be greater than (or the same as) the second flow rate (e.g., in some instances, the second flow rate may be zero) in order to encourage the purging of ozonated air from the disinfection device 200. In some instances, the disinfection device may be configured such that the disinfection chamber 204 is under pressure and/or under vacuum.

FIG. 3 shows a schematic example of a disinfection device 300 with humidity control configured to disinfect one or more components of a continuous positive air pressure (CPAP) machine. The disinfection device 300 is an example of the disinfection device 200 of FIG. 2.

As shown, the disinfection device 300 includes a disinfection chamber 302 and an ozone and humidity generation assembly 304 external to the disinfection chamber 302 (e.g., the ozone and humidity generation assembly 304 may be coupled to an external surface of a sidewall 316 of the disinfection chamber 302). The ozone and humidity generation assembly 304 includes an ozone generator 306, a humidifier 308, and a pump 310 configured to urge air through the ozone generator 306 and the humidifier 308. The ozone generator 306, the humidifier 308, and the pump 310 are configured to cooperate together (e.g., to generate humidified ozonated air), forming the ozone and humidity generation assembly 304. In some instances, a chamber relative humidity sensor 305 may be configured to measure a relative humidity of the disinfection chamber 302. In these instances, an operation of the humidifier 308 may be controlled based, at least in part, on output from the chamber relative humidity sensor 305.

The ozone and humidity generation assembly 304 is configured to be removably coupled to a CPAP hose 312 at a first end 314 such that the CPAP hose 312 is fluidly coupled to the ozone generator 306, the humidifier 308, and the pump 310. The CPAP hose 312 is configured to fluidly couple the ozone and humidity generation assembly 304 to the disinfection chamber 302. For example, and as shown, the CPAP hose 312 is configured to pass through the sidewall 316 of the disinfection chamber 302. By way of further example, the CPAP hose 312 may be configured to removably couple to a coupling that is fluidly coupled to the disinfection chamber 302. In some instances, a CPAP mask 318 may be disposed within the disinfection chamber 302. For example, the CPAP mask 318 may be coupled to the CPAP hose 312 at a second end 320, the second end 320 being opposite the first end 314. A length of the CPAP hose 312 extending between the first and second ends 314 and 320 may be, for example, in a range of about 1.5 meters (m) to 3 m. By way of further example, a length of the CPAP hose 312 extending between the first and second ends 314 and 320 may be about 1.8 m. An ozone reduction filter 322 may be disposed at an outlet 324 of the disinfection chamber 302. In some instances, a fan 328 may be provided to draw ozonated air from the disinfection chamber 302 and urge the ozonated air through the ozone reduction filter 322.

The humidifier 308, the pump 310, and/or the ozone generator 306 may be arranged in any configuration relative to the disinfection chamber 302 and/or may be disposed within separate or common housings. For example, one or more of the humidifier 308, the pump 310, and/or the ozone generator 306 may be arranged at least partially below the disinfection chamber 302. Additionally, or alternatively, and by way of further example, one or more of the humidifier 308, the pump 310, and/or the ozone generator 306 may be arranged at least partially along a side of and/or separate from the disinfection chamber 302. In some instances, one or more of the humidifier 308, the pump 310, and/or the ozone generator 306 may be movable relative to the disinfection chamber 302. For example, when the disinfection chamber 302 is in the form of a flexible bag, one or more of the humidifier 308, the pump 310, and/or the ozone generator 306 may be disposed within one or more external housings and be configured to fluidly couple to the disinfection chamber 302 via the CPAP hose 312.

In operation, a controller 326 is configured to selectively control each of the ozone generator 306, the humidifier 308, the pump 310, and/or the fan 328 to control an environment within the disinfection chamber 302. For example, the controller 326 may be configured to selectively urge air, ozonated air, or humidified ozonated air through the CPAP hose 312 and into the disinfection chamber 302 in order to disinfect the CPAP hose 312 and the CPAP mask 318. In this example, when the humidity has reached a desired level (e.g., estimated and/or measured), the humidifier 308 may be disabled and/or pulsed at a constant or non-constant pulse rate, and/or, when the ozone has reached a desired level (e.g., estimated and/or measured), the ozone generator 306 may be disabled and/or pulsed at a constant or non-constant pulse rate.

FIG. 4 shows a schematic example of an operational timeline 400 of the disinfection device 300 that corresponds to one example disinfection cycle. As shown, a first period (e.g., an initialization period) 402 extends between time $T_0$ and time $T_1$, a second (e.g., an operation) period 404 extends between time $T_1$ and time $T_2$, and a third (e.g., a purge) period 406 extends between time $T_2$ and time $T_3$. Time $T_3$ may be greater than time $T_2$, time $T_2$ may be greater than time $T_1$, and time $T_1$ may be greater than time $T_0$. The first period 402 may generally be referred to as a period in which the ozone and humidity generation assembly 304 is operated to achieve a desired initial condition (e.g., within a desired humidity and/or ozone range) within the hose 312, the mask 318, and/or the disinfection chamber 302 (the determination of whether the initial condition has been achieved may be estimated and/or measured). The second period 404 may generally be referred to as a period in which the ozone and humidity generation assembly 304 is operated to maintain a desired condition (e.g., within a desired humidity and/or ozone range that is estimated and/or measured). The third period 406 may generally be referred to as the period in which the ozone and humidity generation assembly 304 is operated to purge the ozone from the disinfection chamber 302 such that any residual ozone within the disinfection chamber 302 is removed and/or within an acceptable level.

In one example, during the first period 402, the ozone generator 306, the humidifier 308, the pump 310, and the fan 328 may be operated continuously or intermittently, during the second period 404, the ozone generator 306 may be operated continuously or intermittently, the humidifier 308 may be disabled, the pump 310 may be operated continuously or intermittently, and the fan 328 may be operated continuously or intermittently, and, during the third period 406, the ozone generator 306 and humidifier 308 may be disabled, the pump 310 may be operated continuously or intermittently, and the fan 328 may be operated continuously or intermittently. In another example, during the first period 402, one or more of the ozone generator 306, the humidifier 308, the pump 310, and/or the fan 328 may be operated continuously or intermittently, during the second period 404, one or more of the ozone generator 306, the humidifier 308, the pump 310, and/or the fan 328 may be disabled, and, during the third period 406, the ozone generator 306 and humidifier 308 may be disabled, the pump 310 may be operated continuously or intermittently, and the fan 328 may be operated continuously or intermittently.

A length of the first period 402, the second period 404, and the third period 406 may be predetermined or based, at least in part, on sensed conditions (e.g., within the disinfection chamber 302, the CPAP hose 312, and/or the CPAP mask 318) and/or estimated conditions (e.g., within the disinfection chamber 302, the CPAP hose 312, and/or the CPAP mask 318). Introduction of humidity during the first period 402 may result in one or more pathogens becoming more susceptible to breakdown by ozone.

While the terms, first, second, and third, are used to described the first period 402, the second period 404, and the third period 406, the terms first, second, and third are not intended to convey a specific order. For example, in some instances, the second period 404 and/or third period 406 may come before the first period 402. In some instances, there may be one or more additional periods that come before or after one or more of the first, second, and/or third periods 402, 404, and/or 406.

Figure 5:
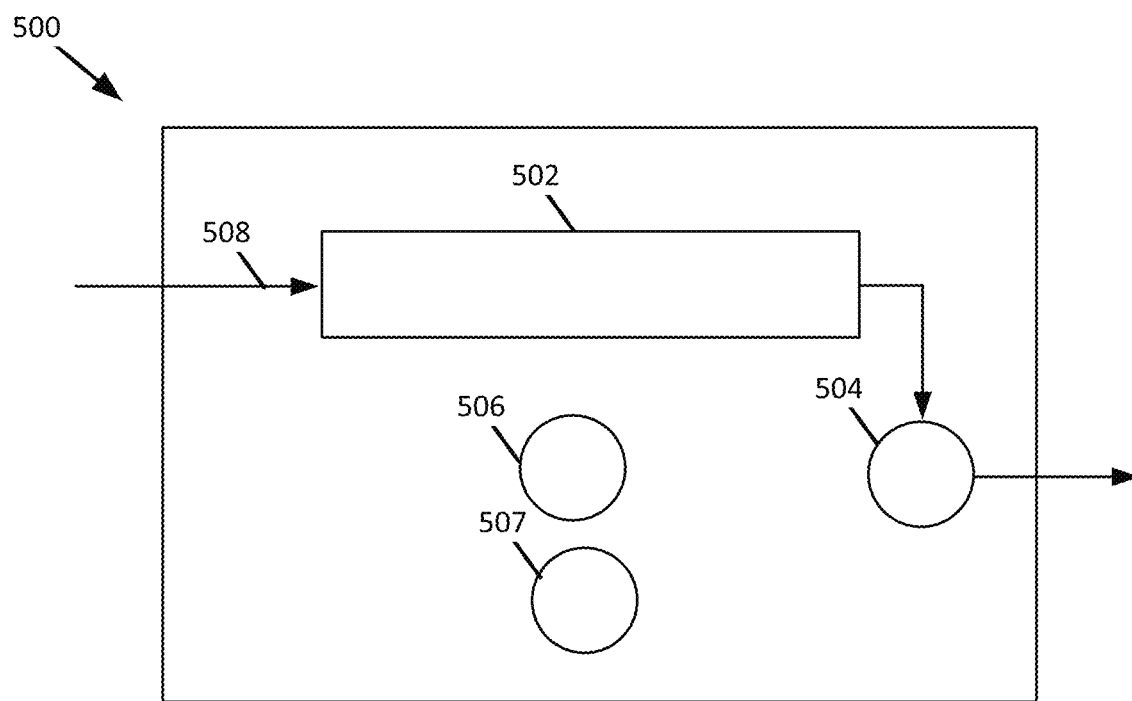
FIG. 5 shows a schematic example of an ozone generator, consistent with embodiments of the present disclosure.

FIG. 5 is a schematic example of an ozone generator 500, which is an example of the ozone generator 202 of FIG. 2. As shown, the ozone generator 500 includes an ozone source 502, an ozone sensor 504, a humidity sensor 506 (e.g., a relative humidity sensor), and, in some instances, a temperature sensor 507. The ozone source 502, the ozone sensor 504, the humidity sensor 506, and the temperature sensor 507 may be communicatively coupled to the controller 212 (FIG. 2). For example, the controller 212 may be configured to control operation of the ozone source 502 based, at least in part, on outputs from the ozone sensor 504, the humidity sensor 506, and/or the temperature sensor 507. The ozone sensor 504 may be configured to measure a quantity of ozone within air exiting the ozone sensor 504. The humidity sensor 506 may be configured to measure a relative humidity of air entering the ozone source 502 (e.g., the relative humidity within a surrounding environment such as a room within which the ozone generator 500 is located). The temperature sensor 507 may be configured to measure a temperature of air entering the ozone source 502 (e.g., the temperature within a surrounding environment such as a room within which the ozone generator 500 is located). In one example, the controller 212 may operate the ozone source 502 at an initial operation level based, at least in part, on the relative humidity and measure the output of the ozone source 502 using the ozone sensor 504, wherein the initial operation level corresponds to an estimated amount of ozone to be generated. The measured output of the ozone source 502 may be used to adjust an amount of ozone generated by the ozone source 502 until a desired ozone output is obtained. In some instances, the humidity sensor 506 and the temperature sensor 507 may be collectively referred to as a humidity/temperature sensor. In these instances, the humidity sensor 506 and the temperature sensor 507 may be part of the same sensor assembly or may be separate sensors.

As shown, in operation air is caused to flow along an ozone generator flow path 508 (which forms a portion of the flow path 220, FIG. 2). The ozone generator flow path 508 extends through the ozone source 502 and the ozone sensor 504, the ozone sensor 504 being downstream of the ozone source 502. For example, the ozone sensor 504 may be downstream of the ozone source 502 and upstream of a humidifier (e.g., the humidifier 206 of FIG. 2) and/or a disinfection chamber (e.g., the disinfection chamber 204 of FIG. 2). By way of further example, the ozone sensor 504 may be downstream of the ozone source 502 and a humidifier (e.g., the humidifier 206 of FIG. 2) and upstream of a disinfection chamber (e.g., the disinfection chamber 204 of FIG. 2). By way of still further example, the ozone sensor 504 may be downstream of the ozone source 502 and a humidifier (e.g., the humidifier 206 of FIG. 2) and disposed within a disinfection chamber (e.g., the disinfection chamber 204 of FIG. 2).

Figure 6:
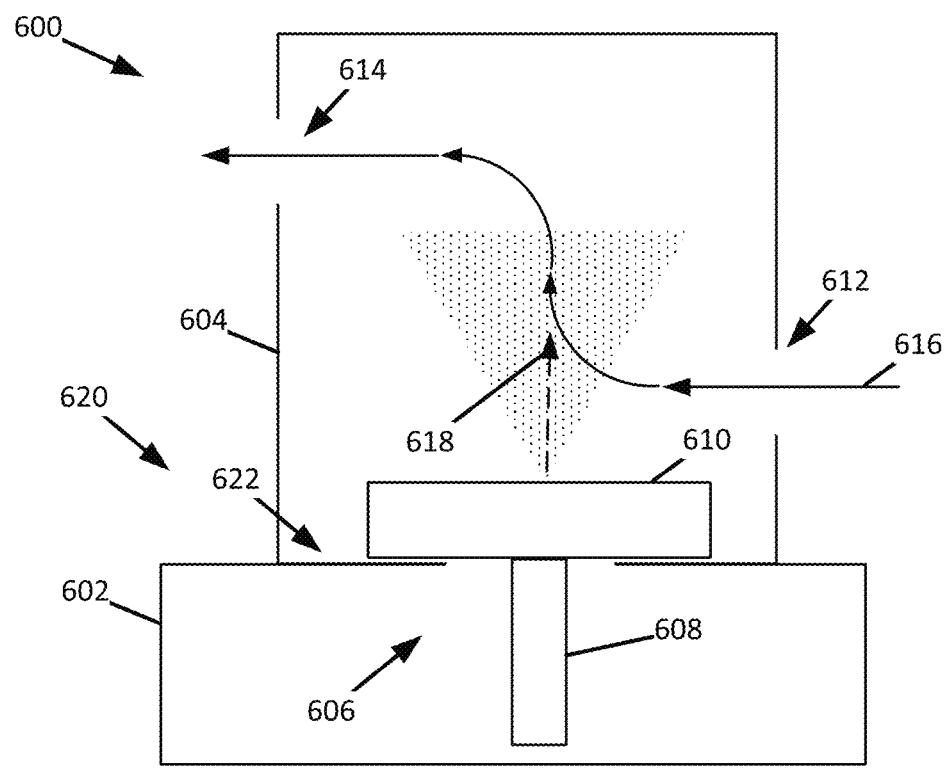
FIG. 6 shows a schematic example of a humidifier, consistent with embodiments of the present disclosure.

FIG. 6 shows a schematic example of a humidifier 600, which is an example of the humidifier 206 of FIG. 2. As shown, the humidifier 206 includes a liquid reservoir 602, a humidification chamber 604, and a humidity generator 606. The humidity generator 606 is configured to urge liquid from the liquid reservoir 602 and to disperse the liquid into the humidification chamber 604. For example, the humidity generator 606 may include a liquid collector 608 and a liquid disperser 610 (e.g., an atomizer, such as, a piezo-electric atomizer), the liquid collector 608 is configured to transfer fluid from the liquid reservoir 602 to the liquid disperser 610. The liquid collector 608 may be an active collector (e.g., include a pump) or a passive collector (e.g., include a wick). In some instances, the humidity generator 606 may be configured to generate droplets having a droplet size (e.g., an approximate diameter or a maximum dimension) in a range of about 1.5 microns to about 4.5 microns (e.g., droplets having a droplet size of about 2.5 microns). In some instances, at least a portion of the humidity generator 606 (e.g., the liquid disperser 610) may be at a bottom portion 620 (e.g., coupled at a bottom wall 622) of the humidification chamber 604.

The humidity generator 606 may include one or more of an atomizer (e.g., a piezo-electric atomizer, a nozzle atomizer, an electrostatic atomizer, a centrifugal atomizer, and/or any other type of atomizer), a heat source (e.g., a boiler to generate steam), a passive evaporator, an ozone bubbler within a liquid bath, a mister, a sprayer, a humidity pack, and/or the like to generate humidity within the humidification chamber 604. In some instances, one or more components of the humidity generator 606 may include a protective (e.g., hydrophobic) coating on at least a portion of the component.

The humidification chamber 604 includes a humidification chamber ozone inlet 612 through which air (e.g., ozonated air) enters the humidification chamber 604 and a humidification chamber outlet 614 through which air (e.g., humidified ozonated air or ozonated air) exits the humidification chamber 604 (e.g., to pass into the CPAP hose 312). The humidification chamber ozone inlet 612 and the humidification chamber outlet 614 are arranged such that a humidifier flow path 616 (which forms a portion of the flow path 220, FIG. 2) extends transverse to (e.g., perpendicular to) an emission axis 618 of the humidity generator 606. In some instances, air flowing along the humidifier flow path 616 may be turbulent for at least a portion of the humidifier flow path 616 (the turbulence may improve mixing of ozone with atomized liquid). For example, a turbulent flow of air may be present at the humidification chamber ozone inlet 612 and may transition to a laminar flow (e.g., after passing through the humidification chamber outlet 614 and into the CPAP hose 312). In some instances, the humidifier 600 may generally be described as being configured to encourage a mixing of ozone with humidity (e.g., within the humidification chamber 604).

Figure 7:
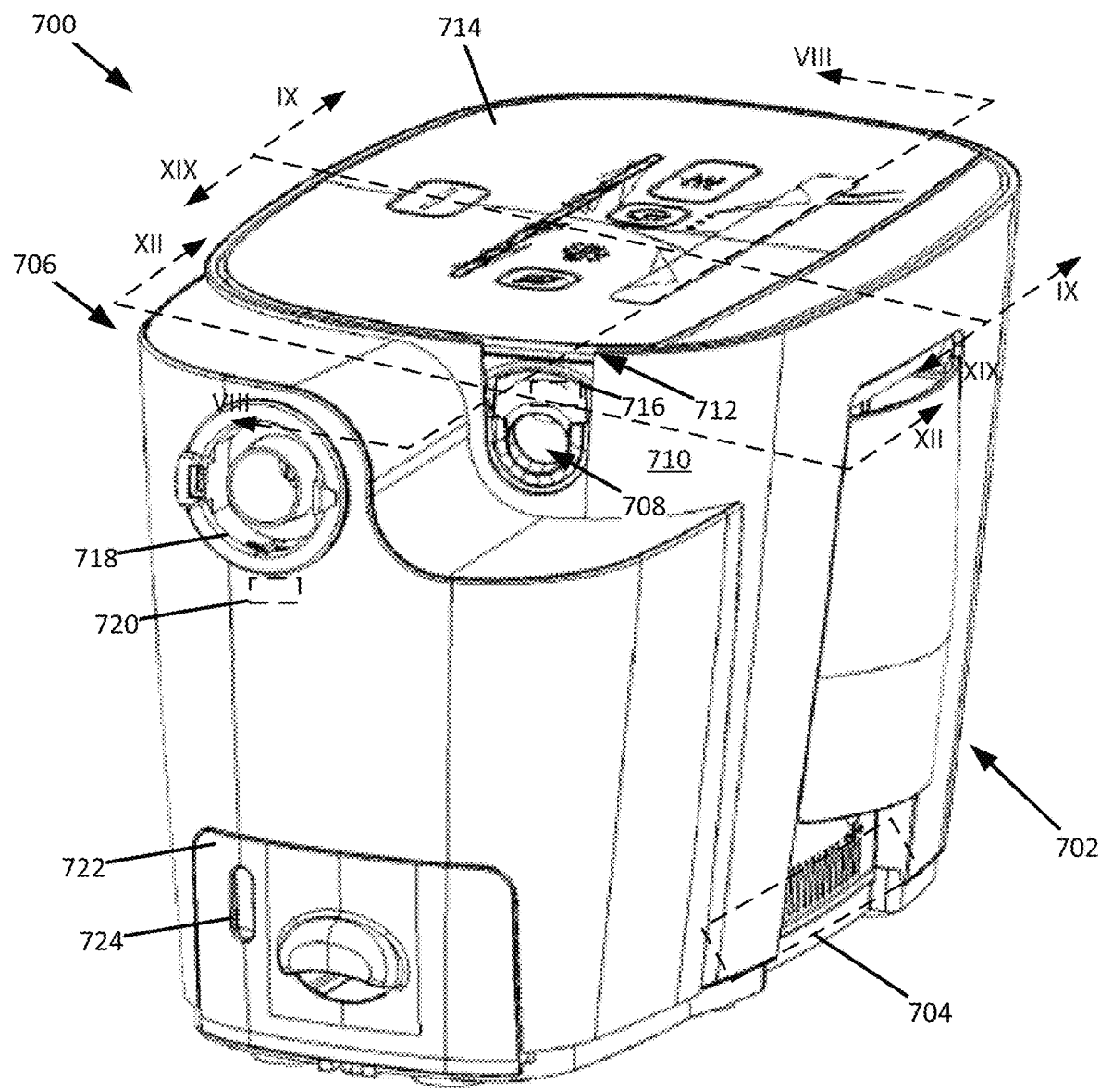
FIG. 7 shows a perspective view of a disinfection device, consistent with embodiments of the present disclosure.

FIG. 7 shows an example of a disinfection device 700 with humidity control configured to disinfect one or more components of a continuous positive air pressure (CPAP) machine. The disinfection device 700 is an example of the disinfection device 300 of FIG. 3.

Figure 7A:
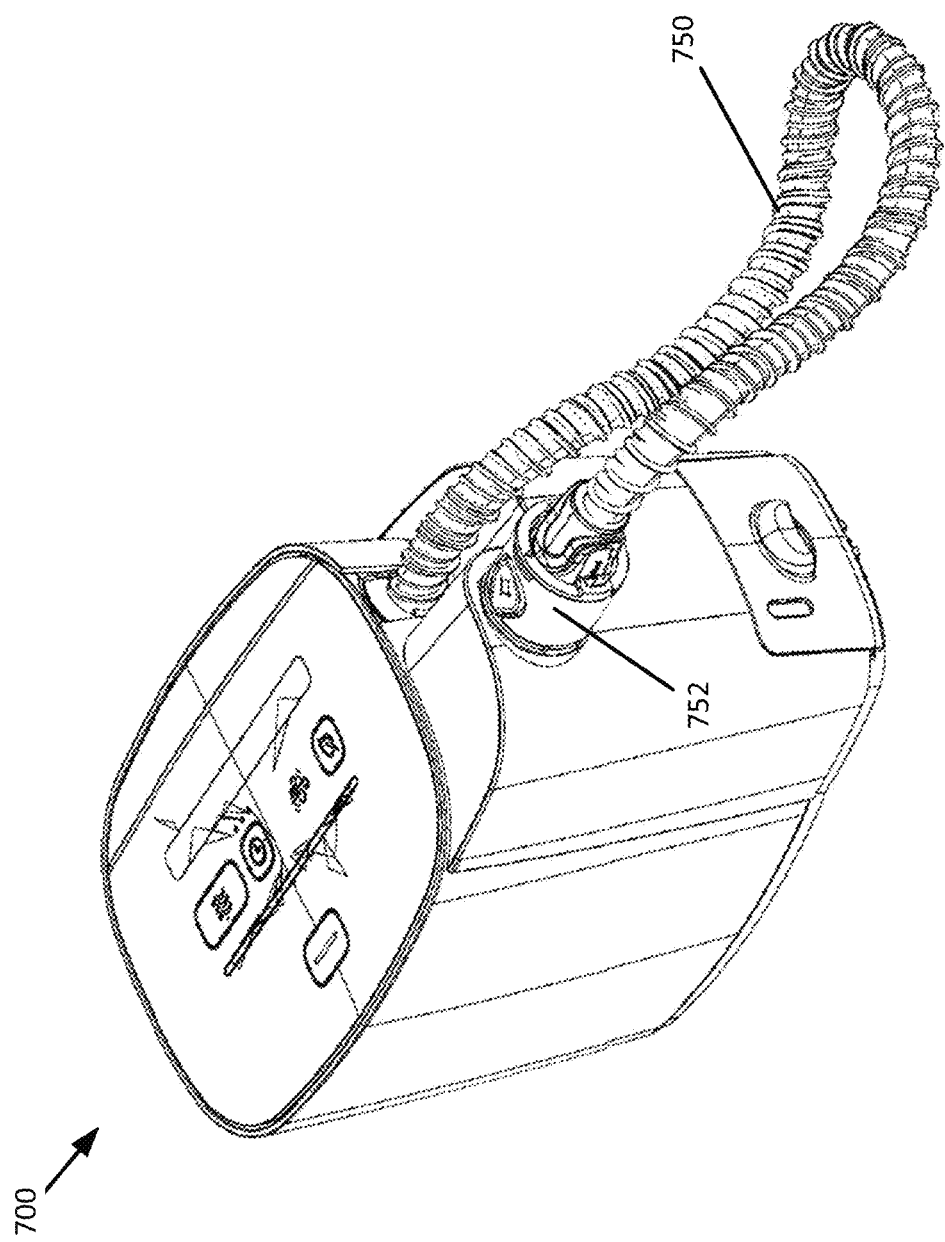
FIG. 7A shows a perspective view of the disinfection device of FIG. 7 having a CPAP hose coupled thereto, consistent with embodiments of the present disclosure.
Figure 7B:
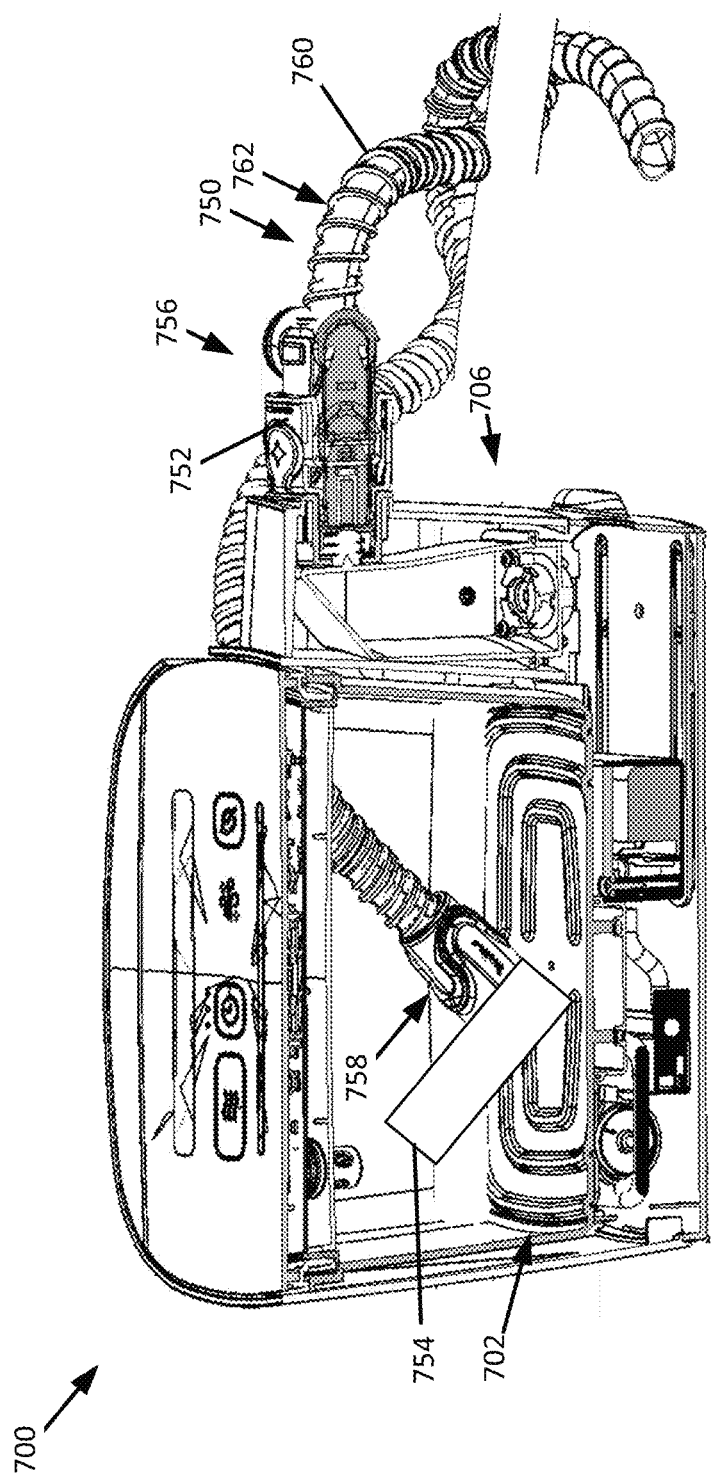
FIG. 7B shows a cross-sectional perspective view of the disinfection device of FIG. 7A, consistent with embodiments of the present disclosure.

As shown, the disinfection device 700 includes a disinfection chamber 702, an ozone generation assembly 704 (shown schematically in hidden lines), and a humidifier assembly 706. The disinfection chamber 702 includes a CPAP hose passthrough 708 through which a CPAP hose 750 (see, FIG. 7A) can be inserted such that at least a portion of the CPAP hose 750 is received within the disinfection chamber 702. In other words, the CPAP hose passthrough 708 is configured such that the CPAP hose 750 can pass therethrough. As shown in FIG. 7B, the CPAP hose 750 has a first hose end 756 and a second hose end 758, wherein a CPAP hose adapter 752 is disposed at the first hose end 756 and a CPAP mask 754 is disposed at the second hose end 758 (e.g., removably coupled to a connection point at the second hose end 758). As such, the CPAP hose 750 may generally be described as being fluidly coupled to the humidifier assembly 706 as the first hose end 756 and the humidifier assembly 706 may generally be described as being fluidly coupled to the disinfection chamber 702 via the CPAP hose 750 and CPAP mask 754. As also shown, the CPAP hose 750 includes a helical rib 760 that extends at least a substantial length of the CPAP hose 750 and forms one or more crevices 762 (e.g., a helical groove that extends for at least a length of the helical rib 760). In addition, the length of the CPAP hose 750 may pose one or more challenges to disinfection performance. As such, pathogens may tend to collect at the one or more crevices 762 and/or along a length of the CPAP hose 750. The CPAP mask 754 may include one or more features worn by a user (e.g., one or more nasal passages) that may also tend to collect one or more pathogens with use.

The CPAP hose passthrough 708 may be at least partially formed within a sidewall 710 of the disinfection chamber 702. In some instances, the CPAP hose passthrough 708 may include a passthrough open end 712. The passthrough open end 712 may be selectively closed by a disinfection chamber lid 714. In these instances, the CPAP hose passthrough 708 and the disinfection chamber lid 714 may cooperate to form a seal that extends about the CPAP hose 750. The seal may be configured to mitigate and/or prevent ozone from escaping from the disinfection chamber 702 at the CPAP hose passthrough 708. In some instances, the CPAP hose passthrough 708 may include a first hose sensor 716 (shown schematically in hidden lines) configured to detect a presence of the CPAP hose 750 within the CPAP hose passthrough 708. The first hose sensor 716 may be configured to prevent generation of ozone when the CPAP hose 750 is not received within the CPAP hose passthrough 708.

The humidifier assembly 706 includes a CPAP hose coupling 718 for removably coupling to the CPAP hose. As such, the CPAP hose fluidly couples the humidifier assembly 706 to the disinfection chamber 702. The CPAP hose coupling 718 may be configured to detect when a CPAP hose is coupled thereto. For example, the CPAP hose coupling 718 may include a second hose sensor 720 (shown schematically in hidden lines). The second hose sensor 720 may be configured to detect a presence of the CPAP hose 750 coupled thereto. In some instances, the CPAP hose 750 may be coupled to the CPAP hose coupling 718 using a CPAP hose adapter 752 (FIG. 7A) and the second hose sensor 720 may be configured to detect the presence of the CPAP hose 750 and/or the CPAP hose adapter 752. The second hose sensor 720 may be configured to prevent generation of ozone when the CPAP hose 750 is not coupled thereto.

The humidifier assembly 706 further includes a liquid reservoir access 722. The liquid reservoir access 722 is configured to allow a user to selectively replenish a liquid in the humidifier assembly 706. The liquid reservoir access 722 may be configured as a door, a drawer, and/or any other form of access. In some instances, the liquid reservoir access 722 may include a liquid level window 724 configured to enable a user to observe a quantity of liquid within a liquid reservoir.

Figure 8:
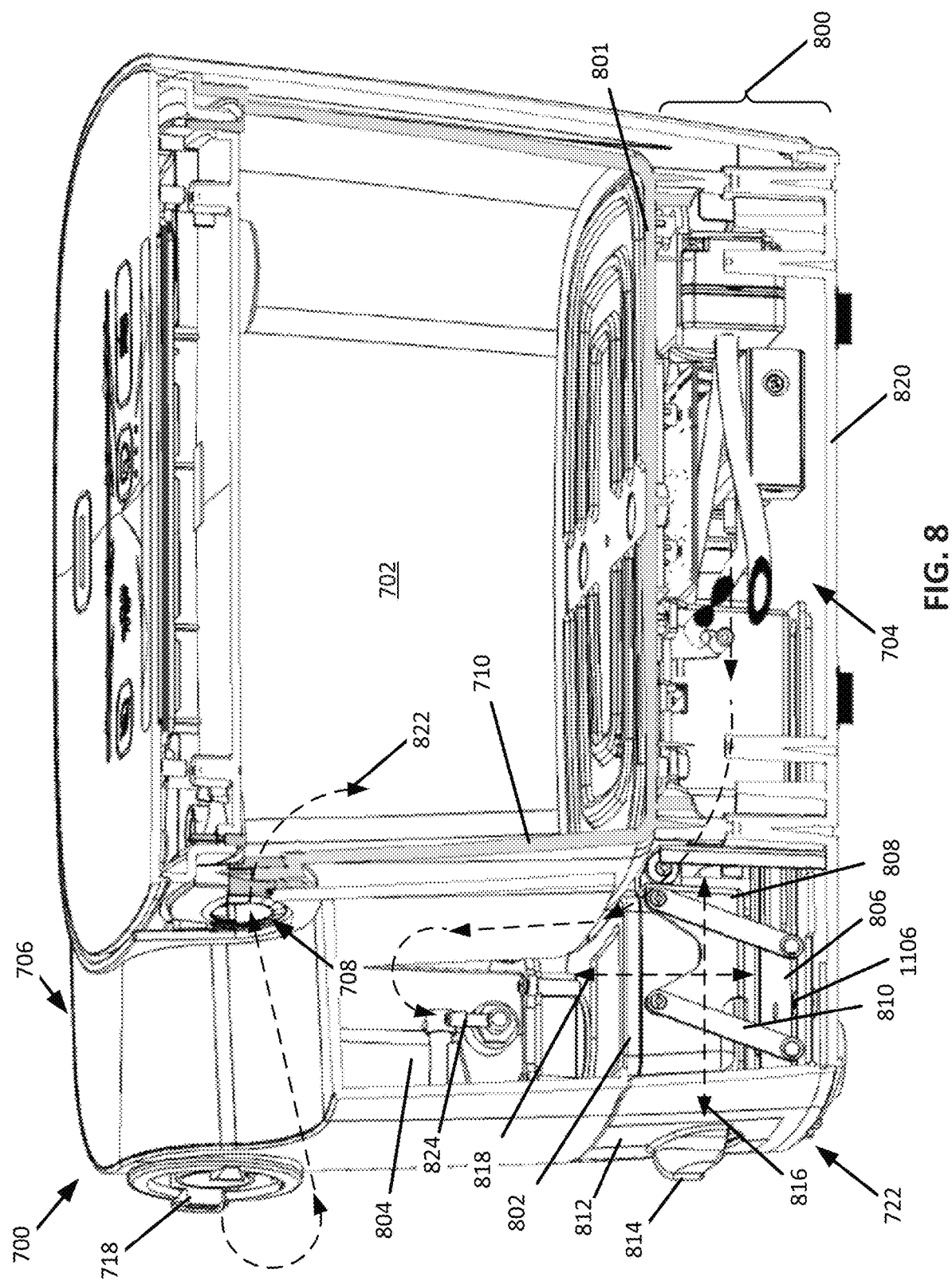
FIG. 8 shows a cross-sectional view of the disinfection device of FIG. 7 taken along the line VIII-VIII of FIG. 7, consistent with embodiments of the present disclosure.
Figure 9:
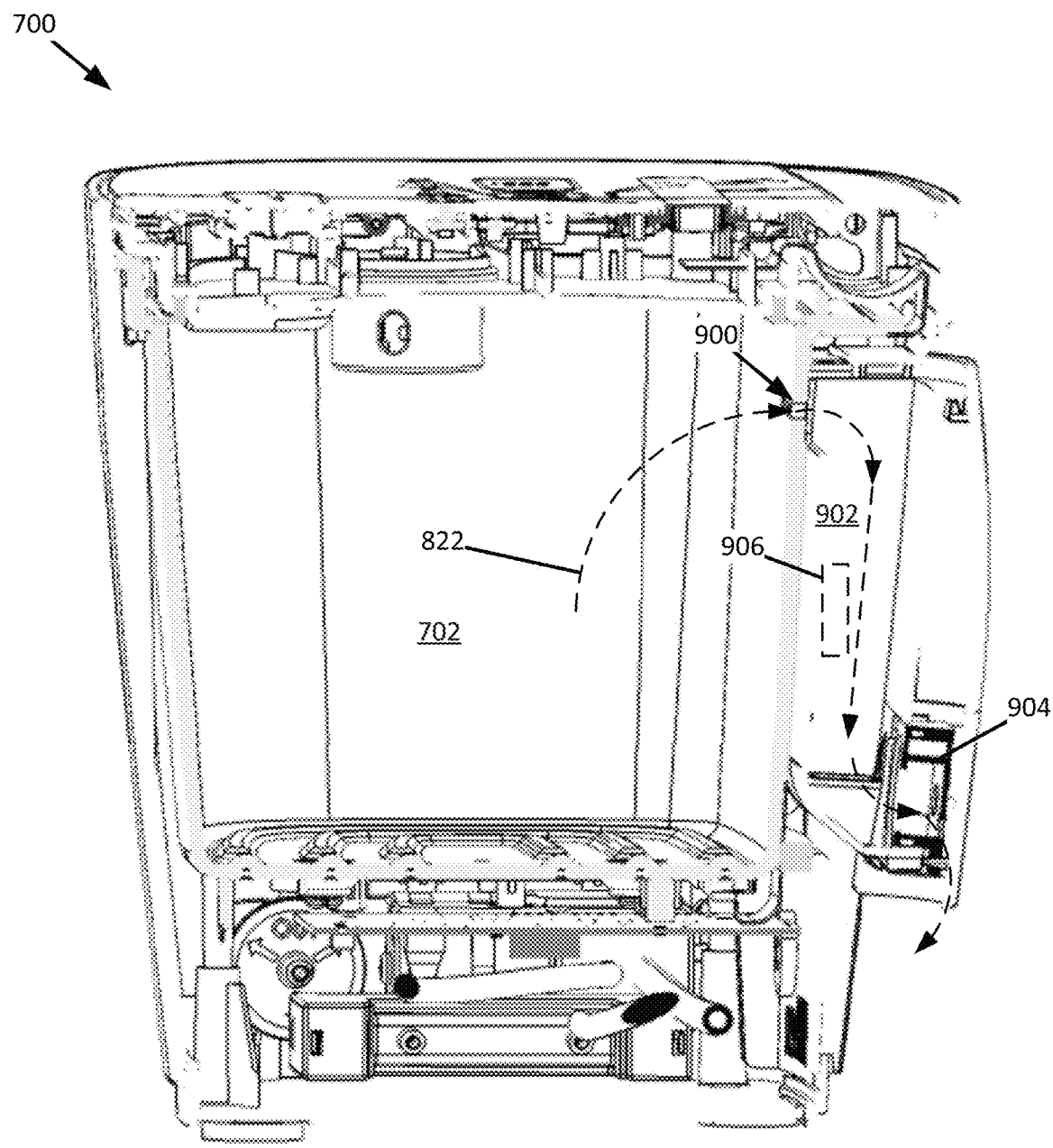
FIG. 9 shows a cross-sectional view of the disinfection device of FIG. 7 taken along the line IX-IX of FIG. 7, consistent with embodiments of the present disclosure.

FIG. 8 shows a cross-sectional view of the disinfection device 700 taken along the line VIII-VIII of FIG. 7 and FIG. 9 shows a cross-sectional view of the disinfection device 700 taken along the line IX-IX of FIG. 7. As shown, the ozone generation assembly 704 is disposed within a base region 800 of the disinfection device 700. At least a portion of the base region 800 is disposed beneath the disinfection chamber 702. For example, a base sidewall 801 that defines at least a portion of the disinfection chamber 702 may extend between the disinfection chamber 702 and the ozone generation assembly 704, separating the ozone generation assembly 704 from the disinfection chamber 702.

As also shown, at least a portion of the humidifier assembly 706 extends within the base region 800 and along at least a portion of the disinfection chamber 702 (e.g., an external surface of the sidewall 710 of the disinfection chamber 702). For example, the humidifier assembly 706 may include a liquid reservoir 802 and a humidification chamber 804, wherein at least a portion of the liquid reservoir 802 extends within the base region 800 and at least a portion of the humidification chamber 804 extends along the disinfection chamber 702 and above the base region 800.

The liquid reservoir access 722 includes a movable platform 806, a carriage 808 configured to removably receive the liquid reservoir 802, one or more linkages 810 pivotally coupled to the movable platform 806 and the carriage 808, and an access door 812 including a handle 814 coupled to the movable platform 806. In use, a user exerts a force (e.g., a pulling or pushing force) on the handle 814 to transition the movable platform 806 from a use position to a refill position. When transitioning between the use and refill positions, the movable platform 806 may be caused to slide along an insertion axis 816. When the movable platform 806 transitions between the use and refill positions, the one or more linkages 810 pivot relative to the movable platform 806 and the carriage 808 such that the carriage 808 (and the liquid reservoir 802) are caused to move along the insertion axis 816 and a coupling axis 818. The insertion axis 816 extends transverse to (e.g., perpendicular to) the coupling axis 818. As shown, the insertion axis 816 extends generally (e.g., within 1°, 2°, 3°, 4°, or 5° of) parallel to a base 820 of the disinfection device 700. In some instances, the insertion axis 816 may be described as a generally horizontal axis. As shown, the coupling axis 818 extends transverse to (e.g., perpendicular to) the base 820 of the disinfection device 700. In some instances, the coupling axis 818 may be described as a generally vertical axis.

As also shown in FIG. 8, a flow path 822 extends from the ozone generation assembly 704, into the humidification chamber 804 via an inlet connector 824, out of the humidification chamber 804 via the CPAP hose coupling 718, into the CPAP hose 750 that extends through the CPAP hose passthrough 708, and exits the CPAP hose 750 within the disinfection chamber 702 (e.g., and passes through a CPAP mask 754, see, FIG. 7B, disposed within the disinfection chamber 702). As shown in FIG. 9, the flow path 822 extends from the disinfection chamber 702 through a disinfection chamber outlet 900, into an ozone reduction filter 902, through an upstream fan 904, and into the surrounding environment. The upstream fan 904 is configured to draw air and/or ozone through the ozone reduction filter 902. In some instances, the ozone reduction filter 902 may include a filter communication system 906 configured to communicatively couple with the disinfection device 700 (e.g., to provide firmware updates, updated disinfection profiles, and/or the like). In some instances, the filter communication system 906 may be a radio frequency identification (RFID) tag.

Figure 9A:
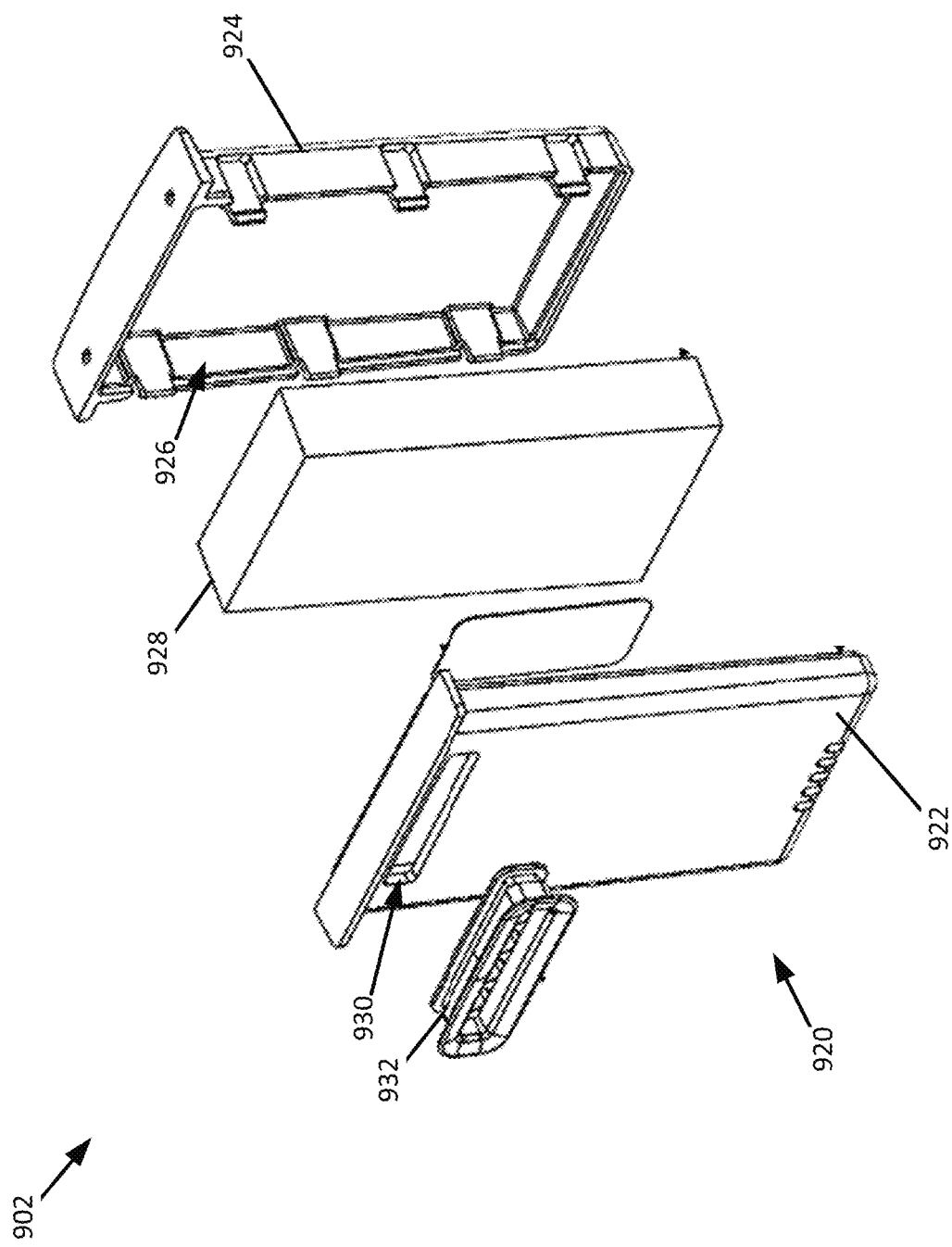
FIG. 9A is an exploded view of an example of an ozone reduction filter, consistent with embodiments of the present disclosure.

FIG. 9A shows an exploded view of the ozone reduction filter 902. As shown, the ozone reduction filter 902 includes a housing 920 having an upstream housing portion 922 and a downstream housing portion 924, wherein the upstream housing portion 922 and the downstream housing portion 924 define a filter cavity 926 configured to receive a filter medium 928 configured to reduce ozone. The upstream housing portion 922 includes an ozonated air inlet 930. The ozonated air inlet 930 may include a filter seal 932 for sealingly engaging with the disinfection chamber outlet 900 (FIG. 9). As shown, the filter communication system 906 is disposed within the filter cavity 926 at a location between the filter medium 928 and the upstream housing portion 922.

Figure 10:
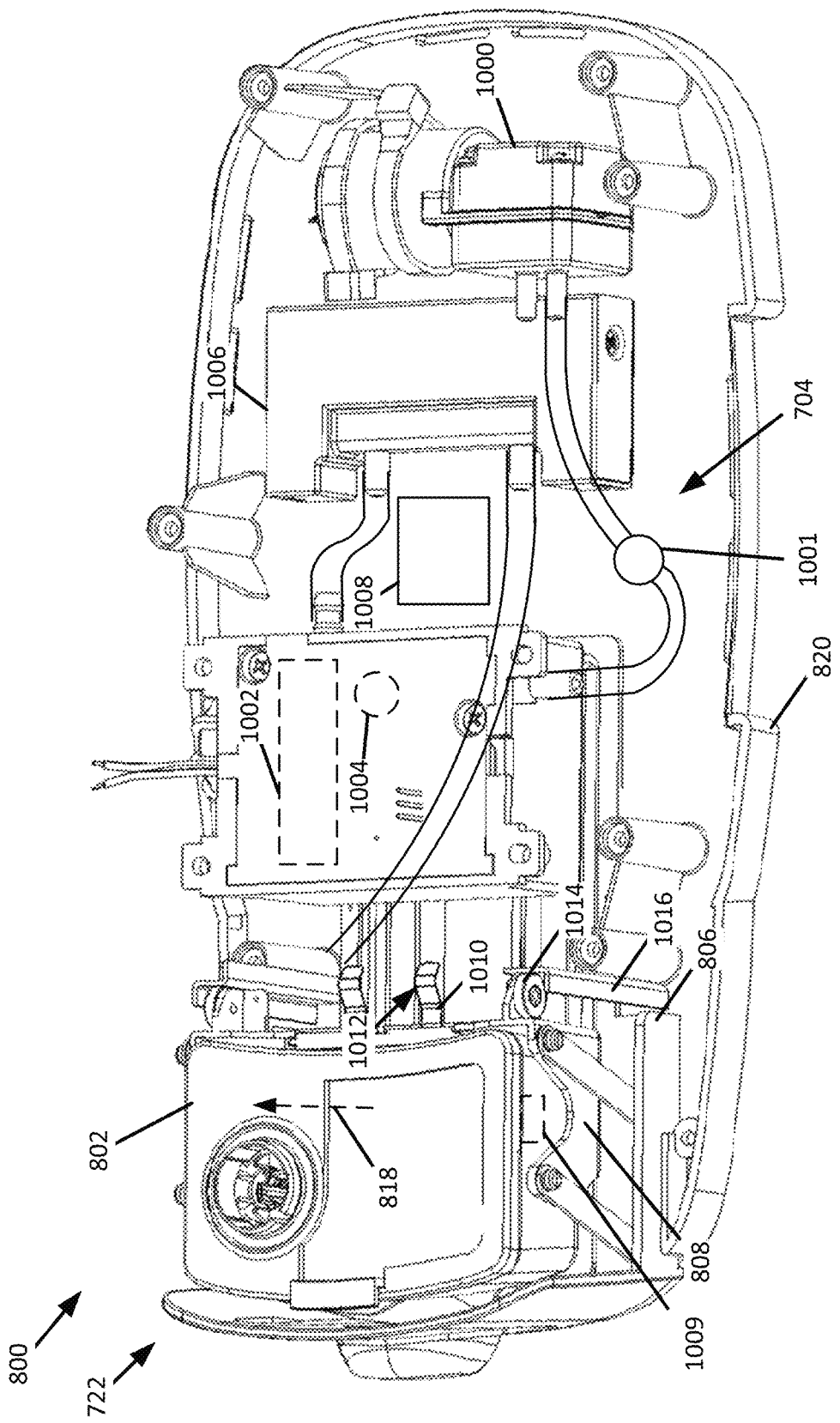
FIG. 10 shows a perspective view of a base region of the disinfection device of FIG. 7, consistent with embodiments of the present disclosure.

FIG. 10 shows a perspective view of the base region 800 of the disinfection device 700. As shown, the base region 800 includes a pump 1000 fluidly coupled to the ozone generation assembly 704. In some instances, a back flow preventer 1001 (e.g., a check-valve or Polytetrafluoroethylene (PTFE) filter) may be disposed downstream of the pump 1000 and/or downstream of the ozone generation assembly 704, which may reduce or prevent water (e.g., ozonated water) from flowing into the pump 1000 and/or the ozone generation assembly 704.

In operation, the pump 1000 is configured to cause air from a surrounding environment to flow through the ozone generation assembly 704 to create ozonated air. The environmental air has pre-existing conditions (e.g., relative humidity and/or any other pre-existing condition). The pre-existing conditions of the environmental air may influence the performance of the ozone generation assembly 704. As such, the disinfection device 700 may, in some instances, include one or more environmental sensors (e.g., a relative humidity sensor) to sense one or more environmental conditions (e.g., a relative humidity) and to adjust the ozone generation assembly 704 based, at least in part, on at least one of the sensed environmental conditions. Operation of the ozone generation assembly 704 based, at least in part, on sensed environmental conditions may encourage more efficient and/or consistent operation of the ozone generation assembly 704.

As shown, the ozone generation assembly 704 includes an ozone source 1002 (shown schematically in hidden lines), a relative humidity sensor 1004 (shown schematically in hidden lines), and an ozone sensor 1006. The relative humidity sensor 1004 is configured to detect a relative humidity of the environmental air. The detected relative humidity is provided to a controller 1008. The controller 1008 is configured to cause the ozone source 1002 to operate according to operation parameter(s) that are based, at least in part, on the detected relative humidity. The operation parameter(s) are configured to cause the ozone source 1002 to generate an estimated quantity of ozone. However, the estimated quantity of ozone to be generated may be different from an actual quantity of ozone generated. The ozone sensor 1006 is configured to detect the actual quantity of ozone generated by the ozone source 1002. The detected quantity of ozone is provided to the controller 1008. The controller 1008 compares the detected quantity of ozone to the estimated quantity of ozone and adjusts the operation parameter(s) of the ozone source 1002 if the detected quantity of ozone is greater than or less than the estimated quantity of ozone or outside of an acceptable range (e.g., within 1%, 2%, 3%, 4%, 5%, 10%, 15%, or 20% of the estimated quantity of ozone). In other words, output from the relative humidity sensor 1004 is used to set initial operation parameter(s) of the ozone source 1002 and the ozone sensor 1006 is used to adjust the initial operation parameter(s) to meet an acceptable ozone threshold or range. Such a configuration may allow the ozone source to more quickly reach a desired quantity of ozone production (e.g., steady state). The desired quantity of ozone, as detected by the ozone sensor 1006, may be, for example, in a range of about 100 parts per million (ppm) to about 400 ppm. By way of further example, the desired quantity of ozone, as detected by the ozone sensor 1006, may be, about (e.g., within 1%, 2%, 3%, 4%, 5%, 10%, 15%, or 20% of) 270 ppm.

As shown, the liquid reservoir access 722 further includes a liquid level sensor 1009 configured to detect a level of liquid within the liquid reservoir 802. When the level of liquid falls below a predetermined threshold (e.g., the liquid reservoir 802 is substantially empty or has insufficient liquid to complete a disinfection cycle) operation of the disinfection device 700 may be prevented. The liquid level sensor 1009 may include one or one or more arms 1010. The one or more arms 1010 include a raised region 1012 configured to engage (e.g., contact) a portion of disinfection device 700 (e.g., one or more electrical contacts to form an electrical connection with the controller 1008).

As also shown, the liquid reservoir access 722 may also include at least one wheel 1014 coupled to the carriage 808. The at least one wheel 1014 is configured to engage a corresponding track 1016 extending from the base 820. Engagement between the at least one wheel 1014 and the track 1016 may encourage the movement of the carriage along the coupling axis 818.

Figure 11:
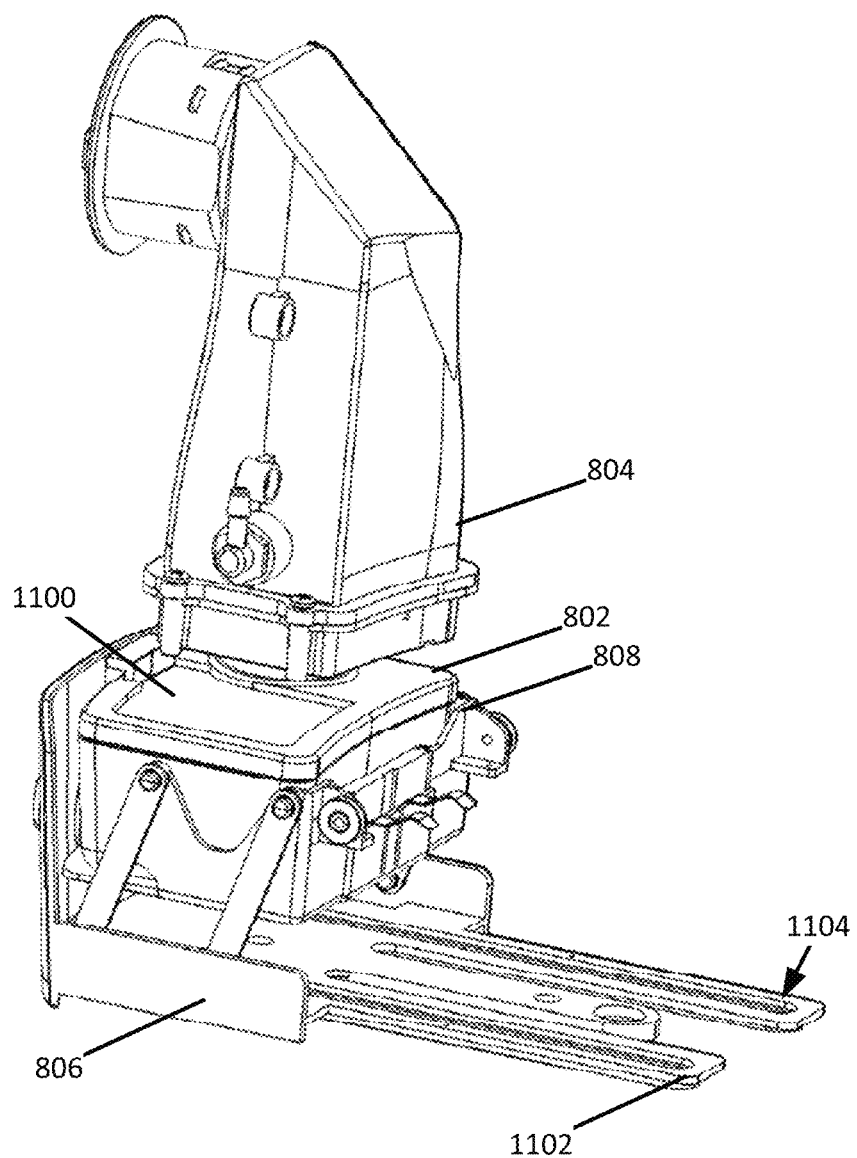
FIG. 11 shows a perspective view of a portion of a humidifier assembly of the disinfection device of FIG. 7, consistent with embodiments of the present disclosure.
Figure 11A:
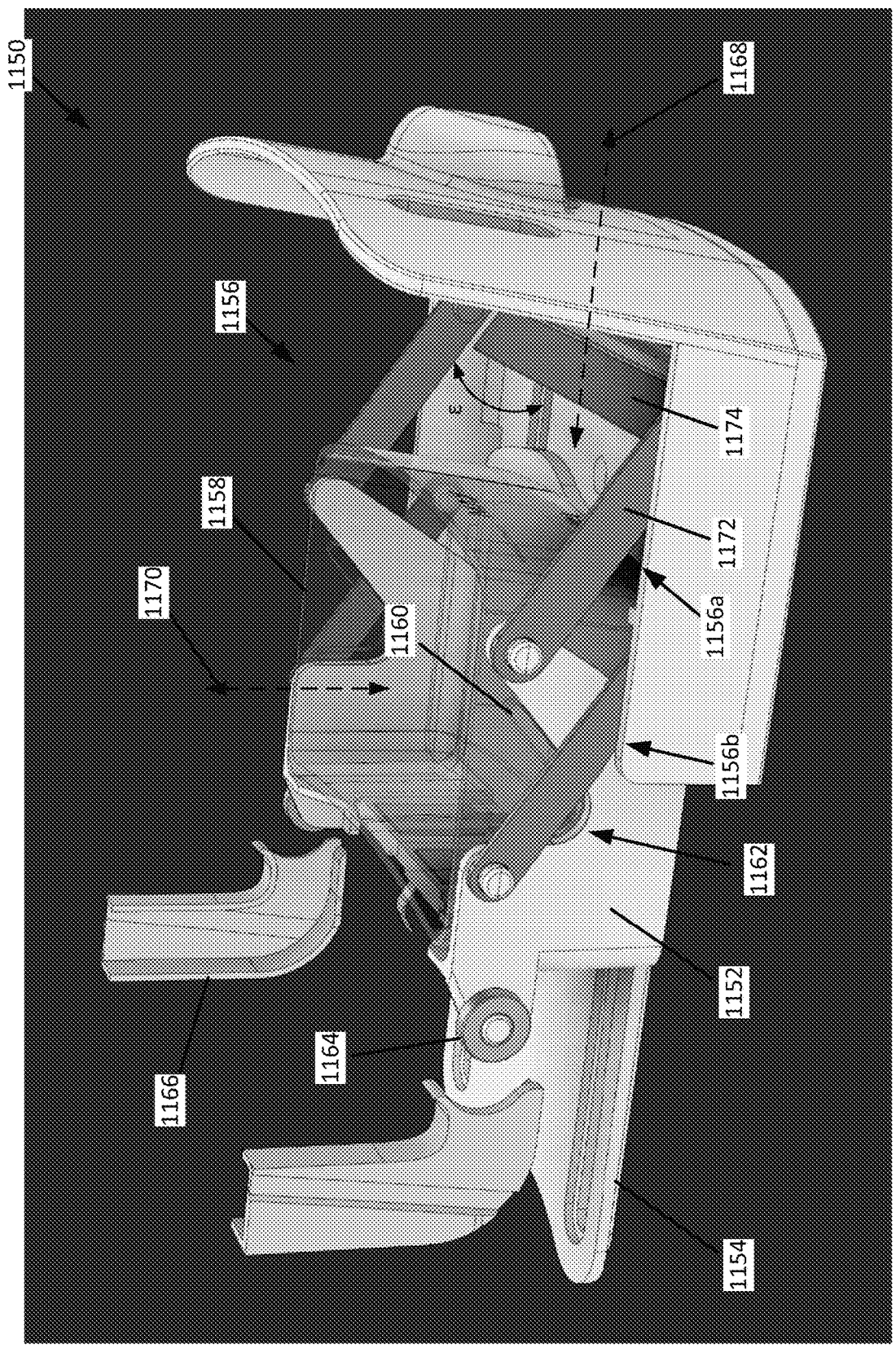
FIG. 11A shows a perspective view of a liquid reservoir access, consistent with embodiments of the present disclosure.
Figure 11B:
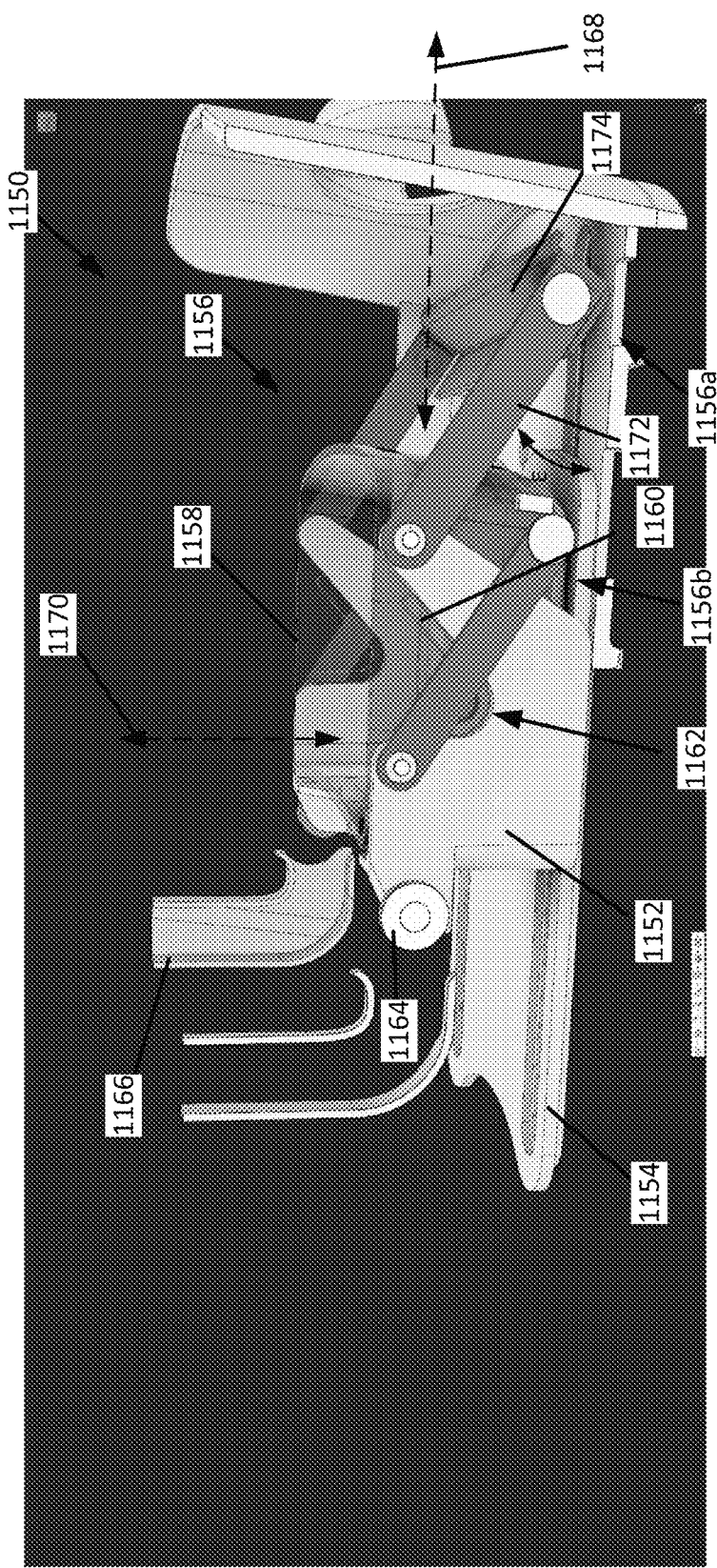
FIG. 11B shows a perspective cross-sectional view of the liquid reservoir access of FIG. 11A, consistent with embodiments of the present disclosure.
Figure 11C:
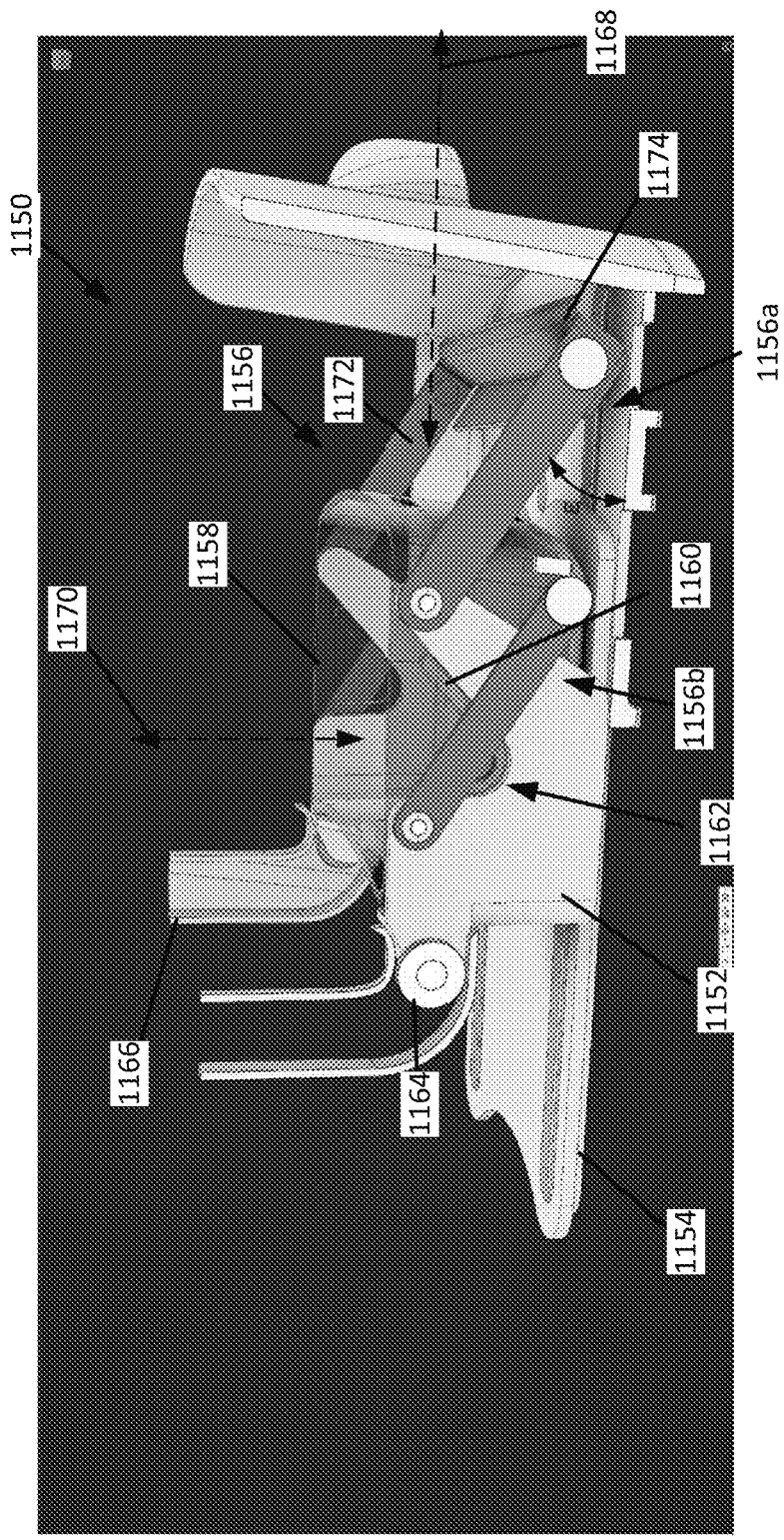
FIG. 11C shows another cross-sectional perspective view of the liquid reservoir access of FIG. 11A, consistent with embodiments of the present disclosure.
Figure 11D:
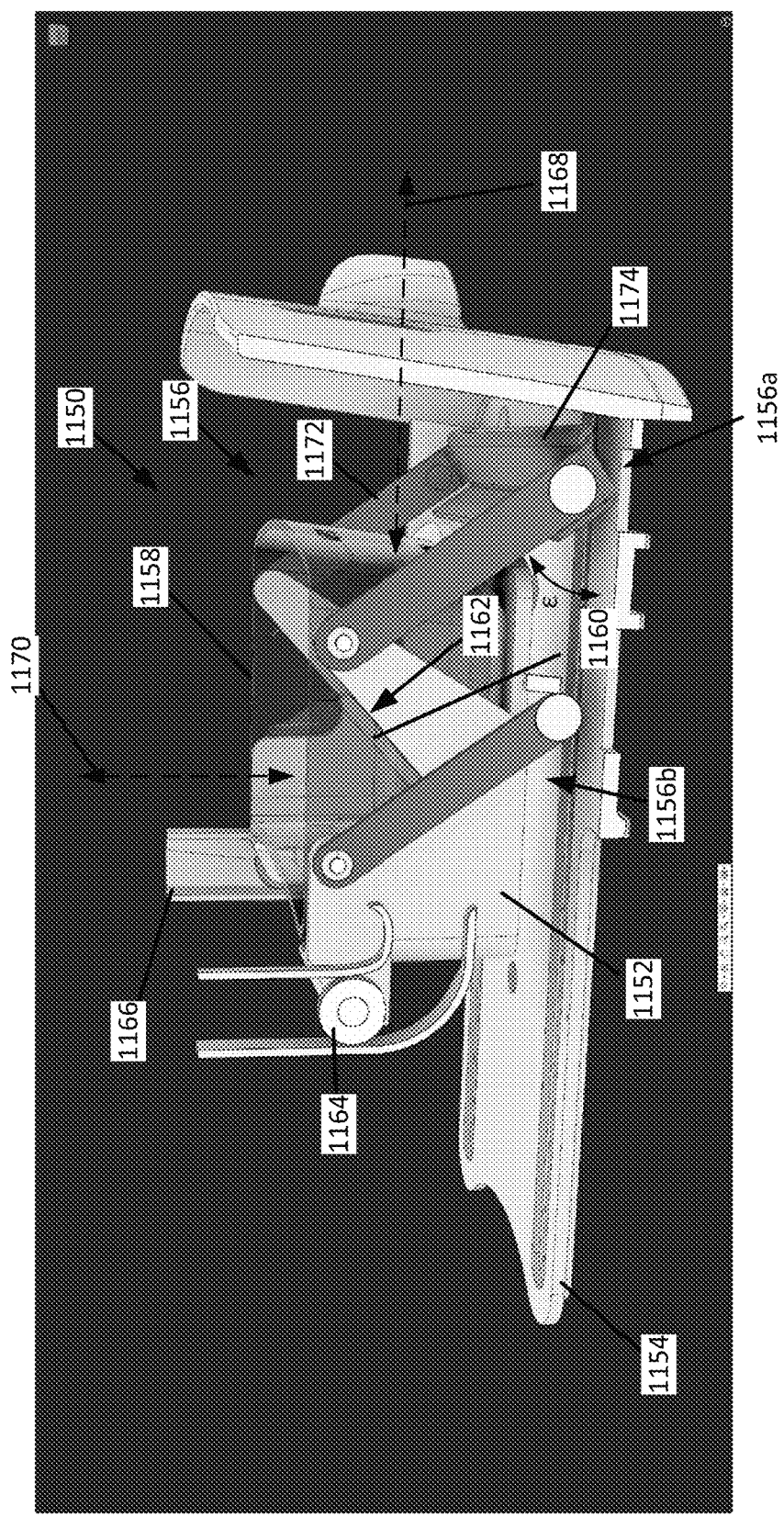
FIG. 11D shows another cross-sectional perspective view of the liquid reservoir access of FIG. 11A, consistent with embodiments of the present disclosure.

FIG. 11 shows a perspective view of the carriage 808 urging the liquid reservoir 802 into engagement with the humidification chamber 804. As shown, the liquid reservoir 802 includes an openable refill lid 1100 configured to be transitioned between an open position and a closed position. In some instances, the openable refill lid 1100 may be configured to be automatically opened as the movable platform 806 is transitioned from a use position to a refill position. Additionally, or alternatively, the openable refill lid 1100 may be opened by a user. As also shown, the movable platform 806 includes tracks 1102 including slots 1104 configured to slidably receive a guiding protrusion 1106 (FIG. 8) of the disinfection device 700.

FIGS. 11A-11E show another example of a liquid reservoir access 1150, which is an example of the liquid reservoir access 722. The liquid reservoir access 1150 includes a carriage 1152, a movable platform 1154, and a plurality of linkages 1156 pivotally coupled to the carriage 1152 and the platform 1154. The carriage 1152 is configured to receive a liquid reservoir 1158 which is an example of the liquid reservoir 802. As shown, the liquid reservoir 1158 includes a keying protrusion 1160 configured to cooperate with a keying receptacle 1162 of the carriage 1152. For example, the keying protrusion 1160 and the keying receptacle 1162 may be configured to cooperate to control an orientation of the liquid reservoir 1158 within the carriage 1152 (e.g., the liquid reservoir 1158 may be received within the carriage 1152 according to a single orientation). In this example, the keying protrusion 1160 and the keying receptacle 1162 may have corresponding shapes that are non-symmetrical along at least one axis.

Figure 11E:
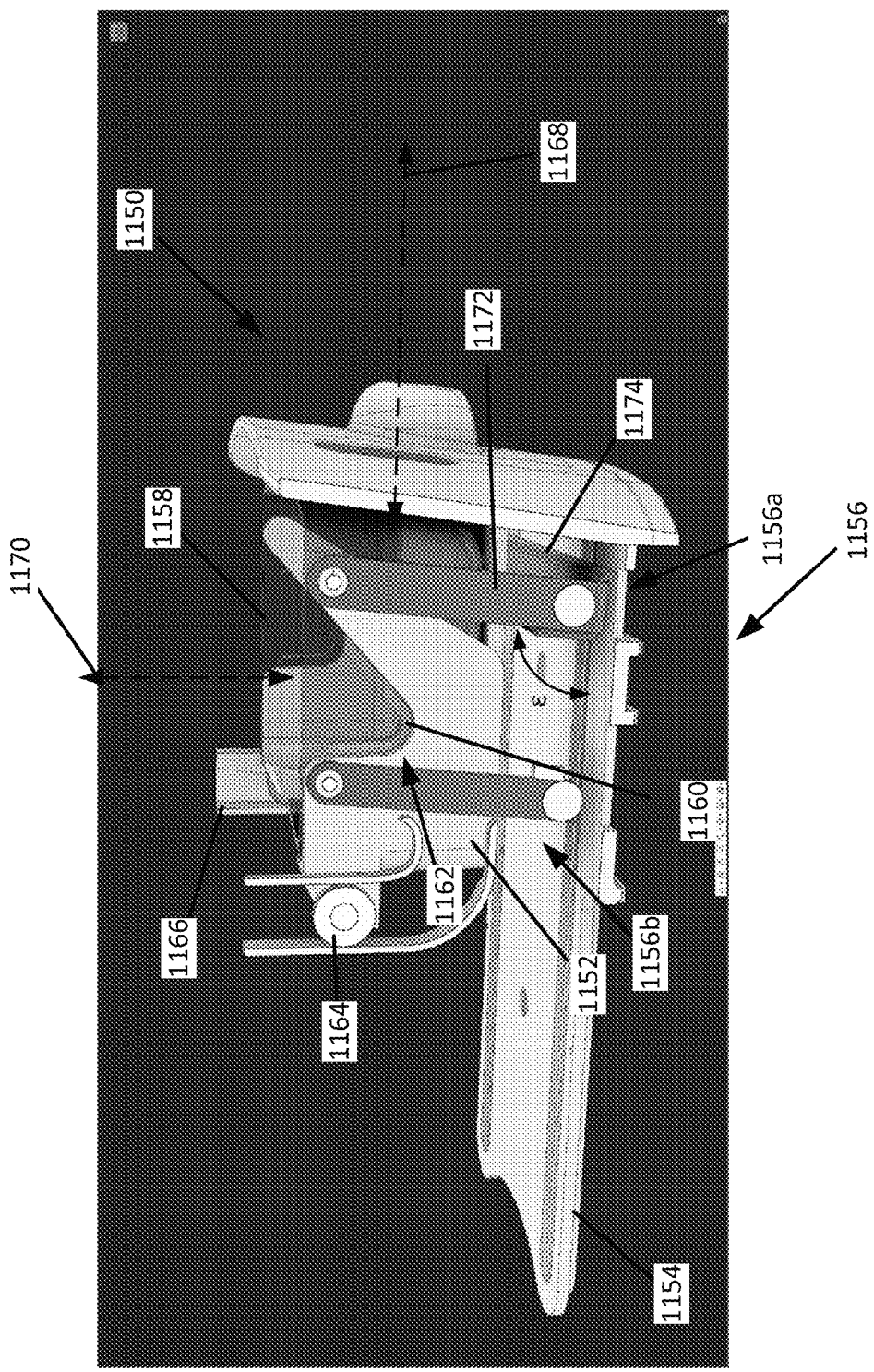
FIG. 11E shows another cross-sectional perspective view of the liquid reservoir access of FIG. 11A, consistent with embodiments of the present disclosure.

The carriage 1152 further includes wheels 1164 configured to engage with corresponding tracks 1166. As shown, as the carriage 1152 and the platform 1154 are moved along an insertion axis 1168, the wheels 1164 cooperate with the tracks 1166 to move the carriage 1152 to move towards or away from the platform 1154 and along a coupling axis 1170. As shown, as the carriage 1152 moves away from the platform 1154 a linkage angle &, which opens in a direction of the tracks 1166, increases to a fully inserted position (e.g., as shown in FIG. 11E). When at the fully inserted position the linkage angle & may be greater than or equal to 90°. Such a configuration may encourage the carriage 1152 and the platform 1154 to remain in the fully inserted position. When the linkage angle & is less than 90°, the carriage 1152 and platform 1154 may be encouraged to move along the insertion axis 1168 in a direction away from the fully inserted position (e.g., as a result of the weight of the liquid reservoir 1158).

As shown, the plurality of linkages 1156 include a forward linkage 1156a and a plurality of rearward linkages 1156b. The forward linkage 1156a may include a plurality of linkage arms 1172 connected together by a connection arm 1174. The connection arm 1174 may increase a twisting resistance of the forward linkage 1156a, which may improve alignment of the liquid reservoir 1158 relative to the humidification chamber 804.

Figure 11F:
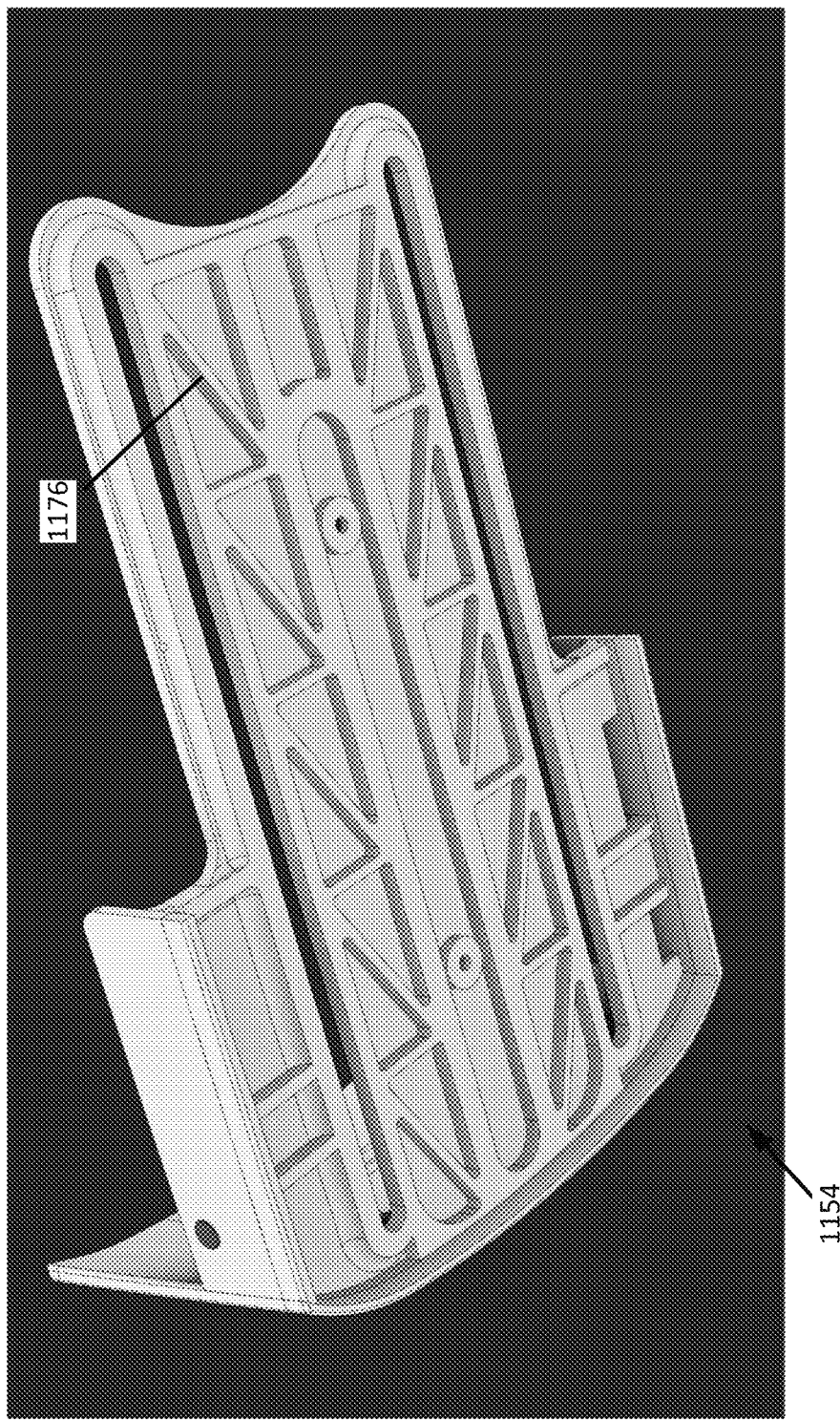
FIG. 11F shows a bottom view of a platform of the liquid reservoir access of FIG. 11A, consistent with embodiments of the present disclosure.

FIG. 11F shows a bottom view of the platform 1154. As shown, the platform 1154 includes one or more stiffening structures 1176 extending along the platform 1154. The one or more stiffening structures 1176 may increase torsional and/or linear stiffness.

Figure 12:
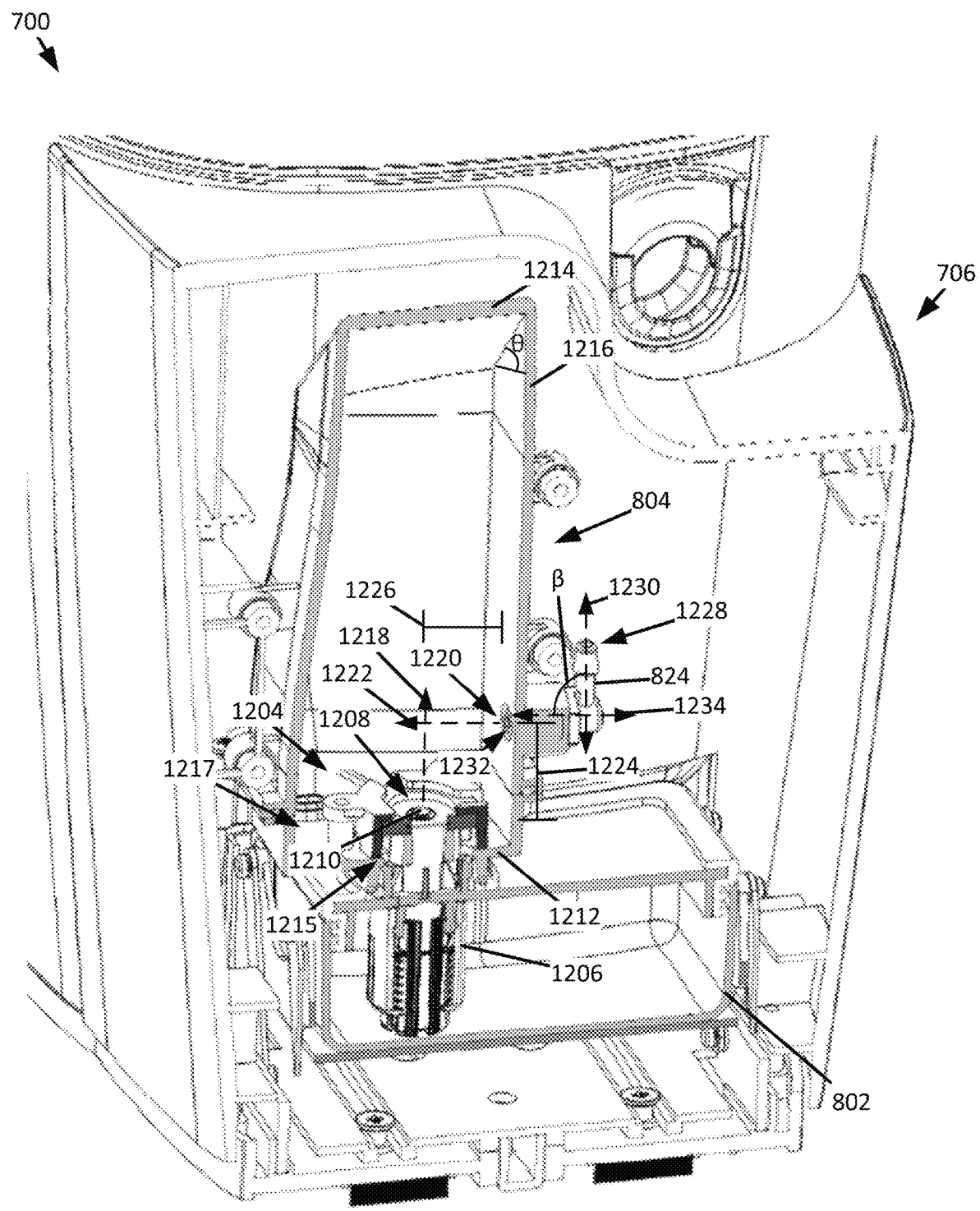
FIG. 12 shows a cross-sectional view of the disinfection device of FIG. 7 taken along the line XII-XII of FIG. 7, consistent with embodiments of the present disclosure.

FIG. 12 is a cross-sectional perspective view of a portion of the disinfection device 700 taken along the line XII-XII of FIG. 7 that illustrates the humidifier assembly 706. As shown, the humidifier assembly 706 includes the liquid reservoir 802, the humidification chamber 804, and a humidity generator 1204. The humidity generator 1204 is configured to draw liquid from the liquid reservoir 802 and disperse the liquid (e.g., as atomized droplets) into the humidification chamber 804.

The humidity generator 1204 may include, for example, a wick assembly 1206 configured to cooperate with an atomizer 1208 to transfer liquid from the liquid reservoir 802 to the humidification chamber 804. At least a portion of any ozone entering the humidification chamber 804 may become entrained within at least a portion of the liquid atomized by the atomizer 1208. The wick assembly 1206 is configured to draw liquid from the liquid reservoir 802 through capillary action and deliver the liquid to the atomizer 1208. The atomizer 1208 is configured to atomize delivered liquid into droplets that are dispersed within the humidification chamber 804. The atomizer 1208 may be a piezo-electric (or ultrasonic) atomizer that is configured to generate droplets of liquid (e.g., water) in a given quantity and size. In some instances, the atomizer 1208 may be configured as a reverse piezo-electric atomizer (e.g., a stainless steel plate of the atomizer 1208 is more exposed to the humidification chamber 804 than a piezo-electric ceramic of the atomizer 1208). For example, the atomizer 1208 may be piezo-electric atomizer having about (e.g., within 1%, 2%, 3%, 4%, 5%, 10%, or 15% of) 1,020 holes having a hole size of about (e.g., within 1%, 2%, 3%, 4%, 5%, 10%, or 15% of) 3.6 microns. By way of further example, the atomizer 1208 may be piezo-electric atomizer having about 1,320 holes having a hole size of about 4.3 microns. By way of further example, the atomizer 1208 may be piezo-electric atomizer having about 2,640 holes having a hole size of about 2.5 microns. The hole sizes of the piezo-electric atomizer may influence a droplet size that is formed and the quantity of holes may influence the quantity of droplets dispersed within the humidification chamber 804. In some instances, the hole sizes may be configured such that the smallest droplet has a size that does not result in Brownian motion. In some instances, the droplet size, of the most prevalent droplets, may be in a range of, for example, about 1.0 microns to about 3 microns. By way of further example, the droplet size, of the most prevalent droplets, may be in range of about 1.0 microns to about 5 microns. By way of still further example, the droplet size, of the most prevalent droplets, may be in range of about 1.5 microns to about 4.5 microns. By way of still further example, the droplet size, of the most prevalent droplets, may be about 2.5 microns. The piezo-electric atomizer may be an ultrasonic atomizer operated at about 110 kilohertz (kHz). In some instances, the piezo-electric atomizer 1208 may have a hole size of about 2.5 microns. In some instances, the disinfection device 700 may be configured such that the atomizer 1208 is caused to operate according to a self-clean cycle. In some instances, the controller 1008 may be configured to determine a status (e.g., functioning, damaged, and/or any other status) of the piezo-electric atomizer 1208 (e.g., by measuring a voltage across the piezo-electric atomizer 1208).

Figure 12A:
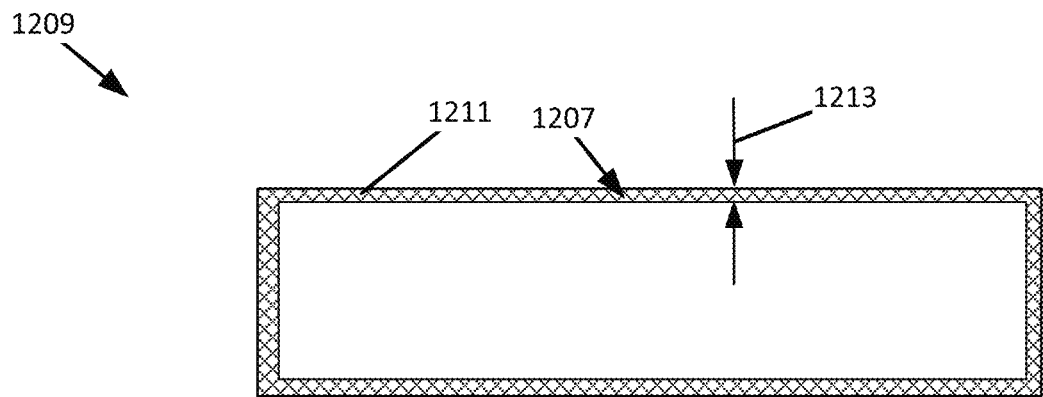
FIG. 12A shows a schematic example of an atomizer with a coating, consistent with embodiments of the present disclosure.
Figure 12D:
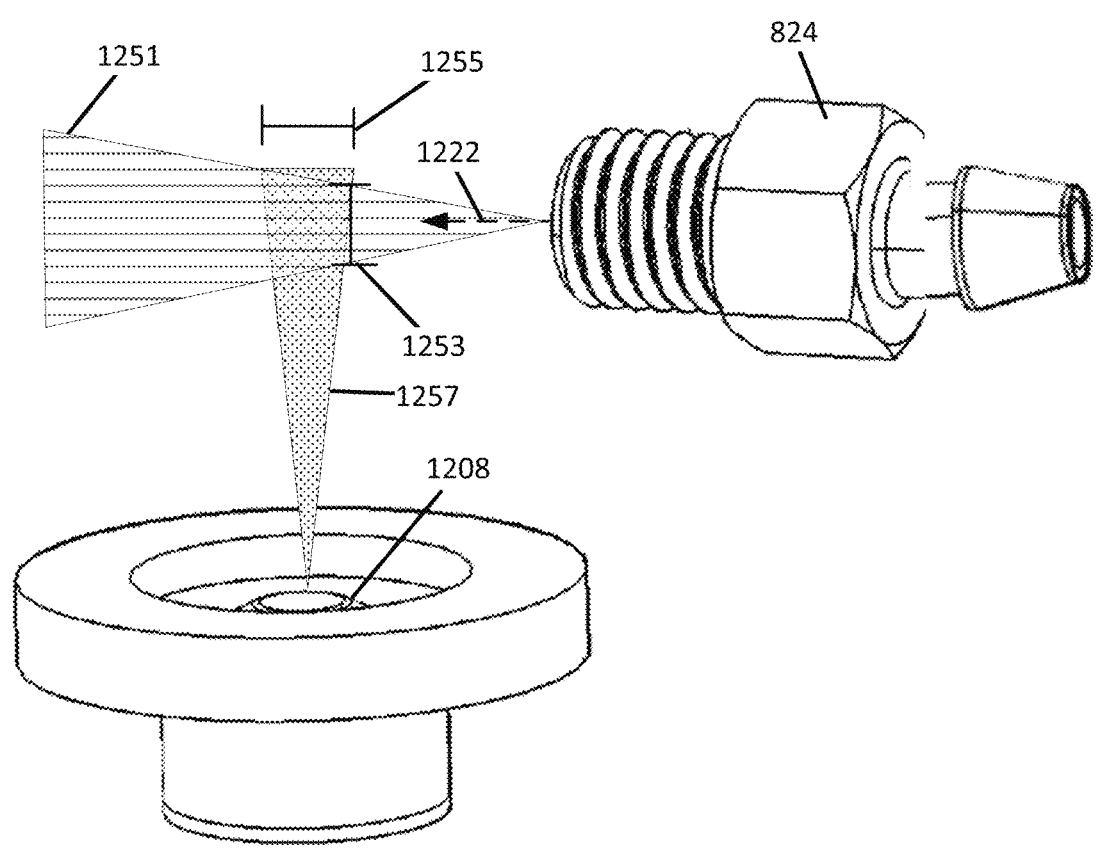
FIG. 12D shows an example of the humidification chamber ozone inlet including the insert of FIG. 12B, consistent with embodiments of the present disclosure.
Figure 12E:
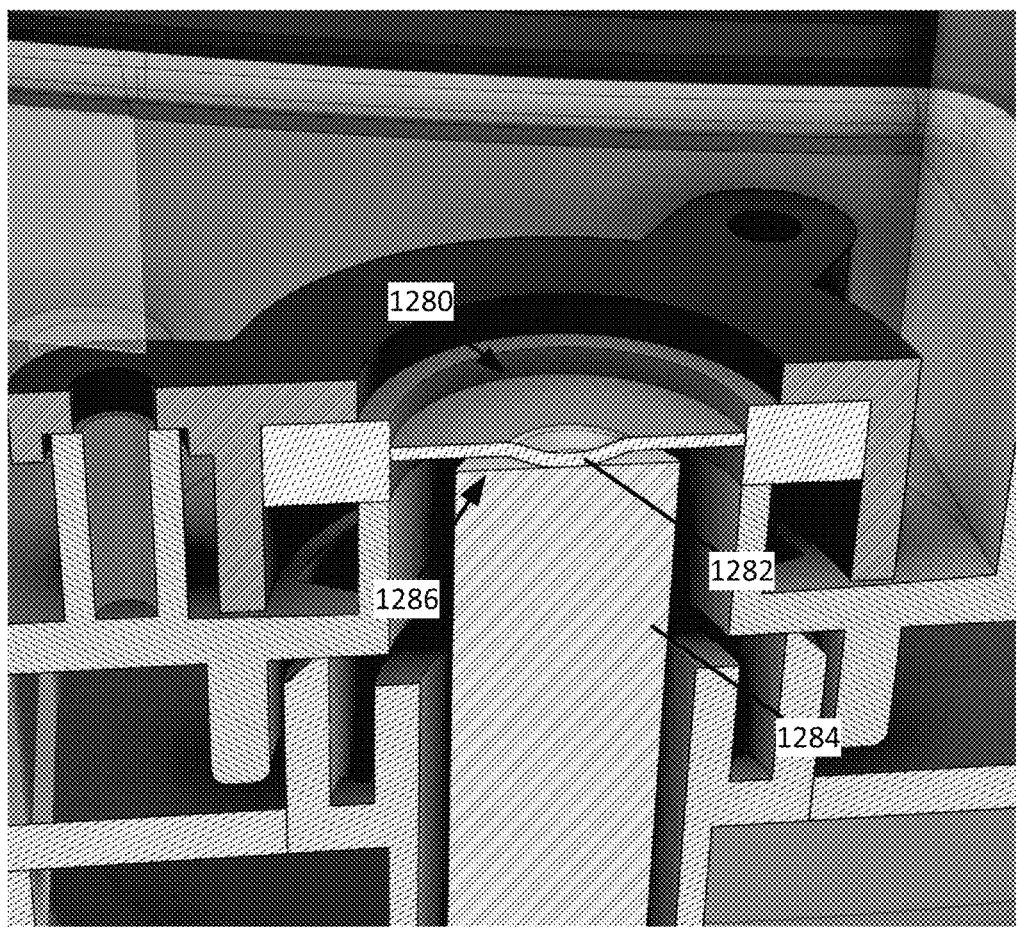
FIG. 12E shows a cross-sectional example of an atomizer having a recessed dimple configuration, consistent with embodiments of the present disclosure.

The atomizer 1208 may further include a dimple 1210 configured to engage at least a portion of the wick assembly 1206. The dimple 1210 can generally be described as a protruding dimple or a recessed dimple (see, e.g., FIG. 12E showing an atomizer 1280 having a recessed dimple 1282 engaging a wick 1284), wherein a protruding dimple protrudes into the humidification chamber 804 (as shown). With reference to FIG. 12E, the wick 1284 may have a substantially planar dimple engaging surface 1286 configured to cooperate with (e.g., engaging) the recessed dimple 1282. A more consistent engagement between the substantially planar dimple engaging surface 1286 may be obtained when using the recessed dimple 1282 when compared to the protruding dimple 1210, which may improve a longevity of the wick assembly 1206. For example, maintaining a substantially continuous force between the at least a portion of the wick 1284 (e.g., the substantially planar dimple engaging surface 1286) and the atomizer 1280 in a range of about 0.02 Newtons (N) to about 0.5 N may result in improved performance. By way of further example, a substantially continuous force between the at least a portion of the wick 1284 (e.g., the substantially planar dimple engaging surface 1286) and the atomizer 1280 in a range of about 0.05 N to about 0.25 N may result in improved performance.

The atomizer 1208 may be configured to operate for a period of at least about six months to at least about five years without failure within the environment of the disinfection device 700. One example of the atomizer 1208 may include a protective coating that is applied to one or more surfaces of the atomizer 1208. The protective coating may having a coating thickness in a range of, for example, about 2 microns to about 50 microns. By way of further example, the protective coating may having a coating thickness in a range of, for example, about 2 microns to about 12microns. The coating thickness may be determined based, at least in part, on the properties of the coating and the ability of the coating to endure the high-frequency movement of the piezo-electric atomizer 1208 (e.g., the mechanical durability of the coating). As a thickness of the protective coating increases, performance of the atomizer 1208 may be begin to degrade (e.g., as a result of a thicker coating resisting vibration of the atomizer 1208). An example protective coating may include a Parylene coating (e.g., Parylene N, Parylene C, Parylene D, or Parylene HT®). FIG. 12A shows a cross-sectional schematic example of a coated atomizer 1209 (which is an example of the atomizer 1208) having a protective coating 1211 with a coating thickness 1213 that is applied to one or more surfaces 1207 (e.g., a humidification chamber facing surface) of the coated atomizer 1209. Prior to application of the protective coating 1211, the one or more surfaces 1207 may be prepared (e.g., cleaned) to encourage a consistent adhesion of the protective coating 1211.

Additionally, or alternatively, at least a portion of the atomizer 1208 may be made of one or more durable materials. Examples of durable materials may include stainless steel, silver, tungsten, lead zirconate titanate, silicone, and/or a ceramic material. A durable material and/or a protective coating may also be mechanically durable (e.g., in order to operate for a period of at least about six months to at least about five years without failure due to movement of the material when atomizing a liquid). The atomizer 1208 may also include a hydrophobic coating (e.g., the protective coating may be hydrophobic) and/or be at least partially made of a hydrophobic material.

In some instances, when the atomizer 1208 includes a protective coating, the surfaces of the atomizer 1208 to which the protective coating is applied may be pretreated in order to promote adhesion of the protective coating to the atomizer 1208. For an atomizer 1208 having a stainless surface to which a protective coating (e.g., Parylene N) is to be applied, an adhesion promoter may be used. Additionally, or alternatively, polymer adhesion, conformal coatings, optical adhesion, sealers, and/or primers may be used to promote adhesion. In some instances, the atomizer 1208 may be configured to be user replaceable (e.g., as an atomizer module). Such a configuration may allow a user to replace the atomizer 1208 if the atomizer 1208 has experienced substantial degradation or mechanical failure.

The humidification chamber 804 and the atomizer 1208 may be configured to cooperate to generate a desired mix of atomized fluid and ozonated air to form humidified ozonated air. The resulting humidified ozonated air may be configured to have one or more disinfection properties that are effective against one or more pathogens (e.g., viruses, gram-positive bacteria, gram-negative bacteria, and/or any other pathogen).

The humidification chamber 804 includes a includes a bottom wall 1212, a top wall 1214, and one or more chamber sidewalls 1216 extending between the top and bottom wall 1212 and 1214. The bottom wall 1212 may include a generator opening 1215 through which at least a portion of the humidity generator 1204 extends. For example, the atomizer 1208 may be coupled to the bottom wall 1212 on a chamber facing side 1217 of the bottom wall 1212 and the wick assembly 1206 may extend through the generator opening 1215 such that at least a portion of the wick assembly 1206 is on each side of the generator opening 1215. As such, the wick assembly 1206 may be generally described as fluidly coupling the liquid reservoir 802 with the humidification chamber 804.

The atomizer 1208 may be coupled to the bottom wall 1212 such that an emission axis 1218 of the atomizer 1208 extends in a direction of the top wall 1214. In other words, the atomizer 1208 faces the top wall 1214 such that atomized liquid is directed toward the top wall 1214. The top wall 1214 may be configured to define a surface that extends transverse to the bottom wall 1212. In other words, at least a portion of the top wall 1214 may be sloped such that at least a portion of the top wall 1214 does not extend parallel to the bottom wall 1212. Such a configuration may encourage condensation (e.g., as a result of the atomized liquid contacting the top wall 1214) to flow along the top wall 1214 and down the one or more chamber sidewalls 1216. Encouraging condensation to flow towards the one or more chamber sidewalls 1216 may discourage liquid from dripping onto the atomizer 1208.

A slope angle θ (see, also, FIG. 13) defined between the top wall 1214 and a plane parallel to the bottom wall 1212 (e.g., a horizontal plane) may be, for example, in a range of 30° to 60°. By way of further example, the slope angle θ may be in a range of 20° to 70°. By way of still further example, the slope angle θ may be about 45°.

The humidification chamber 804 may further include a humidification chamber ozone inlet 1220 that defines an injection axis 1222 that extends from the humidification chamber ozone inlet 1220 and across the humidification chamber 804. The injection axis 1222 extends transverse to (e.g., perpendicular to) the emission axis 1218. For example, the injection axis 1222 and the emission axis 1218 may intersect at about 90°.

The humidification chamber ozone inlet 1220 may be spaced apart from the atomizer 1208 by a vertical separation distance 1224 (e.g., as measured from a central point of the humidification chamber ozone inlet 1220) and a horizontal separation distance 1226 (e.g., as measured from a central point of the atomizer 1208). Adjusting the vertical and horizontal separation distances 1224 and 1226 such that the atomizer 1208 is proximate to the humidification chamber ozone inlet 1220 may encourage a uniform mixing of ozonated air with atomized liquid, which may improve disinfection performance of the resulting humidified ozonated air. The vertical separation distance 1224 may be, for example, in a range of 9 mm to 19 mm and the horizontal separation distance 1226 may be, for example, in a range of 20 mm to 80 mm. By way of further example, the vertical separation distance 1224 may be about 16 mm and the horizontal separation distance may be about 30 mm. In some instances, a larger humidification chamber 804, a larger atomizer 1208, and/or two or more atomizers 1208 may be used.

The humidification chamber ozone inlet 1220 may include or be coupled to the inlet connector 824. As shown, the inlet connector 824 may be configured to change a direction of the flow path 822 (FIG. 8). For example, the inlet connector 824 includes a connector inlet 1228 having a connector inlet axis 1230 and a connector outlet 1232 having a connector outlet axis 1234, wherein the connector inlet axis 1230 extends transverse to (e.g., perpendicular to) the connector outlet axis 1234. In some instances, the connector outlet axis 1234 may be colinear with the injection axis 1222. The connector inlet axis 1230 may form a connector angle β with the connector outlet axis 1234. The connector angle β may be configured such that the inlet connector 824 introduces turbulence into air flowing therethrough (turbulence may encourage the mixing of ozone with atomized liquid). The connector angle β may be, for example, in a range of 50° to 120°. By way of further example the connector angle β may be about 90°. FIG. 22 shows one example of a flow diagram of the inlet connector 824. FIG. 23 shows one example of a flow diagram of a linear inlet connector.

In some instances, the turbulent flow of air exiting the inlet connector 824 may encourage any condensation of atomized liquid to form within the humidification chamber 804 (e.g., as opposed to within the connected CPAP hose 750). For example, the turbulent flow (e.g., the resultant swirling) may encourage any condensation to occur on the top wall 1214 and/or the one or more chamber sidewalls 1216.

FIG. 12B shows an example of an inlet insert 1250 configured to be coupled to (or formed in) the inlet connector 824. FIG. 12C shows a cross-sectional view of the inlet insert 1250. FIG. 12D an example of the inlet connector 824 that includes the inlet insert 1250. FIG. 24 shows one example of a flow diagram of the inlet insert 1250.

The inlet insert 1250 is configured to encourage generation of a turbulent flow and/or a fan-shaped dispersion pattern 1251 of air (which may include ozone) exiting therefrom. The fan-shaped dispersion pattern 1251 may have a pattern width 1253 that generally corresponds (e.g., about equal to) an emission pattern width 1255 of an atomizer emission 1257 from the atomizer 1208 (e.g., at a point of intersection between the dispersion pattern 1251 and the atomizer emission 1257). Such a configuration may encourage mixing of the air with the generated humidity. The atomizer emission 1257 of the atomizer 1208 may be generally conical in shape. In these instances, the pattern width 1253 of the dispersion pattern 1251 may generally correspond to a diameter of the atomizer emission 1257 at a point of intersection between the dispersion pattern 1251 and the atomizer emission 1257. In some instances, the inlet connector 824 may be angled such that the injection axis 1222 from the inlet connector 824 extends in a direction away from the atomizer 1208. Such a configuration may increase an interaction area between the dispersion pattern 1251 and the atomizer emission 1257. Additionally, or alternatively, one or more dimensions of the humidification chamber 804 (FIG. 8) may be increased to increase the interaction area between the dispersion pattern 1251 and the atomizer emission 1257.

As shown, the inlet insert 1250 defines an insert passageway 1252 that extends from an insert inlet 1254 to an insert outlet 1256. The insert passageway 1252 defines a passageway central axis 1258 that passes through both the insert inlet 1254 and the insert outlet 1256. The insert passageway 1252 has a passageway width 1260 that increases from the insert inlet 1254 to a center portion 1262 of the insert passageway 1252 and decreases from the center portion 1262 to the insert outlet 1256. The passageway width 1260 may be the same at the insert inlet 1254 and at the insert outlet 1256. In this example, the insert passageway 1252 may have a shape that corresponds to the insert inlet 1254 that is revolved 180° about the passageway central axis 1258 while being moved linearly (e.g., for a distance of about 10 mm) along the passageway central axis 1258. In other words, the insert passageway 1252 may have a twisted shape that corresponds to the shape of the insert inlet 1254.

The insert inlet 1254 and the insert outlet 1256 may have the same dimensions. The insert inlet 1254 may have an insert width 1264 and an insert length 1266, the insert length 1266 being greater than the insert width 1264. Such a configuration may result in the generation of the fan-shaped dispersion pattern 1251. The area of the insert inlet 1254 may be about the same as an area of an inlet connector passageway of the inlet connector 824.

FIG. 13 shows a cross-sectional view of a portion of the humidifier assembly 706. As shown, the humidification chamber ozone inlet 1220 faces in a different direction than a humidification chamber outlet 1300. For example, the humidification chamber ozone inlet 1220 may be disposed in a first sidewall 1302 and the humidification chamber outlet 1300 may be disposed in a second sidewall 1304. The first and second sidewalls 1302 and 1304 may be immediately adjacent sidewalls. As also shown, the humidification chamber ozone inlet 1220 and the humidification chamber outlet 1300 may be vertically spaced apart by an inlet/outlet separation distance 1306 (e.g., as measured between a central point of the humidification chamber ozone inlet 1220 and the humidification chamber outlet 1300). The inlet/outlet separation distance 1306 may be, for example, in a range of 30 mm to 100 mm. By way of further example, the inlet/outlet separation distance 1306 may be about 100 mm. As also shown, the top wall 1214 forms a slope angle $\lambda$ with the second sidewall 1304 in a range of, for example, 30° to 60°. By way of further example, the slope angle $\lambda$ may be in a range of 10° to 80°. By way of still further example, the slope angle $\lambda$ may be about 45°.

As also shown, a cross-sectional width 1308 of the of the humidification chamber 804 may decrease in a direction of the humidification chamber outlet 1300. For example, and as shown, at least one sidewall (e.g., the second sidewall 1304 that includes the humidification chamber outlet 1300) may include a non-linear cross-section (e.g., include one or more arcuate or angular portions). In some instances, the humidification chamber 804 may have a chamber volume in a range of, for example 112 milliliters (mL). By way of further example, the chamber volume may be about 180 mL.

Figure 13:
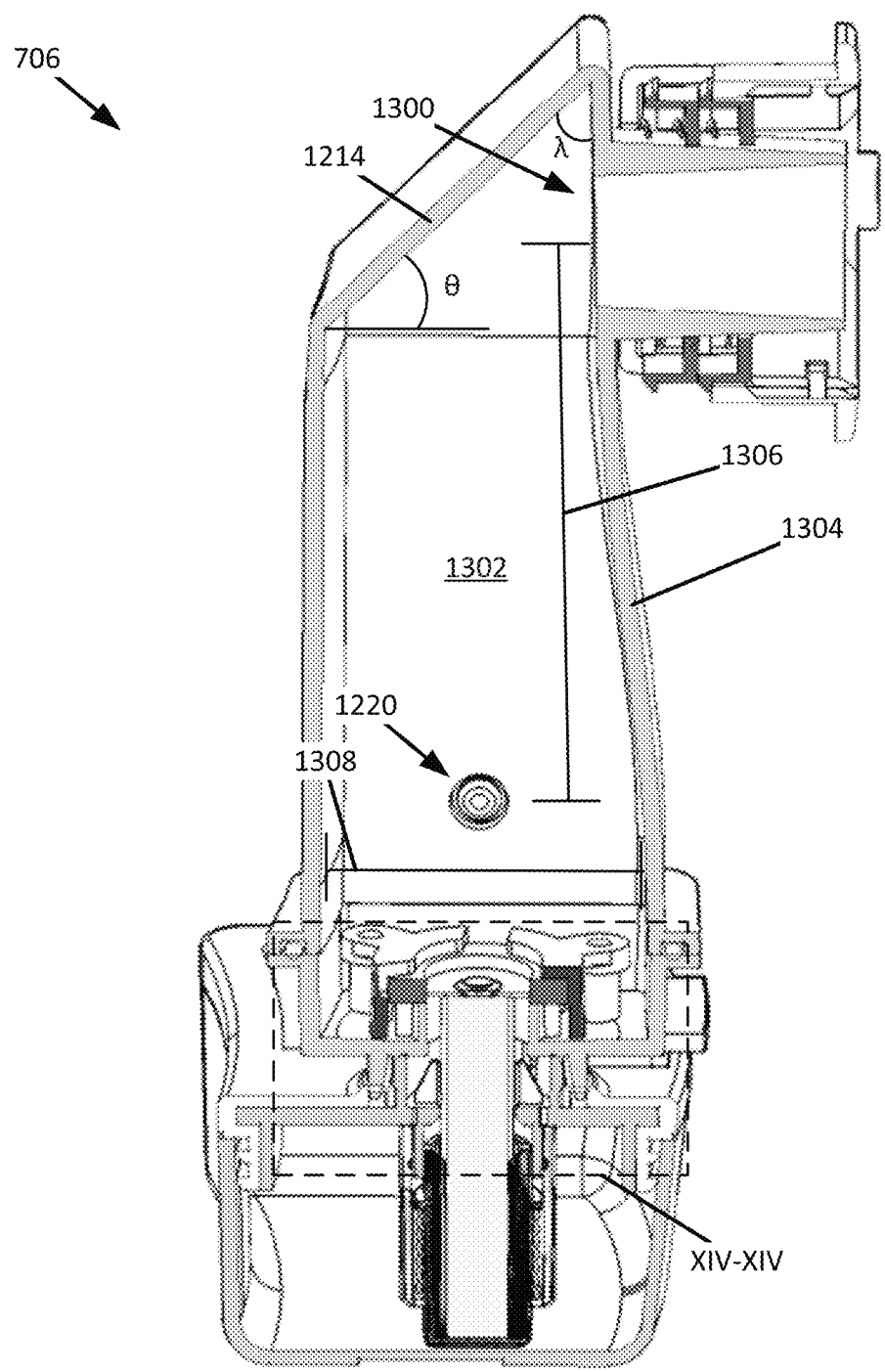
FIG. 13 shows a cross-sectional view of a portion of the humidifier assembly of the disinfection device of FIG. 7, consistent with embodiments of the present disclosure.
Figure 14:
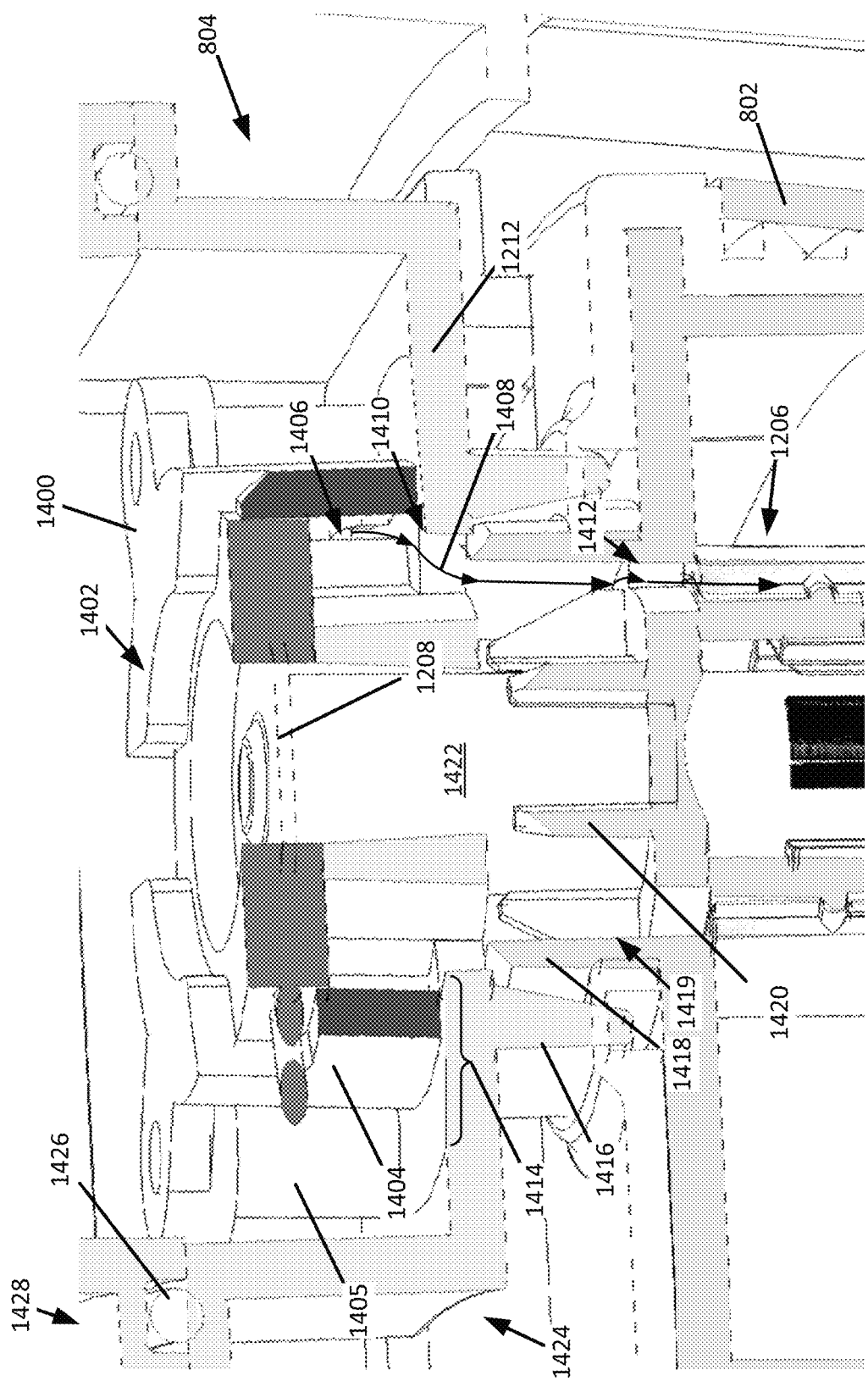
FIG. 14 shows a magnified view generally corresponding to region XIV-XIV of FIG. 13, consistent with embodiments of the present disclosure.
Figure 14A:
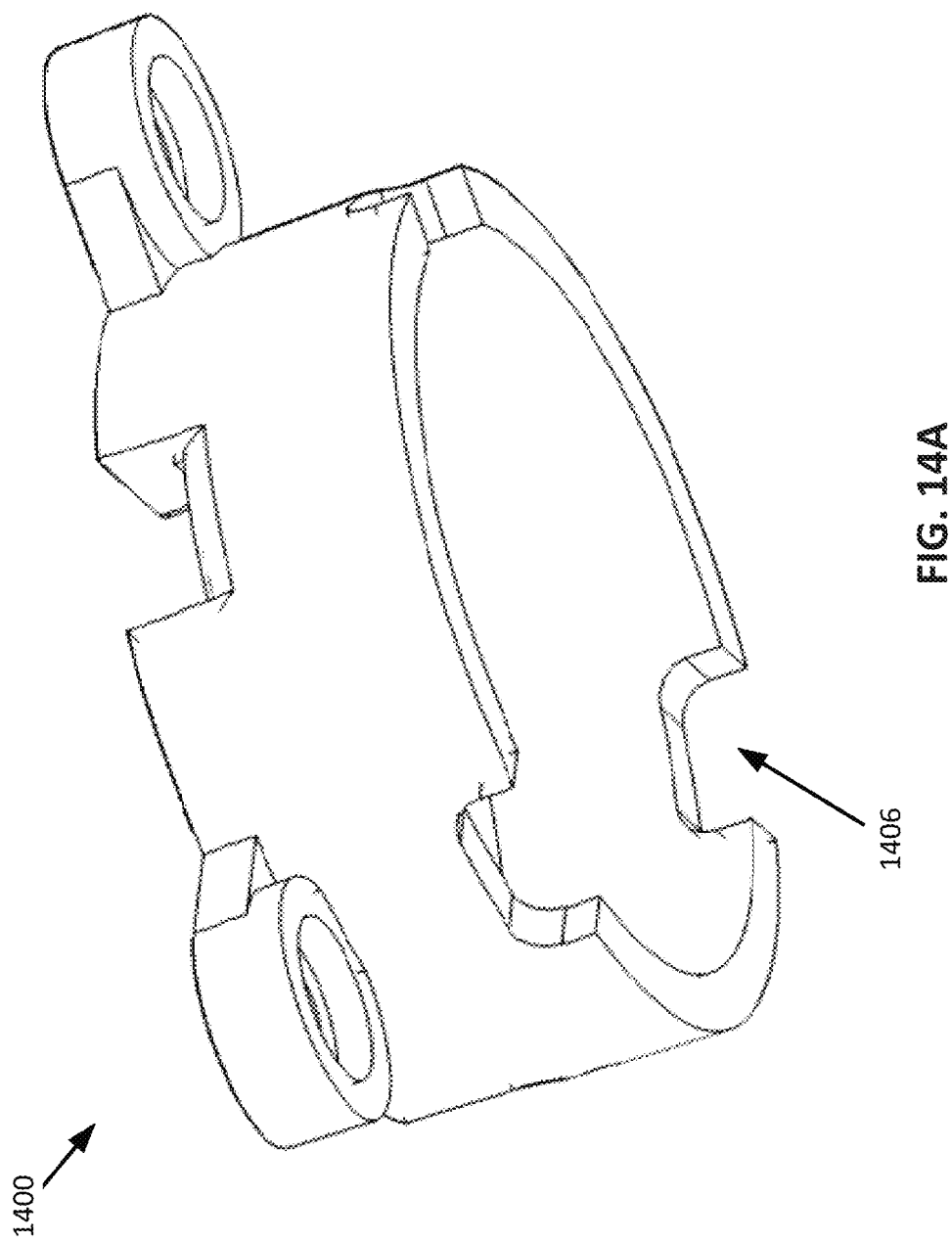
FIG. 14A shows a perspective view of an atomizer retainer, consistent with embodiments of the present disclosure.
Figure 14B:
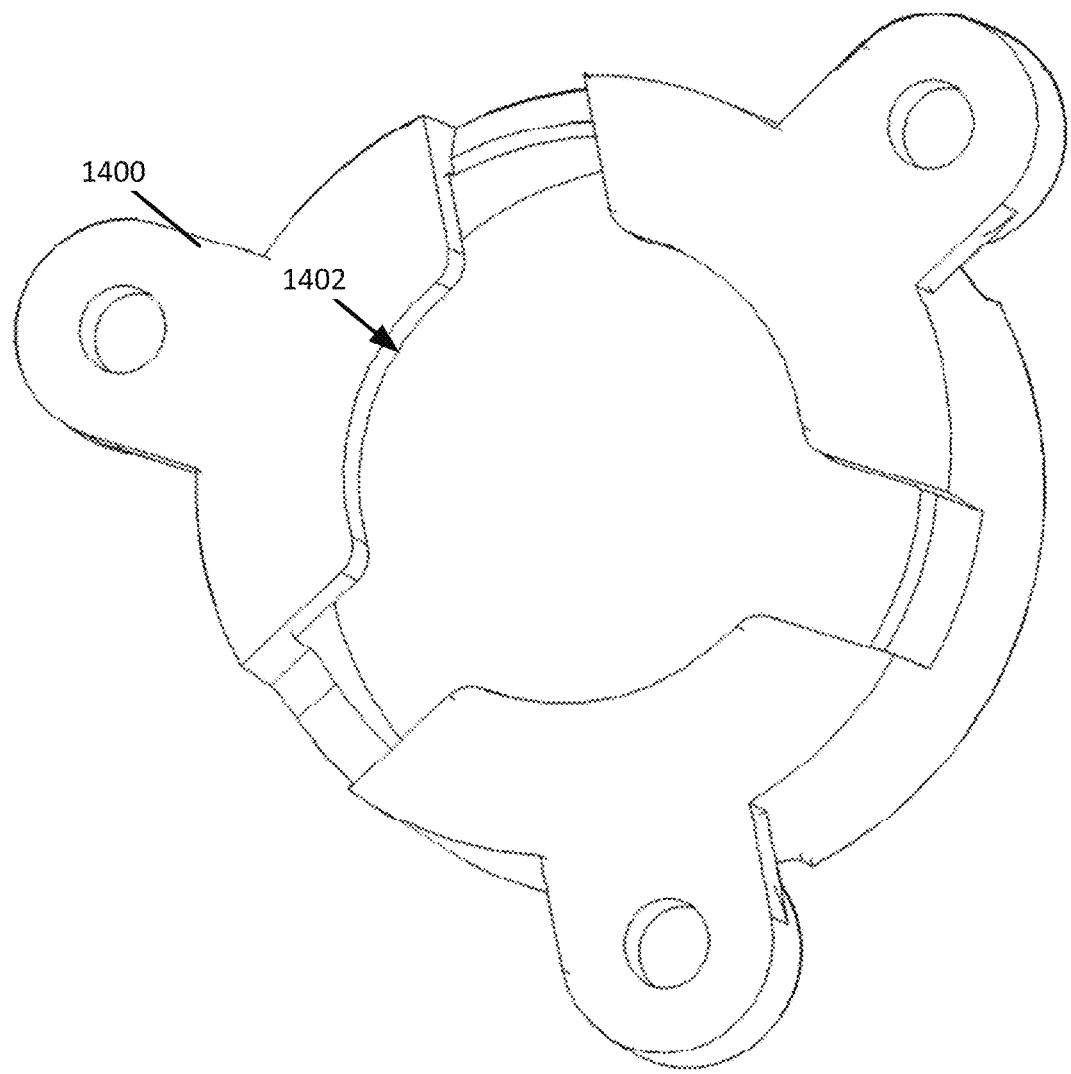
FIG. 14B shows another perspective view of the atomizer retainer of FIG. 14A, consistent with embodiments of the present disclosure.
Figure 15:
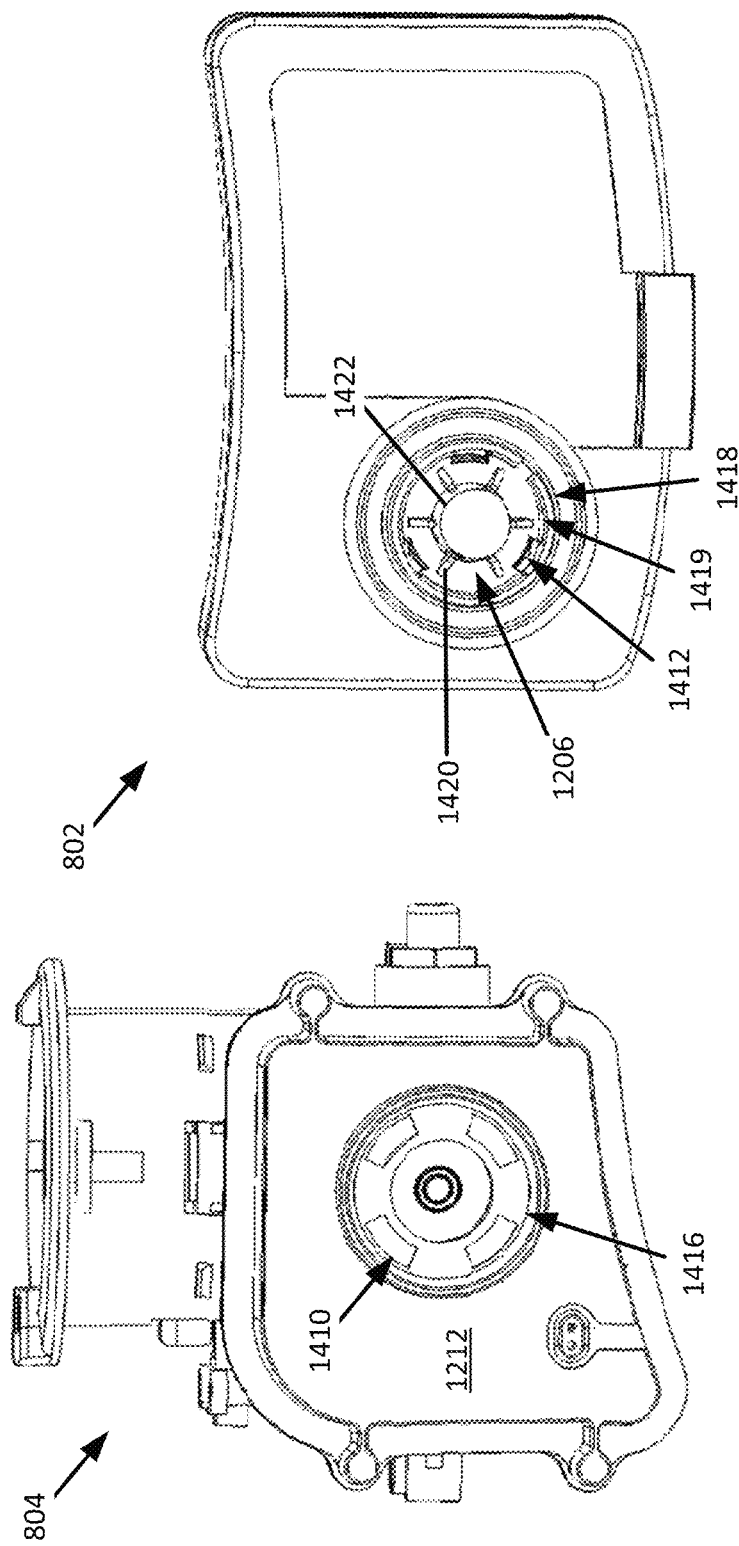
FIG. 15 shows a bottom view of a humidification chamber and a top view of a liquid reservoir of the disinfection device of FIG. 7, consistent with embodiments of the present disclosure.

FIG. 14 is a magnified cross-sectional view generally corresponding to region XIV-XIV of FIG. 13 and FIG. 15 is an exploded view showing a bottom view of the humidification chamber 804 and a top view of the liquid reservoir 802. As shown, the atomizer 1208 is coupled to the bottom wall 1212 of the humidification chamber 804 using a retainer 1400. The retainer 1400 may be formed of, for example, silicone, plastic, metal, and/or any other suitable material. The retainer 1400 includes an atomizer opening 1402 (see, also, FIG. 14B) through which the atomizer 1208 may emit atomized water (e.g., distilled or demineralized water) and one or more retainer walls 1404 configured to engage (e.g., couple to) the bottom wall 1212 and/or stand-offs 1405 extending from the bottom wall 1212. The one or more retainer walls 1404 may include one or more retainer wall drain openings 1406 (see, also, FIG. 14A showing a perspective view of the retainer 1400) through which a drain path 1408 extends. From the one or more retainer wall drain openings 1406, the drain path 1408 extends through one or more bottom wall drain openings 1410 defined in the bottom wall 1212 of the humidification chamber 804. From the one or more bottom wall drain openings 1410, the drain path 1408 extends through one or more reservoir drain openings 1412 defined within the liquid reservoir 802. From the one or more reservoir drain openings 1412, the drain path 1408 may extend along the wick assembly 1206 and into the liquid reservoir 802. In operation, atomized water (which may contain ozone) that condenses on the top wall 1214 (instead of exiting the humidification chamber 804 via the humidification chamber outlet 1300) and flows down the one or more chamber sidewalls 1216 may flow along the drain path 1408 and return to the liquid reservoir 802. In some instances, the bottom wall 1212 may include a sloped region 1414 that encourages water to flow towards the retainer wall drain openings 1406.

Liquid flowing along the drain path 1408 may have ozone entrained therein. The entrained ozone may disinfect the humidification chamber 804, the liquid reservoir 802, and/or the wick assembly 1206. Such a configuration may extend the time between cleanings of the humidifier assembly 706.

As also shown, the bottom wall 1212 includes a reservoir receptacle 1416 configured to receive at least a portion of a reservoir protrusion 1418. A portion of wick assembly 1206 extends within the reservoir protrusion 1418 such that a portion of wick assembly 1206 contacts the atomizer 1208 when the reservoir protrusion 1418 is received within the reservoir receptacle 1416.

The reservoir protrusion 1418 may include the one or more reservoir drain openings 1412 and one or more wick supports 1420 configured to support (e.g., contact) at least a portion of the wick assembly 1206 (e.g., a wick 1422) extending therein. The one or more wick supports 1420 may extend within a protrusion cavity 1419 defined by the reservoir protrusion 1418, wherein a portion of the wick assembly 1206 extends within the protrusion cavity 1419, and the one or more reservoir drain openings 1412 may be defined within the protrusion cavity 1419. When the wick 1422 is wetted, the structural rigidity of the wick 1422 may be reduced and the one or more wick supports 1420 may support the wetted wick 1422 in an upright position. In some instances, when the wick 1422 is dry it may have insufficient structural rigidity to remain in an upright position and be supported by the one or more wick supports 1420 in the upright position. The wick 1422 may be a soft or hard wick. A hard or a soft wick 1422 may each be effective provided that the structural integrity of the wick 1422 is sufficient to maintain the desired interaction between the wick 1422 and the dimple of the atomizer 1208. In some instances, for example, a substantially continuous force between the at least a portion of the wick 1422 and the atomizer 1208 may be in a range of about 0.02 N to about 0.5 N. By way of further example, a substantially continuous force between the at least a portion of the wick 1422 and the atomizer 1208 may be in a range of about 0.05 N to about 0.25 N. As shown, the drain path 1408 extends between the wick assembly 1206 and the reservoir protrusion 1418.

In some instances, a bottom region 1424 of the humidification chamber 804, which includes the bottom wall 1212, may be removable from a top region 1428 of the humidification chamber 804 (e.g., to facilitate cleaning of the humidification chamber 804 and/or replacement of the atomizer 1208). In these instances, a seal 1426 may extend between the bottom region 1424 and the top region 1428 of the humidification chamber 804.

Figure 16:
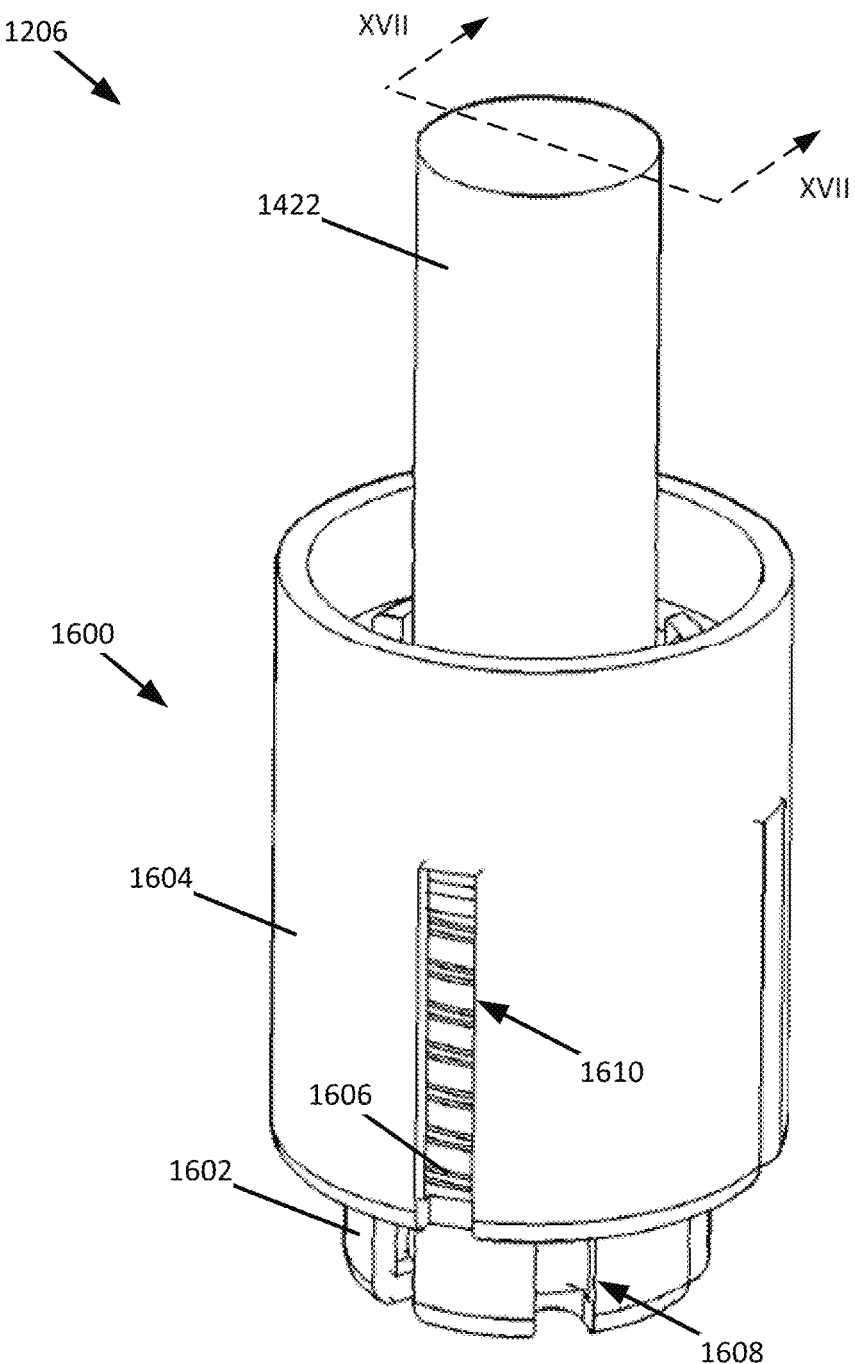
FIG. 16 shows a perspective view of a wick assembly of the disinfection device of FIG. 7, consistent with embodiments of the present disclosure.

FIG. 16 is a perspective view of the wick assembly 1206. As shown, the wick assembly 1206 includes the wick 1422 extending within a cartridge 1600 having a cartridge base 1602 slidably coupled to a cartridge body 1604. A biasing mechanism 1606 (e.g., a spring) extends within the cartridge body 1604 and urges the cartridge base 1602 into engagement (e.g., contact) with the wick 1422. Urging the cartridge base 1602 into engagement with the wick 1422 is configured to urge the wick 1422 into engagement with the atomizer 1208 (FIG. 12), encouraging a more efficient atomization of liquid. In some instances, the wick 1422 may have a shape that generally corresponds to a surface of the atomizer 1208 configured to be contacted by the wick 1422 such that a consistent contact between the atomizer 1208 and the wick 1422 may be maintained.

The cartridge base 1602 and/or the cartridge body 1604 include one or more liquid passthroughs 1608 and/or 1610. The liquid passthroughs 1608 and 1610 are configured to allow liquid to pass from the liquid reservoir 802 (FIG. 8) to the wick 1422.

Figure 17:
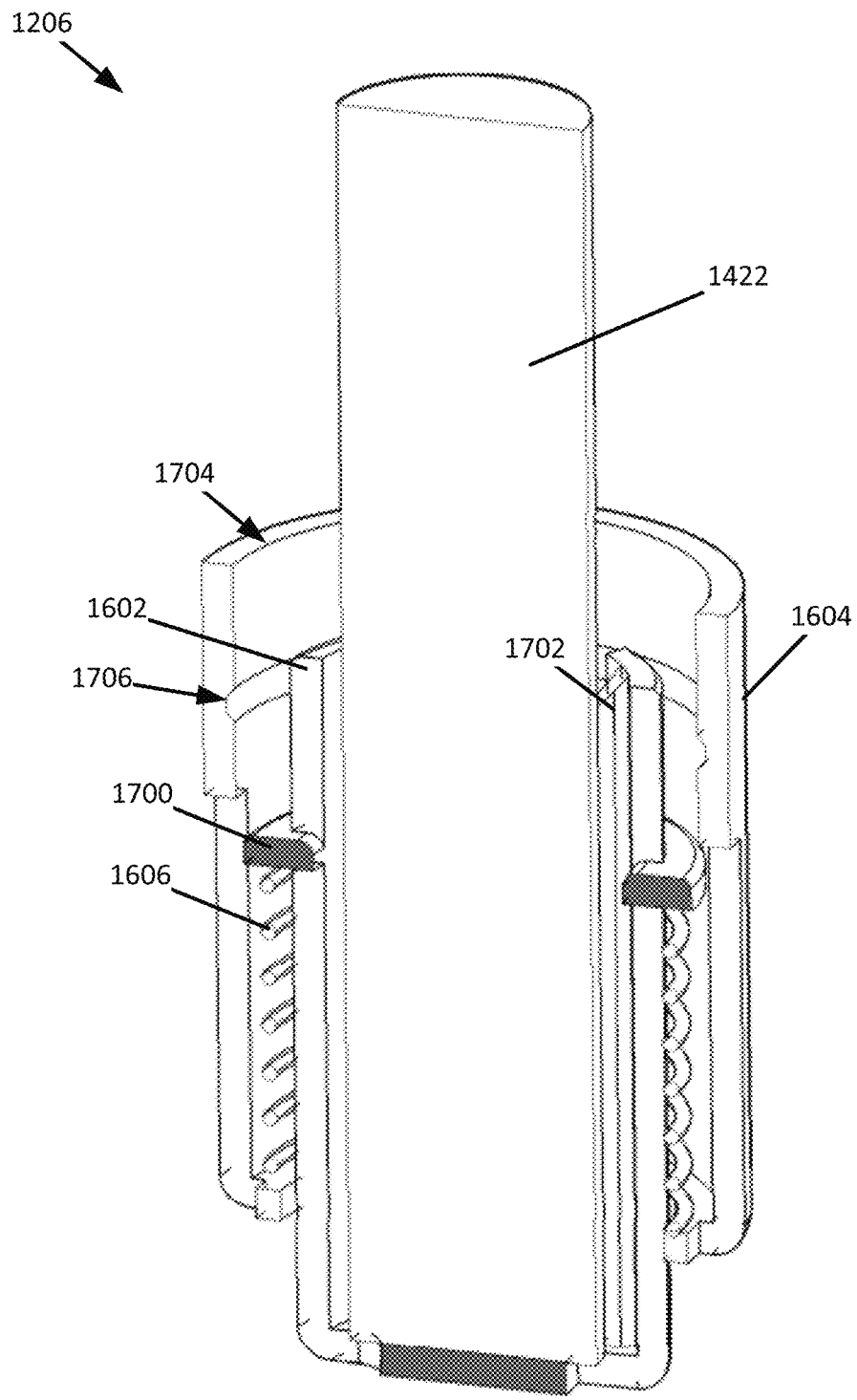
FIG. 17 shows a cross-sectional view of the wick assembly of FIG. 16 taken along the line XVII-XVII of FIG. 16, consistent with embodiments of the present disclosure.
Figure 18:
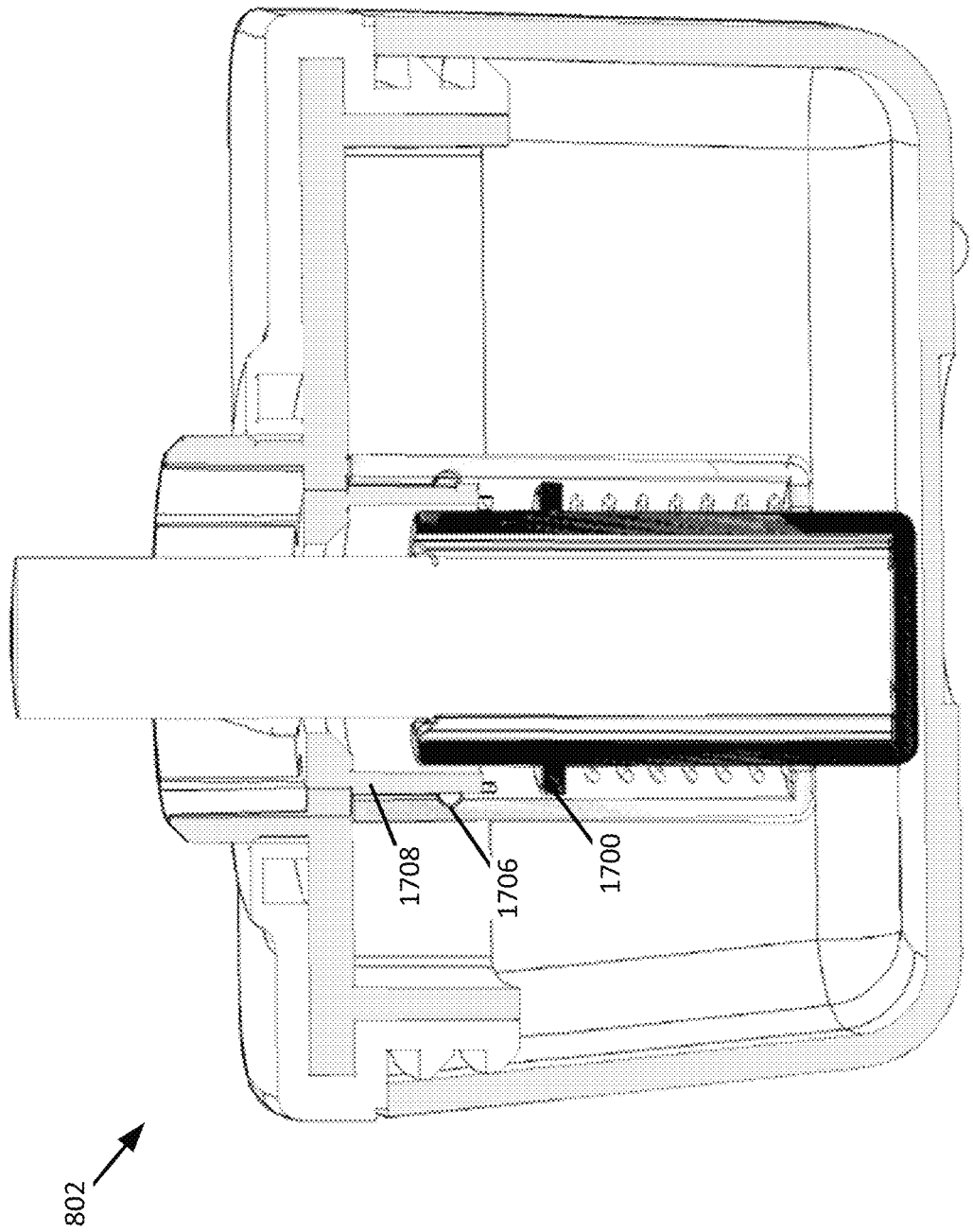
FIG. 18 shows a cross-sectional view of the wick assembly of FIG. 16 coupled to the liquid reservoir of FIG. 15, consistent with embodiments of the present disclosure.

FIG. 17 is a cross-sectional view of the wick assembly 1206 taken along the line XVII-XVII of FIG. 16. As shown, the cartridge base 1602 includes a base flange 1700 and one or more base wick supports 1702 configured to support the wick 1422. The base flange 1700 may be coupled to or formed from the cartridge base 1602. The biasing mechanism 1606 is configured to engage (e.g., contact) the base flange 1700. For example, the biasing mechanism 1606 may be a compression spring configured to urge the cartridge base 1602 in a direction of a cartridge open end 1704, wherein the wick 1422 extends through the cartridge open end 1704. In other words, the biasing mechanism 1606 cooperates with the cartridge base 1602 to urge the wick 1422 in a direction that extends outwardly from the cartridge open end 1704 (e.g., and into contact with the atomizer 1208 of FIG. 12). The cartridge body 1604 may include a locking receptacle 1706 that is configured to removably couple the wick assembly 1206 with the liquid reservoir 802 (FIG. 8). For example, the locking receptacle 1706 may be configured to engage a corresponding protrusion and/or seal of a wick coupler 1708 (FIG. 18) of the liquid reservoir 802. When coupled to the liquid reservoir 802 movement of the cartridge base 1602 within the cartridge body 1604 in a direction of the cartridge open end 1704 is restricted by the wick coupler 1708 of the liquid reservoir 802 engaging the base flange 1700 (see, e.g., FIG. 18).

The one or more base wick supports 1702 are configured to engage at least a portion of the wick 1422. When the wick 1422 becomes saturated with liquid, the structural rigidity of the wick 1422 may become compromised. The one or more base wick supports 1702 may be configured to retain the wick 1422 in an upright orientation when saturated with liquid (and/or if the wick 1422 is insufficiently rigid to maintain an upright orientation when dry). Such a configuration may encourage a more consistent contact between the atomizer 1208 and the wick 1422.

Figure 19:
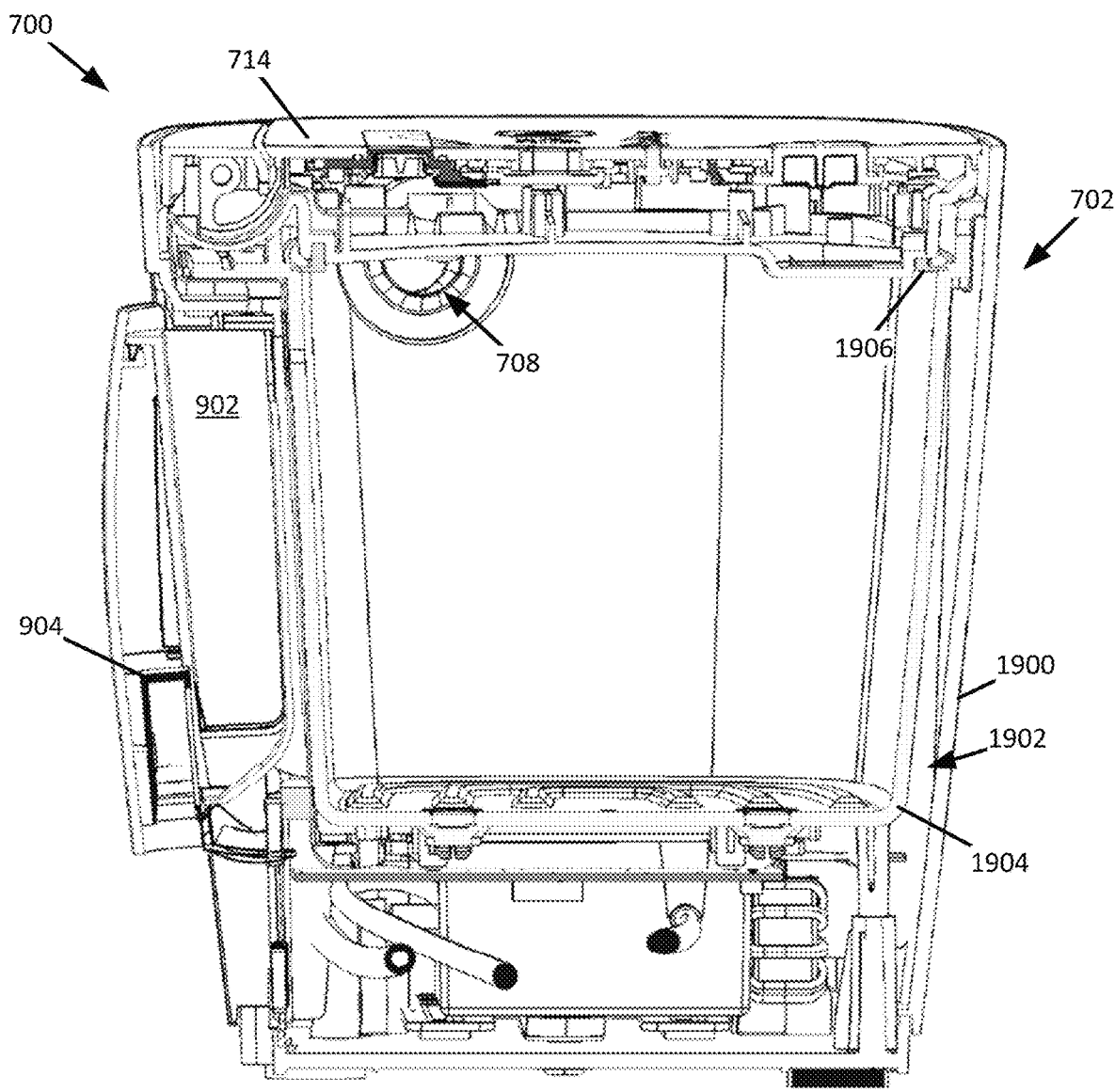
FIG. 19 shows a cross-sectional view of the disinfection device of FIG. 7 taken along the line XIX-XIX of FIG. 7, consistent with embodiments of the present disclosure.

FIG. 19 is a cross-sectional view of the disinfection device 700 taken along the line XIX-XIX of FIG. 7. As shown, the disinfection chamber 702 includes a disinfection body 1900 defining a cavity 1902 that includes a disinfection receptacle 1904. The disinfection chamber lid 714 is pivotally coupled to the disinfection body 1900 and includes a disinfection chamber seal 1906 configured to sealing engage with the disinfection receptacle 1904 when the disinfection chamber lid 714 is in a closed (e.g., operating) position. The disinfection chamber seal 1906 is configured to prevent and/or mitigate the leakage of ozone from the disinfection receptacle 1904. For example, the disinfection chamber seal 1906, the CPAP hose passthrough 708, and the ozone reduction filter 902 may be configured such that a total leakage of ozone from the disinfection device 700 is less than 0.05 ppm as measured 12 centimeters (cm) from the disinfection device 700. In some instances, the upstream fan 904 and/or pump 1000 (FIG. 10) may be operated to maintain ozone within the CPAP hose 750, the CPAP mask 754, and/or the disinfection receptacle 1904 within a predetermined range (e.g., by generating ozone pulses using the ozone generation assembly 704) and to maintain humidity within the CPAP hose 750, the CPAP mask 754, and/or the disinfection receptacle 1904 within a predetermined range (e.g., without generating humidity using the humidifier assembly 706). In other words, the upstream fan 904 and/or the pump 1000 may be operated such that a desired environment is maintained within the CPAP hose 750, the CPAP mask 754, and/or the disinfection receptacle 1904.

In some instances, when operating the disinfection device 700, a quantity of ozone within the CPAP hose 750, the CPAP mask 754, and/or the disinfection receptacle 1904 may be controlled. For example, the quantity of ozone within the disinfection receptacle 1904 may be controlled to be in a range of about 200 ppm to about 300 ppm. By way of further example, the quantity of ozone may be controlled to be in a range of about 100 ppm to about 400 ppm. By way of still further example, the quantity of ozone may be controlled to be in a range of about 120 ppm to about 200 ppm. By way of still further example, the quantity of ozone may be controlled to be about 285 ppm. By way of still further example, the quantity of ozone may be controlled to be about 160 ppm. In some instances, when operating the disinfection device 700, a humidity within the disinfection receptacle 1904 may be controlled. For example, the relative humidity within the disinfection receptacle 1904 may be controlled to be in a range of 50% to 99.9%. By way of further example, the relative humidity within the disinfection receptacle 1904 may be controlled to be in a range of 70% to 90%. By way of still further example, the relative humidity within the disinfection receptacle 1904 may be about 70%.

In addition, or in the alternative, to controlling the ozone generation assembly 704 to control a quantity of ozone within the CPAP hose 750, the CPAP mask 754, and/or the disinfection receptacle 1904 and/or controlling the humidifier assembly 706 to control a relative humidity within the CPAP hose 750, the CPAP mask 754, and/or the disinfection receptacle 1904, a speed of the upstream fan 904 and/or pump 1000 may be controlled. By controlling the speed of one or more of the upstream fan 904 and/or pump 1000 the rate at which ozone and/or humidity is delivered to (e.g., via the CPAP hose 750 and/or the CPAP mask 752) and removed from the disinfection receptacle 1904 may be controlled, which controls the quantity of ozone and/or the humidity within the disinfection receptacle 1904 and objects being disinfected (e.g., the CPAP hose 750 and/or the CPAP mask 752). For example, the pump 1000 may be operated to generate a flow rate in a range of about 1.1 standard liter per minute (SLPM) to 1.6 SLPM and the upstream fan 904 (FIG. 10) may be operated to generate a flow rate in a range of about 0.9 SLPM to about 1.6 SLPM. By way of further example, the upstream fan 904 may be operated to generate a flow rate of 1.3 SLPM and the pump 1000 of 1.3 SLPM. By way of still further example, the upstream fan 904 may be operated to generate a flow rate of 1.2 SLPM and the pump 1000 of 1.3 SLPM. In some instances, the disinfection device 700 may be configured such that the disinfection receptacle 1904 is under vacuum, under pressure, or alternates between being under vacuum and under pressure. Having, the upstream fan 904 operate at a lower flow rate than the pump 1000 may improve disinfection performance (e.g., encourage an at least 4-$Log_{10}$, at least 5-$Log_{10}$, or at least 6-$Log_{10}$ disinfection performance). In some instances, the flow rate may be configured such that, for a given quantity of entrained ozone, a desired level of disinfection (e.g., at least 4-$Log_{10}$) is obtained for one or more pathogens (e.g., one or more viruses, one or more gram-positive bacteria, one or more gram-negative bacteria, and/or any other pathogens).

Figure 19A:
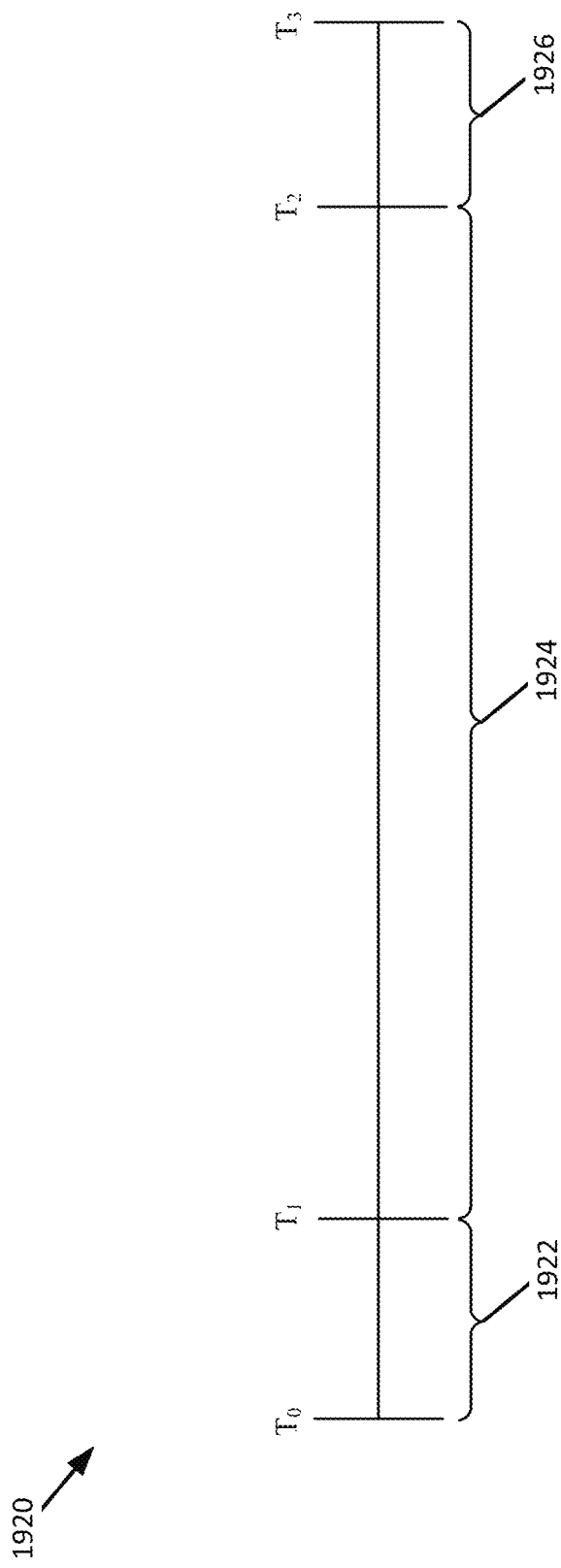
FIG. 19A shows a schematic example of an operational timeline for the disinfection device of FIG. 7, consistent with embodiments of the present disclosure.
Figure 19B:
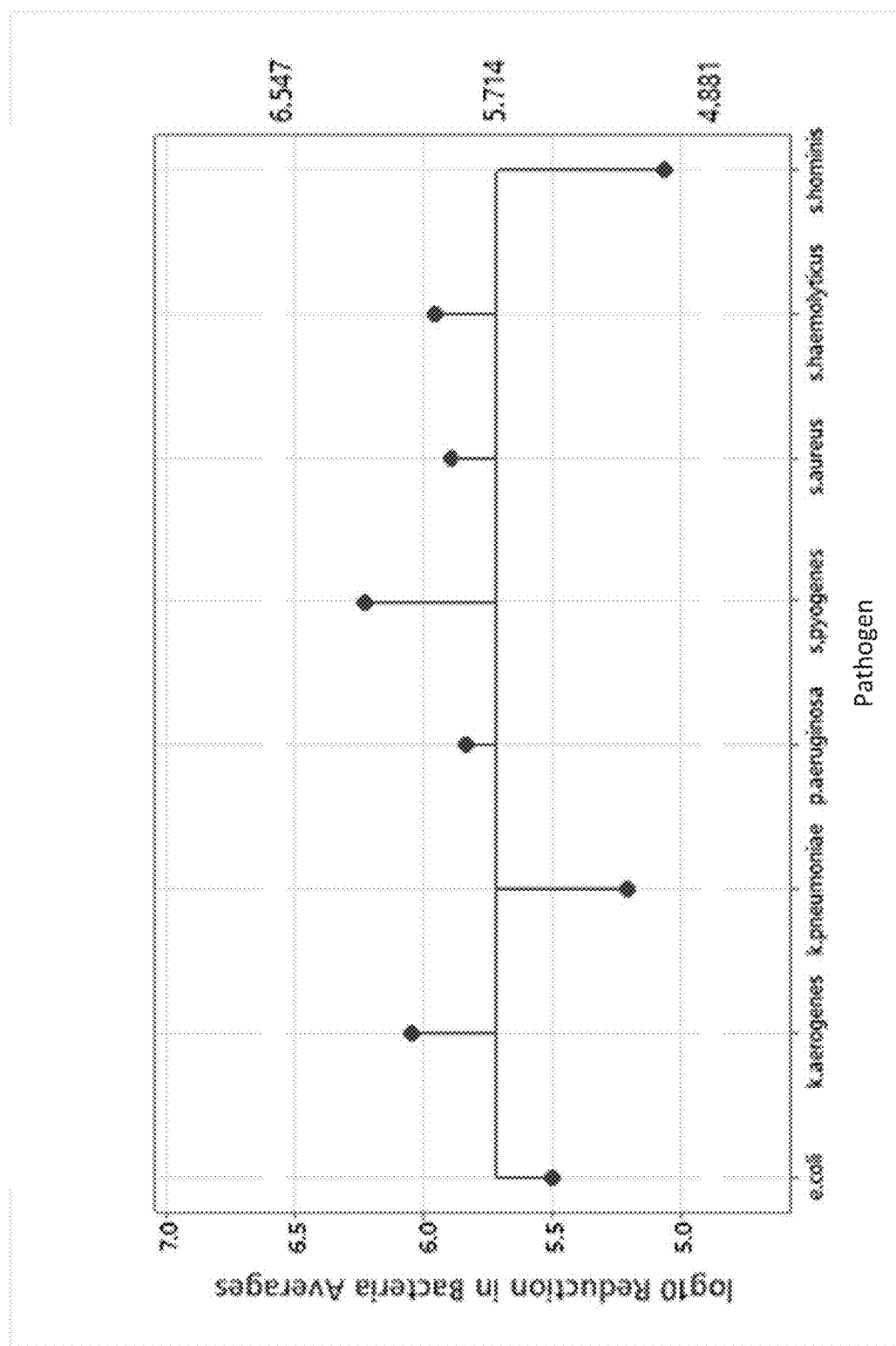
FIG. 19B shows one example of an efficacy outcome using one example of the disinfection device of FIG. 7 that is implementing one example of the operational timeline of FIG. 19A, consistent with embodiments of the present disclosure.

FIG. 19A shows a schematic example of an operational timeline 1920 of the disinfection device 700 that corresponds to one example operation profile (e.g., a disinfection cycle) and is an example of the operational timeline 400 of FIG. 4. When the disinfection device 700 is operated according to the operational timeline 1920, an object (e.g., the CPAP mask 754 or CPAP hose 750) being disinfected by the disinfection device 700 may experience at least a 4-$Log_{10}$ reduction in at least one pathogen. FIG. 19B shows one example of an efficacy outcome using one example of the disinfection device 700 that is implementing one example of the operational timeline 1920, wherein the efficacy achieved is greater than 4-$Log_{10}$ for the listed pathogens.

As shown, a first period 1922 extends between time $T_0$ and time $T_1$, a second period 1924 extends between time $T_1$ and time $T_2$, and a third period 1926 extends between time $T_2$ and time $T_3$, wherein time $T_3$ is greater than time $T_2$, time $T_2$ is greater than time $T_1$, and time $T_1$ is greater than time $T_0$. A cycle time extending from $T_0$ to $T_3$ may be, for example, in a range of about (e.g., within 1%, 2%, 3%, 4%, or 5% of) 60 minutes to about 120 minutes. By way of further example, the cycle time may be about 90 minutes. The first period 1922 may be, for example, in a range of about 4 to about 6 minutes. By way of further example, the first period 1922 may be about 6 minutes. The second period 1914 may be, for example, in a range of about 60 to about 80 minutes. By way of further example, the second period 1924 may be about 72 minutes. The third period 1926 may be, for example, in a range of about 8 minutes to about 16 minutes. By way of further example, the third period 1926 may be about 12 minutes. The pump 1000 may be configured to operate at a pump flow rate and the upstream fan 904 may be configured to operate at a fan flow rate, the pump flow rate being different from the fan flow rate during at least one of the first period 1922, the second period 1924, and/or the third period 1926.

During the first period 1922, the ozone generation assembly 704 (FIG. 7) may be caused to generate ozone in a range of, for example, about (e.g., within 1%, 2%, 3%, 4%, 5%, or 10% of) 220 ppm to about 300 ppm, which may, in some instances, correspond to about 80 ppm to about 150 ppm of ozone within the disinfection chamber 702 (FIG. 7). By way of further example, during the first period 1922, the ozone generation assembly 704 may be caused to generate about 270 ppm of ozone. Depending on the travel time for ozone to travel from the ozone generation assembly 704 to the disinfection chamber 702, the ozone generation assembly 704 may be configured to generate a sufficient quantity of ozone such that the ozone within the CPAP hose 750, the CPAP mask 754, and/or the disinfection chamber 702 is in a range of about 80 ppm to about 150 ppm. Alternatively, in some instances, the ozone generation assembly 704 may be disabled during the first period 1922.

During the first period 1922, the humidifier assembly 706 (FIG. 7) may be caused to generate humidity that passes through the CPAP hose 750 and CPAP mask 754 to enter the disinfection chamber 702. For example, the humidifier assembly 706 may be caused to generate humidity until a relative humidity (e.g., as measured or estimated) within the CPAP hose 750, the CPAP mask 754, and/or the disinfection chamber 702 to in a range of about (e.g., within 1%, 2%, 3%, 4%, 5%, or 10% of) 65% to about 99%. By way of further example, the humidifier assembly 706 may be configured to generate humidity until a relative humidity within a range of about 74% to about 90% within the CPAP hose 750, the CPAP mask 754, and/or the disinfection chamber 702 is achieved. By way of still further example, the humidifier assembly 706 may be configured to generate humidity until a relative humidity is within a range of about 55% to about 99% within the CPAP hose 750, the CPAP mask 754, and/or the disinfection chamber 702 is achieved. Alternatively, in some instances, the humidifier assembly 706 may be disabled during the first period 1922.

In some instances, during the first period 1922, only one of the ozone generation assembly 704 or the humidifier assembly 706 is enabled. For example, only the humidifier assembly 706 may be enabled during the first period 1922 such that a relative humidity within the disinfection chamber 702 reaches a desired amount prior to the generation of ozone. In some instances, during the first period 1922, the ozone generation assembly 704 and the humidifier assembly 706 may each be enabled. For example, the ozone generation assembly 704 and the humidifier assembly 706 may each be enabled during the first period 1922 without being enabled at the same time. By way of further example, the ozone generation assembly 704 and the humidifier assembly 706 may be both enabled at the same time during the first period 1922. The ozone generation assembly 704 and/or the humidifier assembly 706 may be enabled for the entire first period 1922.

During the first period 1922, the pump 1000 (FIG. 10) may be operated according to an initialization pump flow rate and the upstream fan 904 may be operated according an initialization fan flow rate. The initialization pump flow rate may be different from (e.g., greater than) the initialization fan flow rate. For example, a ratio of initialization fan flow rate to initialization pump flow rate (i.e., initialization fan flow rate divided by initialization pump flow rate) may be about 0.9. In some instances, the initialization pump flow rate may be in a range of about (within 1%, 2%, 3%, 4%, or 5% of) 1 SLPM to about 1.6 SLPM. In some instances, the initialization fan flow rate may be about 0.1 to 0.15 SLPM less than the initialization pump flow rate.

During the second period 1924, the humidifier assembly 706 may be disabled and the ozone generation assembly 704 may be enabled for at least a portion of the second period 1924. For example, the ozone generation assembly 704 may be cycled between being enabled and disabled (e.g., according to a fixed or varying duty cycle). In this example, the ozone generation assembly 704 may generally be described as being configured to generate ozone pulses at a pulse rate (or duty cycle). When generating ozone pulses, the duty cycle of the ozone generation assembly 704 may be such that a quantity of ozone within the disinfection chamber 702 (e.g., as measured or estimated) is in a range of about 80 ppm to about 150 ppm. One example pulse rate of the ozone generation assembly 704 may result in the ozone generation assembly 704 being enabled for about 10 seconds and disabled for about 65 seconds. In some instances, the duty cycle may be adjusted based, at least in part, on, for example, an output of an ozone sensor within the disinfection chamber 702. During the second period 1924, the pump 1000 and/or upstream fan 904 may, in some instances, be enabled when the ozone generation assembly 704 is generating ozone and disabled when the ozone generation assembly 704 is not generating ozone.

During the second period 1924, the pump 1000 may be operated according to an operational pump flow rate and the upstream fan 904 may be operated according an operational fan flow rate. The operational pump flow rate may be different from (e.g., greater than) the operational fan flow rate. For example, the operational pump flow rate may be greater than the operational fan flow rate. Such a configuration, may encourage ozone to come into contact with one or more surfaces of the CPAP mask 754 and/or the CPAP hose 750.

For example, a ratio of operational fan flow rate to operational pump flow rate (i.e., operational fan flow rate divided by operational pump flow rate) may be about 0.9. In some instances, operational pump flow rate may be in a range of about (within 1%, 2%, 3%, 4%, or 5% of) 1 SLPM to about 1.6 SLPM. In some instances, the operational fan flow rate may be about 0.1 to 0.15 SLPM less than the operational pump flow rate.

During the third period 1926 the humidifier assembly 706 and the ozone generation assembly 704 may be disabled. During the third period 1926, the upstream fan 904 and/or the pump 1000 may be operated according to a purge fan/pump flow rate. The purge fan flow rate may be greater than about 90% (e.g., about 100%) of a maximum flow rate capable of being generated by the upstream fan 904 and/or the purge pump flow rate may be greater than about 90% (e.g., about 100%) of a maximum flow rate capable of being generated by the pump 1000. The purge fan and purge pump flow rates may be configured to urge a substantial quantity of any remaining ozone through the ozone reduction filter 902 (FIG. 9) prior to expiration of the third period 1926. In some instances, the purge fan flow rate may be greater than or equal to the purge pump flow rate. In some instances, the purge pump flow rate may be, for example, in a range of about (within 1%, 2%, 3%, 4%, or 5% of) 1 SLPM to about 1.6 SLPM and the purge fan flow rate may be in a range of about 10 SLPM to about 16 SLPM.

Figure 20:
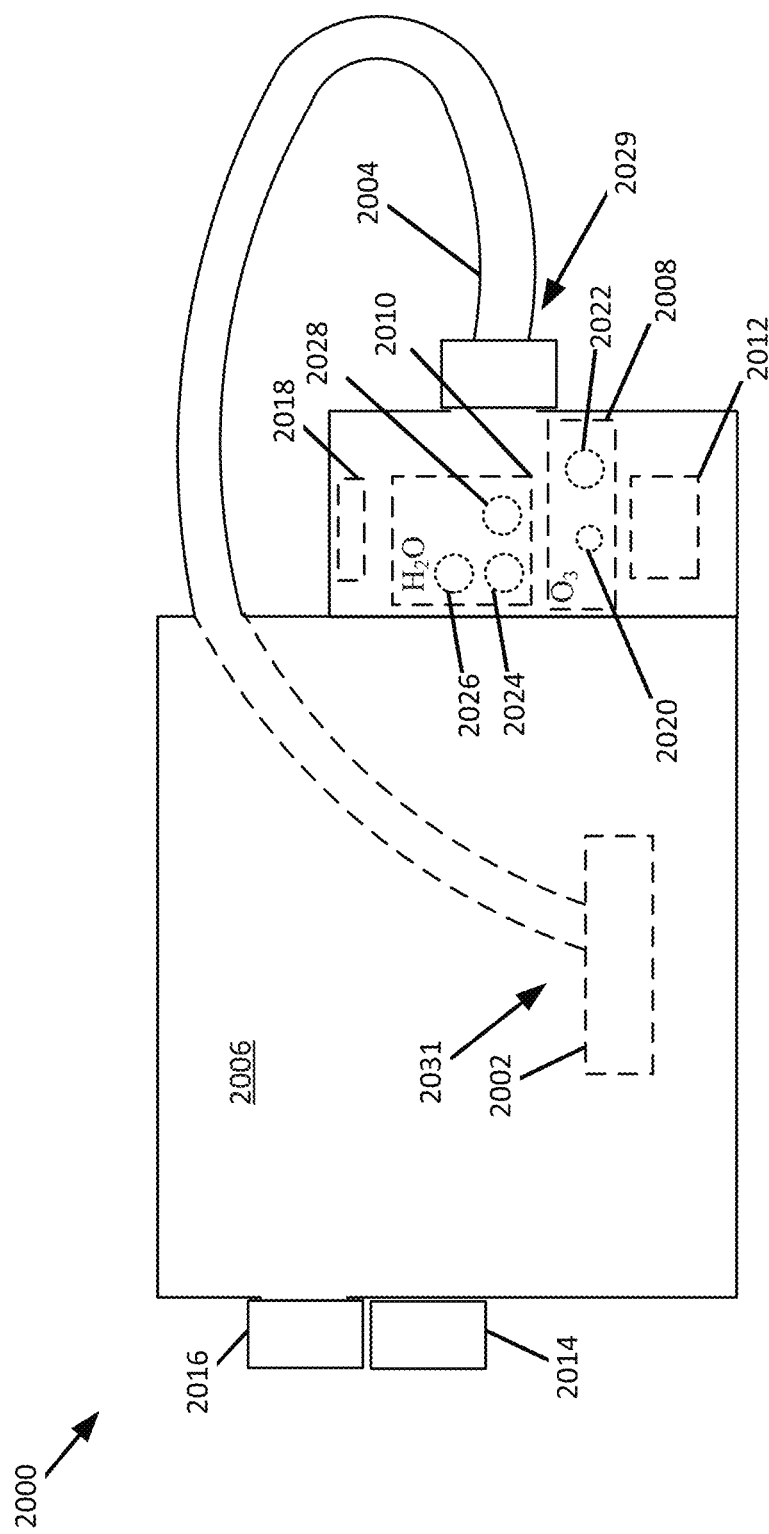
FIG. 20 shows a schematic example of a disinfection device, consistent with embodiments of the present disclosure.

FIG. 20 is a schematic example of a disinfection device 2000, which is an example of the disinfection device 700 of FIG. 7. The disinfection device 2000 is configured to achieve at least a 4-$Log_{10}$ (e.g., at least a 6-$Log_{10}$) kill rate of one or more bacteria on a CPAP mask 2002 and/or on a CPAP hose 2004, wherein the one or more bacteria may include, but are not limited to, one or more of *Escherichia coli, Staphylococcus aureus, Pseudomonas aeruginosa, Staphylococcus haemolyticus, Streptococcus pyogenes, Staphylococcus hominis, Klebsiella pneumoniae*, and/or *Enterobacter cloacae*. In other words, the disinfection device 2000 is configured to cause at least a 99.9999% reduction of one or more bacteria in the CPAP mask 2002 and the CPAP hose 2004.

As shown, the disinfection device 2000 includes a disinfection chamber 2006, an ozone generator 2008, a humidifier 2010, a pump 2012, an upstream fan 2014, and an ozone reduction filter 2016. The CPAP hose 2004 fluidly couples the pump 2012, the ozone generator 2008, and the humidifier 2010 to the disinfection chamber 2006. As shown, the ozone generator 2008 is downstream of the pump 2012, the humidifier 2010 is downstream of the ozone generator 2008, the CPAP hose 2004 is downstream of the humidifier 2010, the disinfection chamber 2006 is downstream of the CPAP hose 2004, the ozone reduction filter 2016 is downstream of the disinfection chamber 2006, and the upstream fan 2014 is downstream of the ozone reduction filter 2016. In some instances, the CPAP mask 2002 may be coupled to the CPAP hose 2004 and be disposed within the disinfection chamber 2006.

The humidifier 2010, the pump 2012, and the ozone generator 2008 are external to the disinfection chamber 2006. The CPAP mask 2002 and the CPAP hose 2004 fluidly couple the humidifier 2010, the pump 2012, and the ozone generator 2008 to the disinfection chamber 2006. The humidifier 2010, the pump 2012, and/or the ozone generator 2008 may be arranged in any configuration relative to the disinfection chamber 2006. For example, one or more of the humidifier 2010, the pump 2012, and/or the ozone generator 2008 may be arranged at least partially below the disinfection chamber 2006. By way of further example, one or more of the humidifier 2010, the pump 2012, and/or the ozone generator 2008 may be arranged at least partially along a side of and/or separate from the disinfection chamber 2006. In some instances one or more of the humidifier 2010, the pump 2012, and/or the ozone generator 2008 may be movable relative to the disinfection chamber 2006.

The disinfection device 2000 further includes a controller 2018 that is communicatively coupled to one or more of the ozone generator 2008, the humidifier 2010, the pump 2012, and/or the upstream fan 2014. The controller 2018 is configured to operate one or more of the ozone generator 2008, the humidifier 2010, the pump 2012, and/or the upstream fan 2014 according to one or more operation profiles (e.g., a disinfection cycle) that are configured to achieve a desired environment within the disinfection chamber 2006 (e.g., to achieve at least a 4-$Log_{10}$ or at least a 6-$Log_{10}$ kill rate).

The ozone generator 2008 includes a relative humidity sensor 2020 (e.g., positioned at an inlet side of the ozone generator 2008), and an ozone sensor 2022 (e.g., positioned at an outlet side of the ozone generator 2008). For example, the ozone sensor 2022 may be positioned downstream of an ozone source of the ozone generator 2008 and upstream of the humidifier 2010. The controller 2018 is configured to operate the ozone generator 2008 according to an operation profile based, at least in part, on a detected ozone quantity as detected by the ozone sensor 2022 and/or a detected relative humidity as detected by the relative humidity sensor 2020. For example, the controller 2018 may operate the ozone generator 2008 to generate a quantity of ozone in a range of about 200 ppm to about 300 ppm, as detected by the ozone sensor 2022. In order to more quickly reach a desired ozone quantity, the controller 2018 may use the detected relative humidity to determine initial operation parameter(s) of the ozone generator 2008 (e.g., the controller 2018 generates an estimated quantity of ozone that is expected to be generated by the ozone generator 2008 for given operation parameter(s) at the detected relative humidity and causes the ozone generator 2008 to be operated accordingly).

Figure 20A:
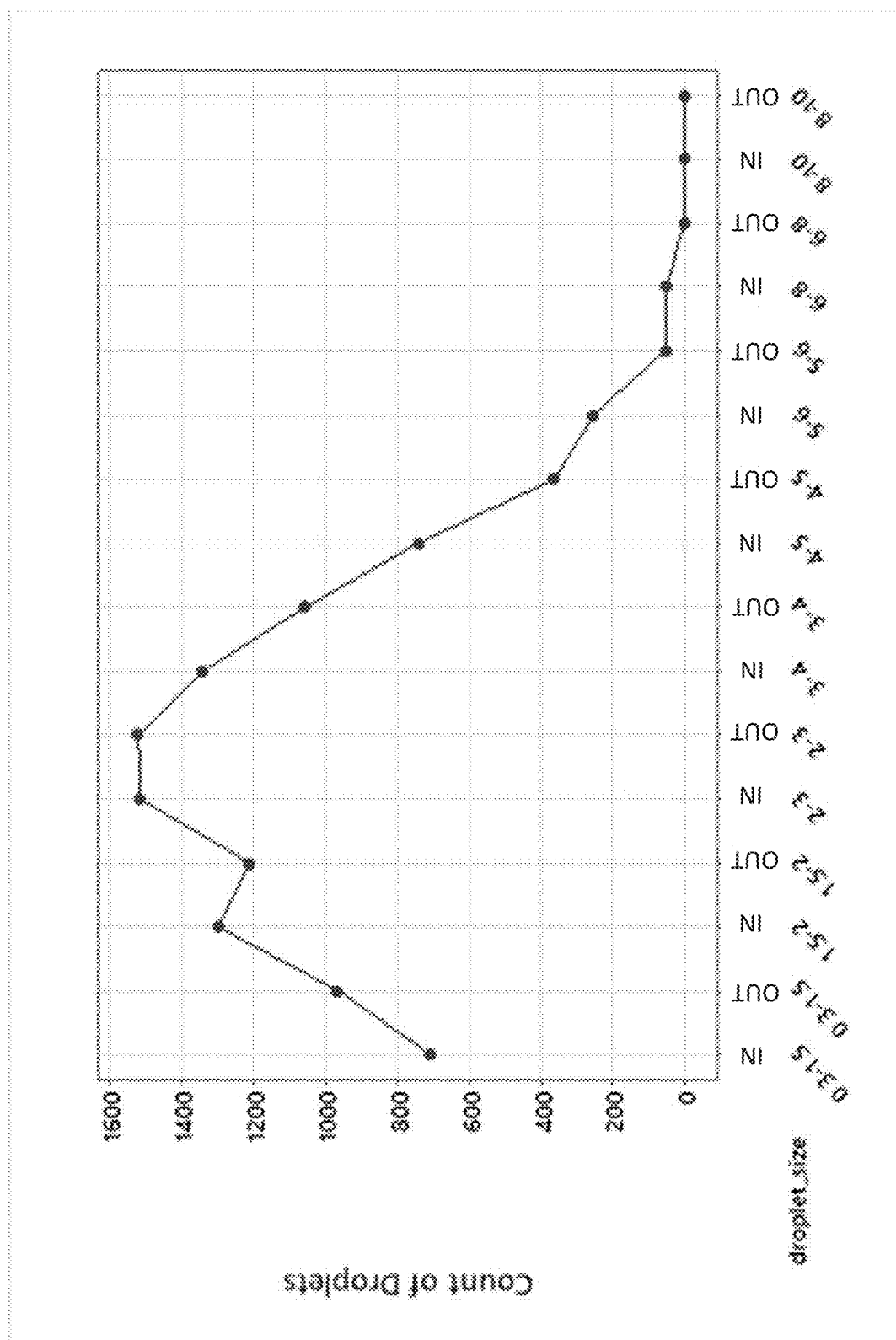
FIG. 20A shows one example distribution of atomized water droplet sizes produced by an example of the piezoelectric atomizer of FIG. 20, consistent with embodiments of the present disclosure.

The humidifier 2010 includes a liquid reservoir 2024, a humidification chamber 2026, and a piezo-electric atomizer 2028 configured to atomize liquid from the liquid reservoir 2024 into the humidification chamber 2026. The controller 2018 is configured to operate the piezo-electric atomizer 2028 according to the operation profile in order to generate a desired relative humidity. The piezo-electric atomizer 2028 may include about (e.g., within 1%, 2%, 3%, 4%, 5%, 10%, or 15% of) 2,640 holes having a hole size of about (e.g., within 1%, 2%, 3%, 4%, 5%, 10%, or 15% of) 2.5 microns with a theoretical maximum atomized volume of water per pulse of about 22.3 pico-liters (pL). Such a configuration for the piezo-electric atomizer 2028 may result in the most prevalent value of atomized water droplet size being in a range of, for example, about 2.5 microns to about 3 microns. FIG. 20A shows one example distribution of atomized water droplet sizes produced by an example of the piezo-electric atomizer 2028, wherein droplet sizes were measured at an inlet 2029 of the CPAP hose 2004 (labeled IN in FIG. 20A) and an outlet 2031 of the CPAP hose 2004 (e.g., at the CPAP mask 2002) (labeled OUT in FIG. 20A). As shown, droplets having a size in a range of 2 microns to 3 microns were the most prevalent and present in substantially similar numbers at both the inlet 2029 and the outlet 2031. Droplet sizes within a range of 2microns and 3 microns may mitigate a risk of condensation during a disinfection cycle (e.g., within the disinfection device 2000 and/or within the CPAP mask 2002 and/or CPAP hose 2004), which may improve disinfection performance. Additionally, or alternatively, in some instances, one or more condensation reducers (e.g., mesh screen) may be included to reduce (e.g., prevent) condensation of droplets during a disinfection cycle (e.g., within the disinfection device 2000 and/or within the CPAP mask 2002 and/or CPAP hose 2004).

The piezo-electric atomizer 2028 may be an atomizer with a recessed dimple, wherein a distal end of a wick engaging the atomizer 2028 may be substantially planar such that consistent contact between the wick and the atomizer 2028 is encouraged. When the piezo-electric atomizer 2028 is an atomizer with a protruding dimple, a distal end of a wick engaging the atomizer 2028 may have a shape that corresponds to that of a cavity created by the protruding dimple such that consistent contact between the atomizer 2028 and the wick is encouraged. The wick for an atomizer with a recessed dimple may be harder (or more rigid) than the wick for an atomizer with a protruding dimple, which may improve a longevity of the wick and/or atomizer.

Ozonated air from the ozone generator 2008 is injected into the humidification chamber 2026 in a direction transverse to (e.g., perpendicular to) an emission direction of the piezo-electric atomizer 2028. The ozonated air may be injected such that the ozonated air has a turbulent flow (as opposed to a laminar flow) when entering the humidification chamber 2026.

The controller 2018 operates the pump 2012 and upstream fan 2014 according to the operation profile in order to obtain a desired environment within the disinfection chamber 2006 (e.g., quantity of ozone and/or relative humidity). For example, the pump 2012 may be operated to generate a flow rate of about 1.3 SLPM and the upstream fan 2014 may be operated to generate a flow rate of about 1.2 SLPM. In some instances, the disinfection chamber 2006 may be under vacuum or under pressure.

Figure 21:
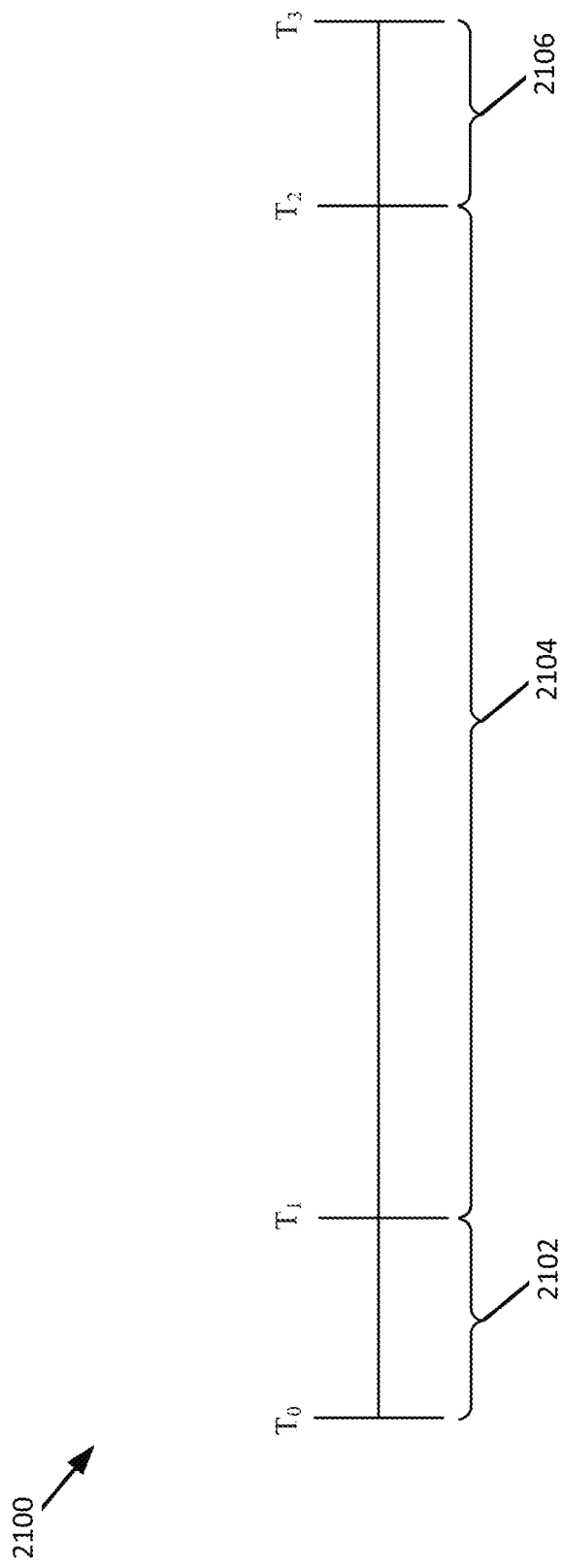
FIG. 21 shows a schematic example of an operational timeline for the disinfection device of FIG. 20, consistent with embodiments of the present disclosure.
Figure 24:
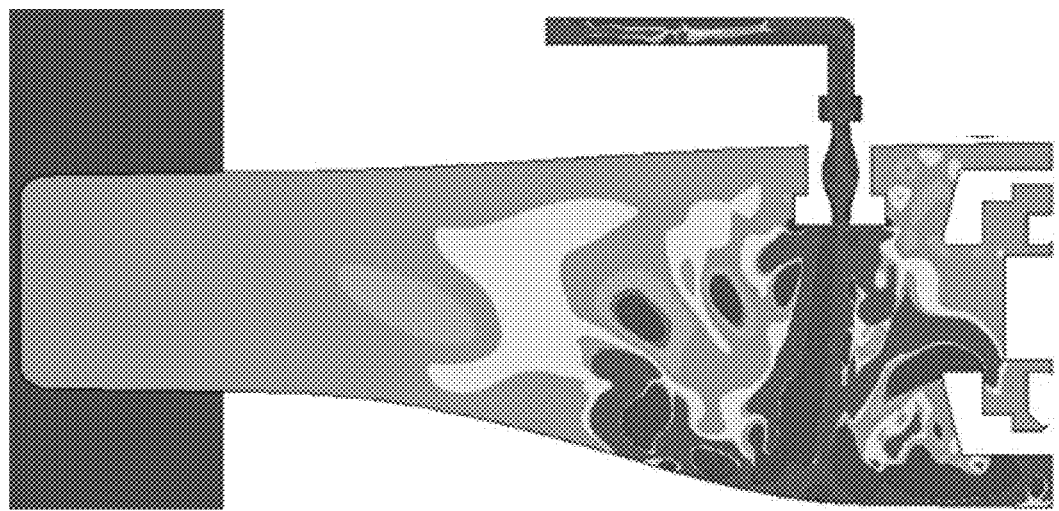
FIG. 24 shows another example of a flow diagram, consistent with embodiments of the present disclosure.
Figure 23:
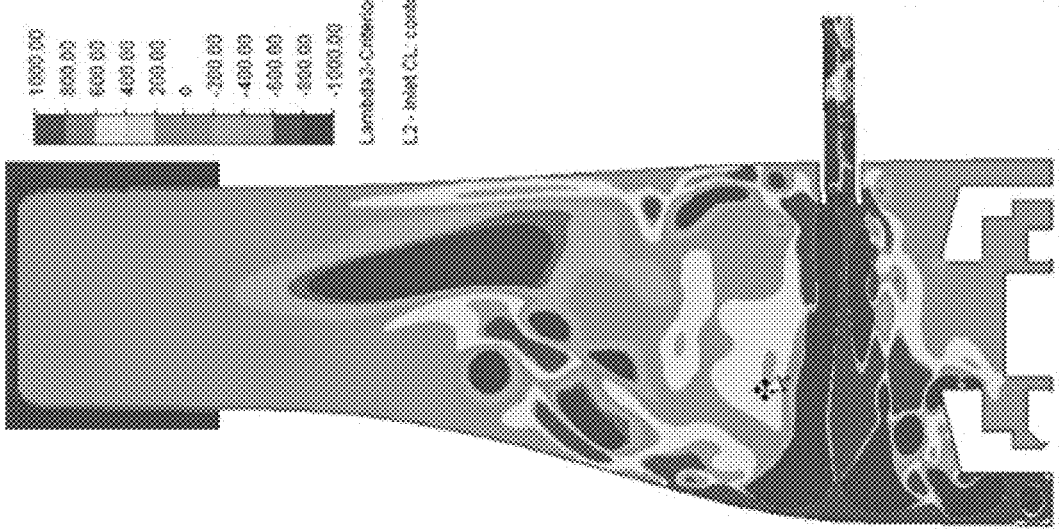
FIG. 23 shows another example of a flow diagram, consistent with embodiments of the present disclosure.
Figure 22:
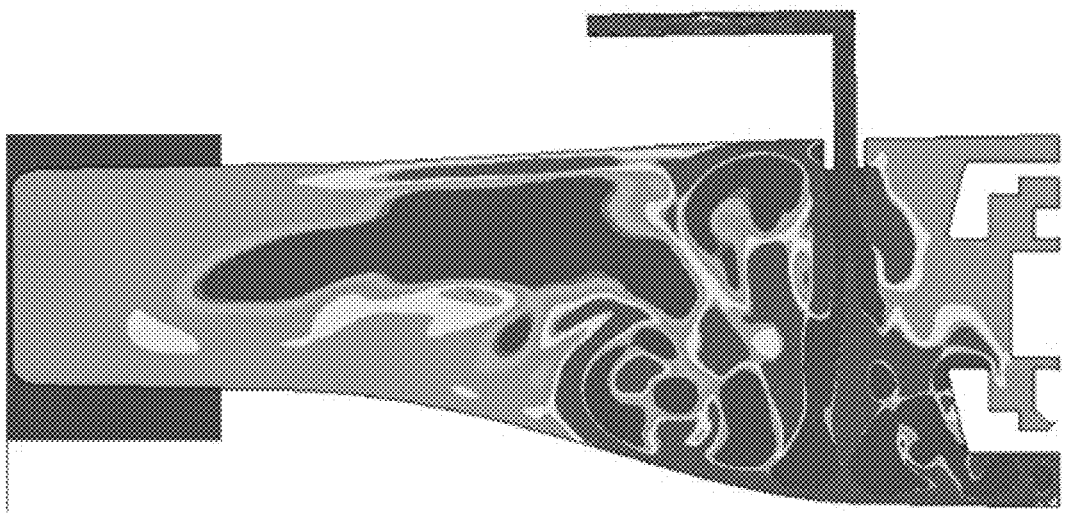
FIG. 22 shows an example of a flow diagram, consistent with embodiments of the present disclosure.

FIG. 21 shows a schematic example of an operational timeline 2100 of the disinfection device 2000 that corresponds to one example operation profile (e.g., a disinfection cycle) and is an example of the operational timeline 400 of FIG. 4.

As shown, a first period 2102 extends between time $T_0$ and time $T_1$, a second period 2104 extends between time $T_1$ and time $T_2$, and a third period 2106 extends between time $T_2$ and time $T_3$, wherein time $T_3$ is greater than time $T_2$, time $T_2$ is greater than time $T_1$, and time $T_1$ is greater than time $T_0$. In other words, the second period 2104 occurs between the first period 2102 and the third period 2106. The entire operation profile may have a duration in a range of, for example, 20 min to 120 min. By way of further example, the operation profile may have a duration of about 72 min.

The first period 2102 may generally be referred to as a period in which the ozone generator 2008 and/or and the humidifier 2010 are operated to achieve a desired initial condition (e.g., a desired humidity and/or ozone range) within the disinfection chamber 2006. The second period 2104 may generally be referred to as a period in which the ozone generator 2008 and/or the humidifier 2010 are operated to maintain a desired condition (e.g., a desired humidity and/or ozone range) within the disinfection chamber 2006. The third period 2106 may generally be referred to as the period in which the ozone generator 2008 and/or the humidifier 2010 are operated to purge the ozone from the disinfection chamber 2006 such that any residual ozone within the disinfection chamber 2006 is removed and/or within an acceptable level. The conditions within the disinfection chamber 2006 may be measured (e.g., using one or more sensors) and/or estimated.

During the first period 2102, the ozone generator 2008 generates ozone such that about 100 ppm to about 200 ppm of ozone is present in the disinfection chamber 2006 by the end of the first period 2102, the humidifier 2010 humidifies the environment within the disinfection chamber 2006 to about 70% relative humidity by the end of the first period 2102, the pump 2012 operates to generate a flow rate of about 1.3 SLPM, and the upstream fan 2014 operates to generate a flow rate of about 1.2 SLPM. The first period 2102 may have a duration in a range of, for example, about 1 minute to about 15 minutes. By way of further example, the first period 2102 may have a duration of about 6 minutes. During the first period 2102, the ozone generator 2008 and the humidifier 2010 may operate continuously. In some instances, one or more of the ozone generator 2008 and/or the humidifier 2010 may operate intermittently during the first period 2102. In these instances, the controller 2018 may be configured to determine whether to operate the ozone generator 2008 and/or the humidifier 2010 intermittently based, at least in part, on, for example, one or more sensed conditions within the disinfection chamber 2006.

During the second period 2104, the ozone generator 2008 operates intermittently (e.g., is pulsed according to a pulse rate), the humidifier 2010 is disabled, and the pump 2012 and upstream fan 2014 are operated to maintain a desired flow rate through the disinfection chamber 2006. The ozone generator 2008 may be operated intermittently according to a pulse rate having a constant period or a non-constant period. For example, the ozone generator 2008 may be enabled for a period in a range of 3 seconds to 15 seconds and disabled for a period in a range of 30 seconds to 90 seconds, wherein the ozone generator 2008 is cycled between being enabled and disabled for the duration of the second period 2104. By way of further example, the ozone generator 2008 may be enabled for a period of about 10 seconds and disabled for a period of about 65 seconds, wherein the ozone generator is cycled between being enabled and disabled for the duration of the second period 2104. The enabled period and the disabled period may be constant for the duration of the second period 2104 or at least one enabled period may have a different duration than at least one other enabled period and/or at least one disabled period may have a different duration than at least one other disabled period. Cycling of the ozone generator 2008 may be configured such that the quantity of ozone within the disinfection chamber 2006 is in a range of, for example, about 150 ppm to about 250 ppm. By way of further example, cycling of the ozone generator 2008 may be configured such that the quantity of ozone within the disinfection chamber 2006 is about 200 ppm.

During the second period, 2104 the pump 2012 operates to generate a flow rate of about 1.3 SLPM and the upstream fan 2014 operates to generate a flow rate of about 1.2 SLPM. The second period 2104 may have a duration in a range of, for example, about 15 minutes to about 120 minutes. By way of further example, the second period 2104 may have a duration of about 60 minutes. The flow rates of the pump 2012 and upstream fan 2014 may be such that the quantity of ozone and/or the relative humidity within the disinfection chamber 2006 stays within a predetermined acceptable range. One example of an acceptable range may include ozone within a range of about 100 ppm to about 285 ppm and/or relative humidity within a range of about 60% to about 99%.

During the third period 2106 the ozone generator 2008 and the humidifier 2010 are disabled and one or both of the pump 2012 and/or upstream fan 2014 are operated to urge at least a portion of the remaining ozone within the disinfection chamber 2006 through the ozone reduction filter 2016. For example, the pump 2012 and/or upstream fan 2014 may be operated until a quantity of ozone is at or below a predetermined threshold. During the third period 2106, the pump 2012 operates to generate a flow rate of about 1.3 SLPM and the upstream fan 2014 operates to generate a flow rate of about 1.2 SLPM. The third period 2106 may have a duration in a range of, for example, about 1 minute to about 20 minutes. By way of further example, the third period 2106 may have a duration of about 12 minutes.

The operation profile discussed in relation to FIG. 21 when carried out by the disinfection device 2000 of FIG. 20 results in the disinfection device 2000 achieving at least a 4-$Log_{10}$ (e.g., at least a 6-$Log_{10}$) kill rate. Through testing, it was determined that deviations in relative humidity (the quantity and how it is generated), quantity of ozone, and the flow rates of the pump 2012 and upstream fan 2014 from that described in relation to FIGS. 20 and 21 may result in a kill rate that was less than a 4-$Log_{10}$ kill rate.

Figure 25:
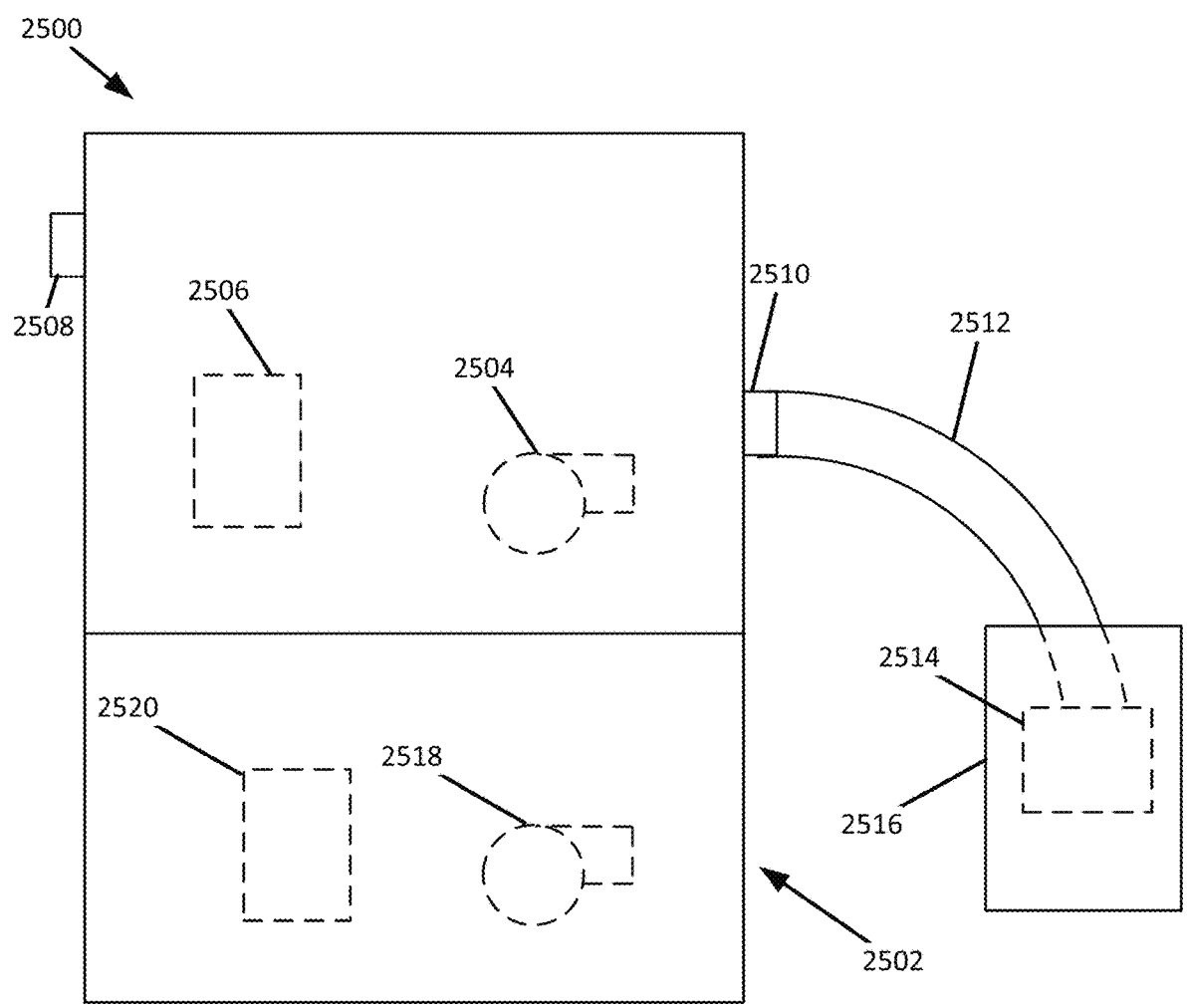
FIG. 25 shows a schematic example a CPAP device having a disinfection device, consistent with embodiments of the present disclosure.

FIG. 25 shows a schematic example a CPAP device 2500 having a disinfection device 2502. The disinfection device 2502 may be integrated with the CPAP device 2500 or separate from the CPAP device 2500. The CPAP device 2500 includes an air pump 2504, a CPAP water reservoir 2506, an environmental air inlet 2508 fluidly coupled to the air pump 2504, an air outlet 2510 fluidly coupled to the air inlet 2508, a CPAP hose 2512 fluidly coupled to the air outlet 2510, and a CPAP mask 2514 fluidly coupled to the CPAP hose 2512.

The CPAP device 2500 may have an operation mode and a disinfection mode. In the operation mode, the air pump 2504 urges air from the environment and through the CPAP hose 2512. The CPAP water reservoir 2506 is configured to add humidity to air flowing through the CPAP device 2500.

In the disinfection mode, the CPAP device 2500 may enable the disinfection device 2502 causing humidified ozonated air to flow through at least the CPAP hose 2512 and the CPAP mask 2514. In some instances, the humidified ozonated air may be caused to additionally flow through the CPAP water reservoir 2506. The humidified ozonated air may be generated and caused to flow in a manner consistent with any of the examples discussed herein. As such, for the sake of brevity, a detailed discussion of the generation and flowing of humidified ozonated air in the context of FIG. 25 is omitted.

When the disinfection mode is enabled, the CPAP device 2500 may be configured to be transitioned to a closed system. For example, the environmental air inlet 2508 may be closed (e.g., sealed) to substantially prevent the escape of ozone from the environmental air inlet and the CPAP mask 2514 may be disposed within a disinfection chamber 2516. The disinfection chamber 2516 may be coupled to the CPAP device 2500 or separate from the CPAP device 2500. For example, the disinfection chamber 2516 may be a disposable (or reusable) flexible bag that is ozone impermeable.

In some instances, any water within the CPAP water reservoir 2506 may be emptied prior to commencing the disinfection mode. For example, the disinfection device 2502 may include a water pump 2518 configured to transfer water from the CPAP water reservoir 2506. In this example, the water pump 2518 may transfer water to a disinfection water reservoir 2520 of the disinfection device 2502 such that the water can be used for humidifying ozonated air during the disinfection mode. In some instances, upon completion of the disinfection mode, the water in the disinfection water reservoir 2520 may be returned to the CPAP water reservoir 2506. As ozone may have become entrained within the water when in the disinfection water reservoir 2520 at least a portion of any pathogens in the water may be killed. In some instances, the CPAP water reservoir 2506 may be used as the disinfection water reservoir 2520.

Figure 26:
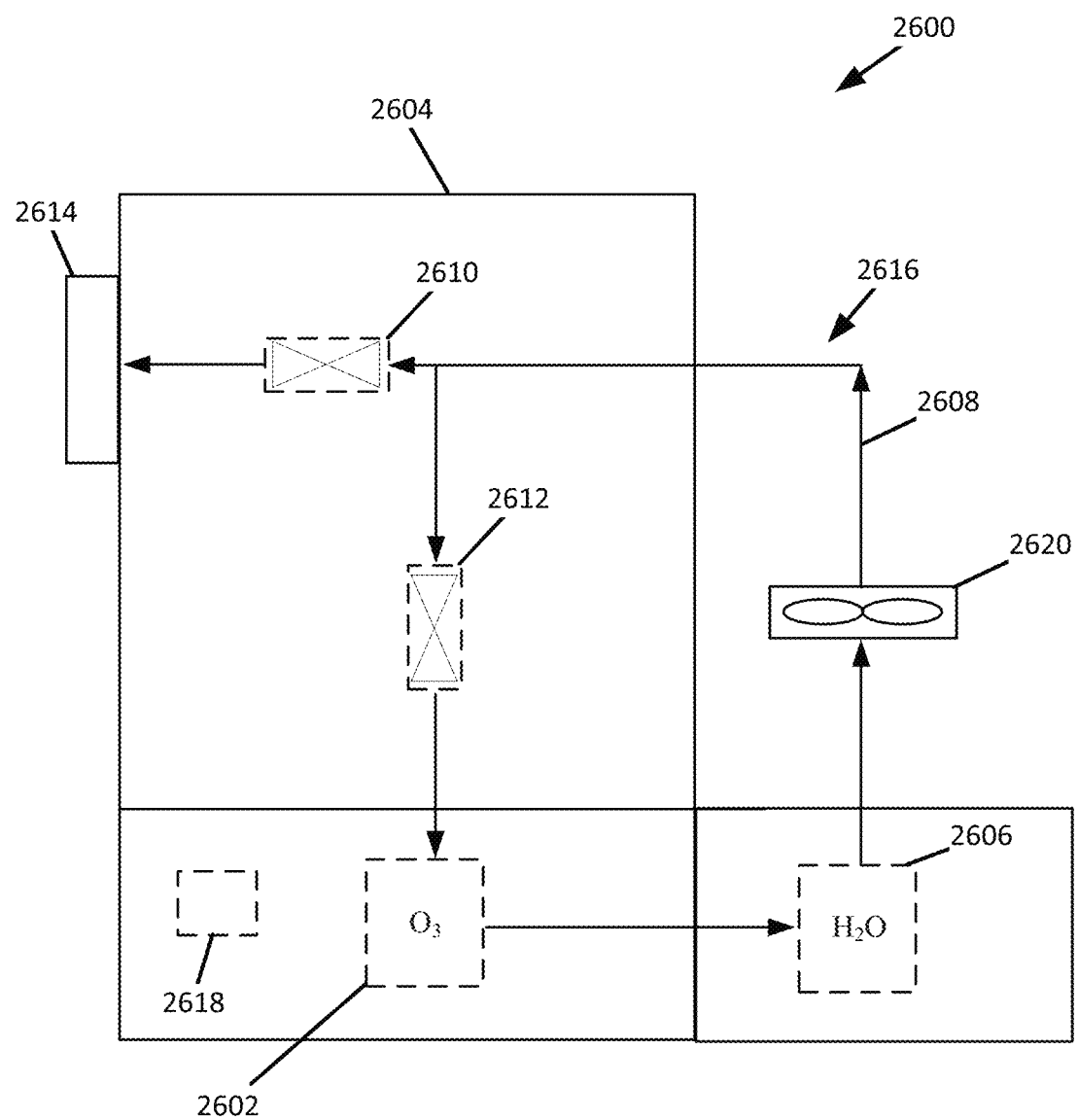
FIG. 26 shows a schematic example of a disinfection device with humidity control and a recirculation loop, consistent with embodiments of the present disclosure.

FIG. 26 is a schematic example of a disinfection device 2600 with humidity control and a recirculation loop. The disinfection device 2600 is an example of the disinfection device 200 of FIG. 2.

The disinfection device 2600 includes an ozone generator 2602, a disinfection chamber 2604, and a humidifier 2606. As shown, a flow path 2608 extends through the ozone generator 2602 through the humidifier 2606 and into the disinfection chamber 2604. The disinfection chamber 2604 may include one or more valves (e.g., a first valve 2610 and/or a second valve 2612). In some instances, the one or more valves may be two-way valves, three-valves, four-way valves, and/or any other valve configuration. For example, and as shown, the first valve 2610 is a two-way valve and the second valve 2612 is a two-way valve. In this example, the first valve 2610 is configured to selectively fluidly couple the flow path 2608 to a disinfection chamber outlet 2614 (which may include an ozone reduction filter) and the second valve 2612 may selectively fluidly couple the flow path 2608 to an inlet side of the ozone generator 2602 (selectively creating a recirculation loop 2616). A controller 2618 may be configured to selectively actuate the first and second valves 2610 and 2612 such that the recirculation loop 2616 can be selectively created during a disinfection cycle. The controller 2618 may further control a fan 2620 such that ozonated air flows along the flow path 2608.

Figure 27:
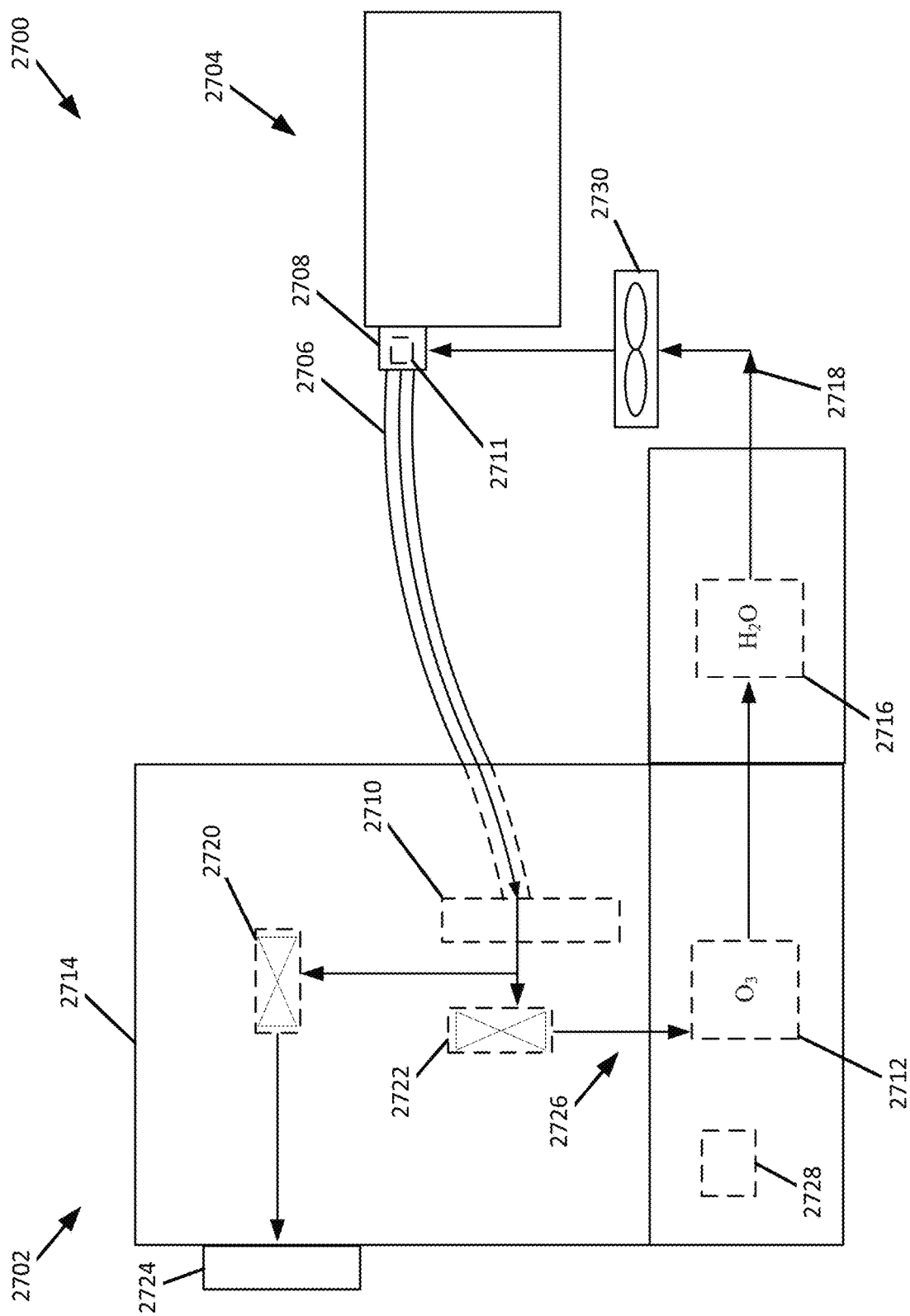
FIG. 27 shows a schematic example of a CPAP disinfection system, consistent with embodiments of the present disclosure.

FIG. 27 is a schematic example of a CPAP disinfection system 2700 having a disinfection device 2702, a CPAP machine 2704, a CPAP hose 2706 coupled to the CPAP machine 2704 via a disinfection adapter 2708, and a CPAP mask 2710 coupled to the CPAP hose 2706. The disinfection device 2702 is an example of the disinfection device 2600 of FIG. 26.

The disinfection adapter 2708 is configured to fluidly couple the CPAP hose 2706 and CPAP mask 2710 to the disinfection device 2702 and to fluidly couple the CPAP hose 2706 and the CPAP mask 2710 to the CPAP machine 2704. As such, a user may not have to remove the CPAP hose 2706 from the CPAP machine 2704 when disinfecting the CPAP hose 2706 and/or the CPAP mask 2710. In some instances, the disinfection adapter 2708 may include adapter valving 2711 configured selectively alter a flow path through the disinfection adapter 2708 (e.g., between a user mode in which the CPAP machine 2704 is fluidly coupled with the CPAP hose 2706 through the disinfection adapter 2708 and a disinfection mode in which the disinfection device 2702 is fluidly coupled with the CPAP hose 2706 through the disinfection adapter 2708). Such a configuration may substantially prevent ozone generated by the disinfection device 2702 from entering the CPAP machine 2704. In some instances, the CPAP machine 2704 may be operated during a disinfection cycle to substantially prevent ozone from entering the CPAP machine 2704.

The disinfection device 2702 includes an ozone generator 2712, a disinfection chamber 2714 configured to receive at least a portion of the CPAP hose 2706 and/or the CPAP mask 2710, and a humidifier 2716. As shown, a flow path 2718 extends through the ozone generator 2712 through the humidifier 2716 and into the disinfection chamber 2714 via the CPAP hose 2706 and the CPAP mask 2710. The disinfection chamber 2714 may include one or more valves (e.g., a first valve 2720 and/or a second valve 2722). In some instances, the one or more valves may be two-way valves, three-valves, four-way valves, and/or any other valve configuration. For example, and as shown, the first valve 2720 is a two-way valve and the second valve 2722 is a two-way valve. In this example, the first valve 2720 is configured to selectively fluidly couple the flow path 2718 to a disinfection chamber outlet 2724 (which may include an ozone reduction filter) and the second valve 2722 may selectively fluidly couple the flow path 2718 to an inlet side of the ozone generator 2712 (selectively creating a recirculation loop 2726). A controller 2728 may be configured to selectively actuate the first and second valves 2720 and 2722 such that the recirculation loop 2726 can be selectively created during a disinfection cycle. The controller 2728 may further control a fan 2730 such that ozonated air flows along the flow path 2718.

Figure 28:
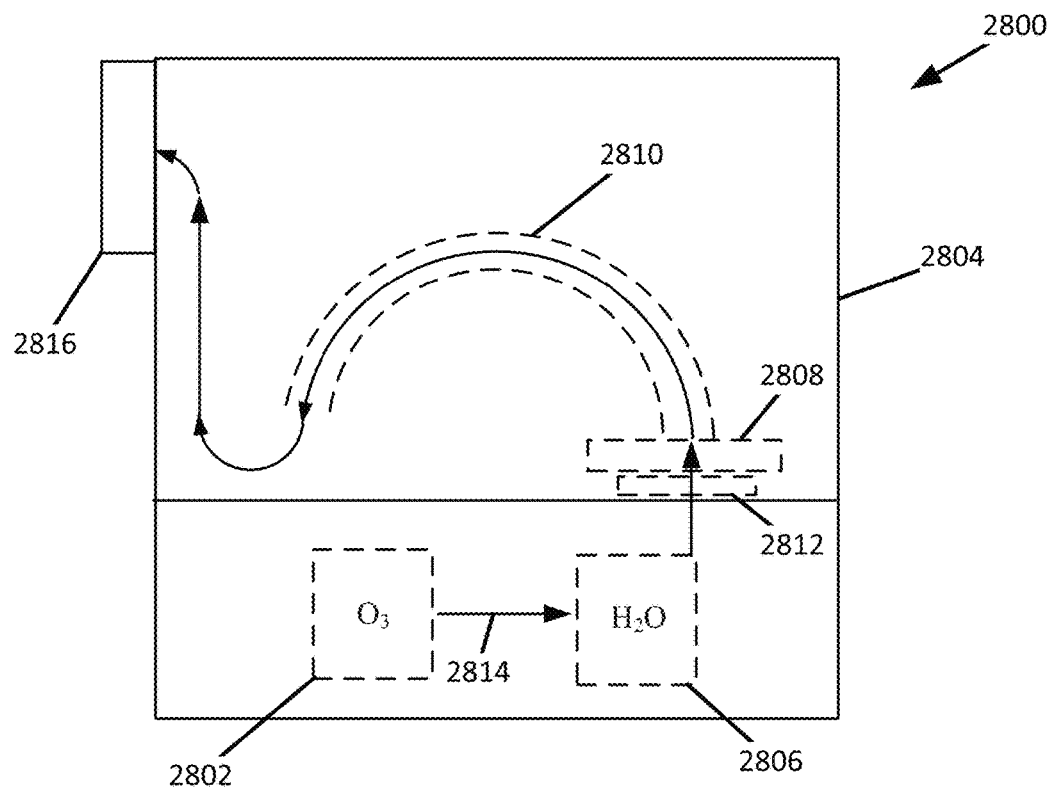
FIG. 28 shows a schematic example of a disinfection device, consistent with embodiments of the present disclosure.

FIG. 28 shows a schematic example of a disinfection device 2800, which is an example of the disinfection device 200 of FIG. 2.

The disinfection device 2800 includes an ozone generator 2802, a disinfection chamber 2804, and a humidifier 2806. The disinfection chamber 2804 is configured to receive a CPAP mask 2808 and/or a CPAP hose 2810. For example, the disinfection chamber 2804 may include a mask mount 2812. The mask mount 2812 may be fluidly coupled to the ozone generator 2802 and the humidifier 2806 and configured to removably couple to the CPAP mask 2808. As shown, the mask mount 2812 is downstream of the ozone generator 2802 and the humidifier 2806 and upstream of the CPAP hose 2810. As such, ozonated air (e.g., humidified ozonated air) comes into contact with the CPAP mask 2808 prior to coming into contact with the CPAP hose 2810. Such a configuration may improve disinfection at the CPAP mask 2808.

As shown, a flow path 2814 extends through the ozone generator 2802 through the humidifier 2806 and into the disinfection chamber 2804 via the mask mount 2812, the CPAP mask 2808, and the CPAP hose 2810. Once in the disinfection chamber 2804, the ozonated air may be recirculated or pass through a disinfection chamber outlet 2816.

Figure 29:
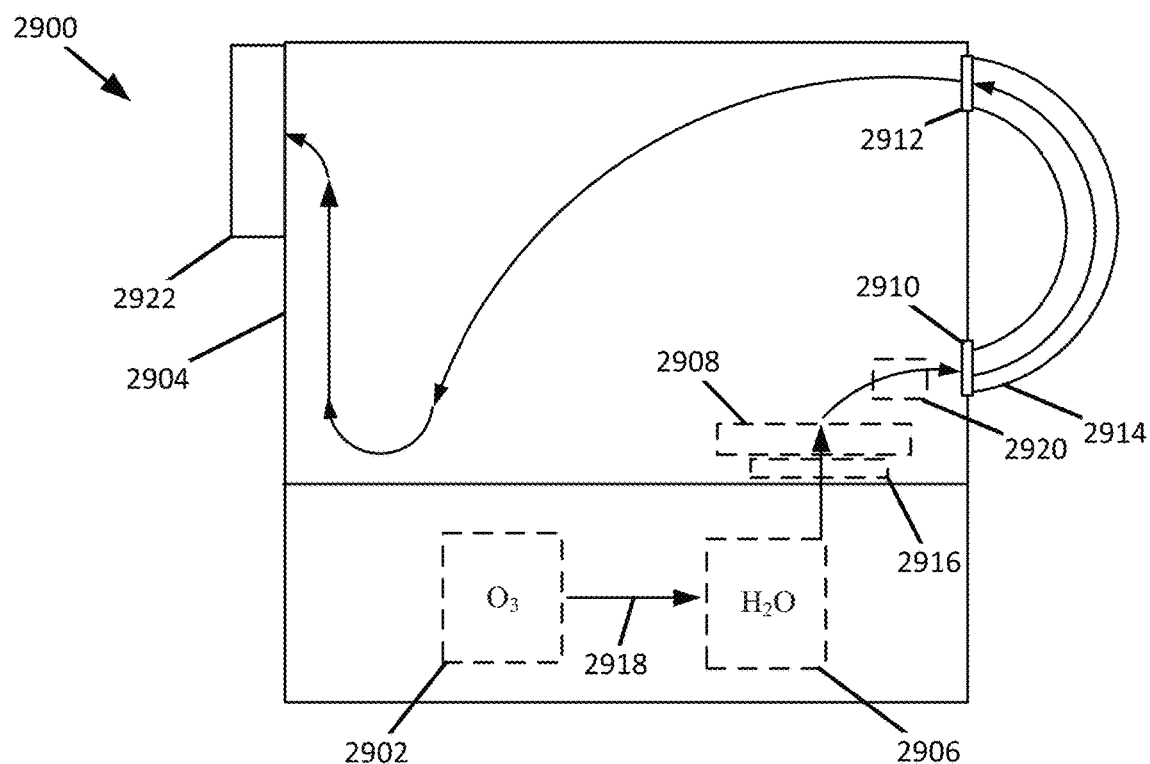
FIG. 29 shows a schematic example of a disinfection device, consistent with embodiments of the present disclosure.

FIG. 29 shows a schematic example of a disinfection device 2900, which is an example of the disinfection device 200 of FIG. 2.

The disinfection device 2900 includes an ozone generator 2902, a disinfection chamber 2904, and a humidifier 2906. The disinfection chamber 2904 is configured to receive a CPAP mask 2908. A first hose coupling 2910 and a second hose coupling 2912 are fluidly coupled to the disinfection chamber 2904 such that a CPAP hose 2914 that is external to the disinfection chamber 2904 can be fluidly coupled to the disinfection chamber 2904. The first and the second hose couplings 2910 and 2912 may be configured to detect whether a CPAP hose 2914 is coupled thereto such that the disinfection device 2900 is prevented from carrying out a disinfection cycle when the CPAP hose 2914 is not coupled to both the first and the second hose coupling 2910 and 2912.

The disinfection chamber 2904 may include a mask mount 2916. The mask mount 2916 may be fluidly coupled to the ozone generator 2902 and the humidifier 2906 and configured to removably couple to the CPAP mask 2908. As shown, the mask mount 2916 is downstream of the ozone generator 2902 and the humidifier 2906 and upstream of the CPAP hose 2914. As such, ozonated air (e.g., humidified ozonated air) comes into contact with the CPAP mask 2908 prior to coming into contact with the CPAP hose 2914. Such a configuration may improve disinfection at the CPAP mask 2908.

As shown, a flow path 2918 extends through the ozone generator 2902 through the humidifier 2906 and into the disinfection chamber 2904 via the mask mount 2916 and CPAP mask 2908. Once in the disinfection chamber 2904, the ozonated air may be urged to pass through the CPAP hose 2914 (e.g., using a fan 2920). After passing through the CPAP hose 2914, the ozonated air may be recirculated or pass through a disinfection chamber outlet 2922.

Figure 30:
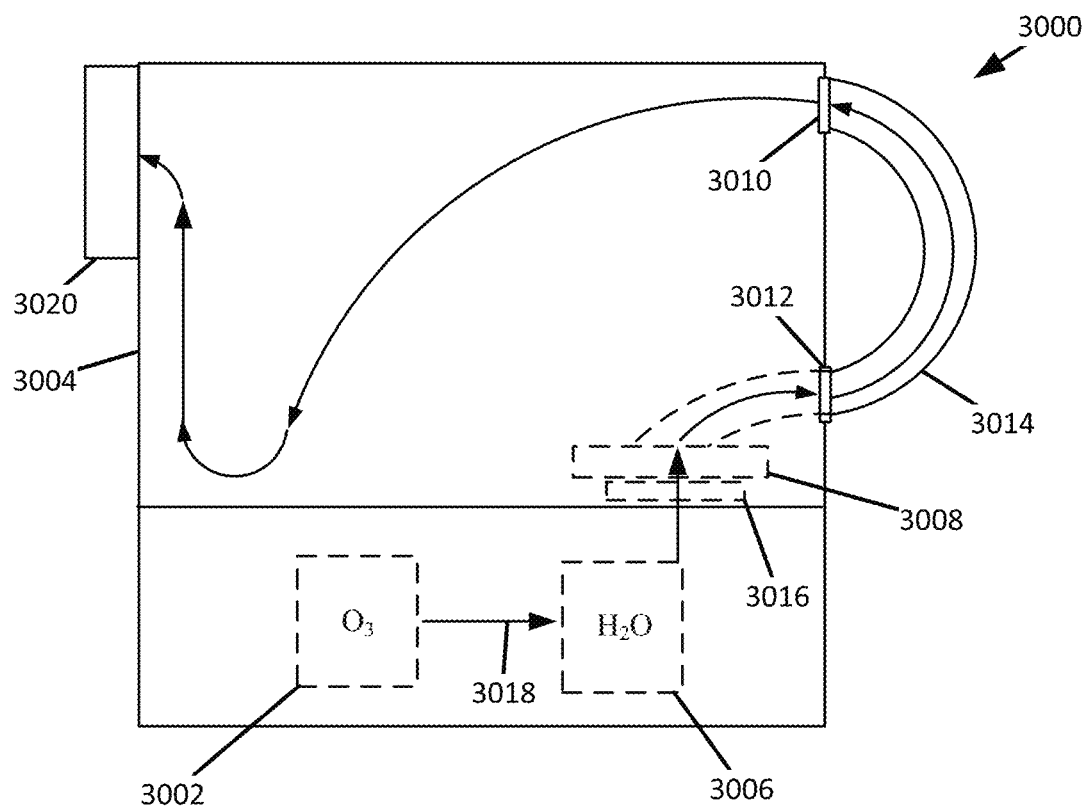
FIG. 30 shows a schematic example of a disinfection device, consistent with embodiments of the present disclosure.

FIG. 30 shows a schematic example of a disinfection device 3000, which is an example of the disinfection device 200 of FIG. 2.

The disinfection device 3000 includes an ozone generator 3002, a disinfection chamber 3004, and a humidifier 3006. The disinfection chamber 3004 is configured to receive a CPAP mask 3008. A hose coupling 3010 and a hose pass through 3012 are fluidly coupled to the disinfection chamber 3004 such that at least a portion of a CPAP hose 3014 is external to the disinfection chamber 2904 and at least a portion of the CPAP hose 3014 is disposed within the disinfection chamber 3004, while being fluidly coupled to the disinfection chamber 3004. The hose coupling 3010 and the hose passthrough 3012 may be configured to detect whether a CPAP hose 3014 is coupled thereto such that the disinfection device 3000 is prevented from carrying out a disinfection cycle when the CPAP hose 3014 is not coupled to both the hose coupling 3010 and the hose passthrough 3012.

The disinfection chamber 3004 may include a mask mount 3016. The mask mount 3016 may be fluidly coupled to the ozone generator 3002 and the humidifier 3006 and configured to removably couple to the CPAP mask 3008. As shown, the mask mount 3016 is downstream of the ozone generator 3002 and the humidifier 3006 and upstream of the CPAP hose 3014. As such, ozonated air (e.g., humidified ozonated air) comes into contact with the CPAP mask 3008 prior to coming into contact with the CPAP hose 3014. Such a configuration may improve disinfection at the CPAP mask 3008.

As shown, a flow path 3018 extends through the ozone generator 3002 through the humidifier 3006 and into the disinfection chamber 3004 via the mask mount 3016, the CPAP mask 3008, and the CPAP hose 3014. After passing through the CPAP hose 3014, the ozonated air may be recirculated or pass through a disinfection chamber outlet 3020.

Figure 31:
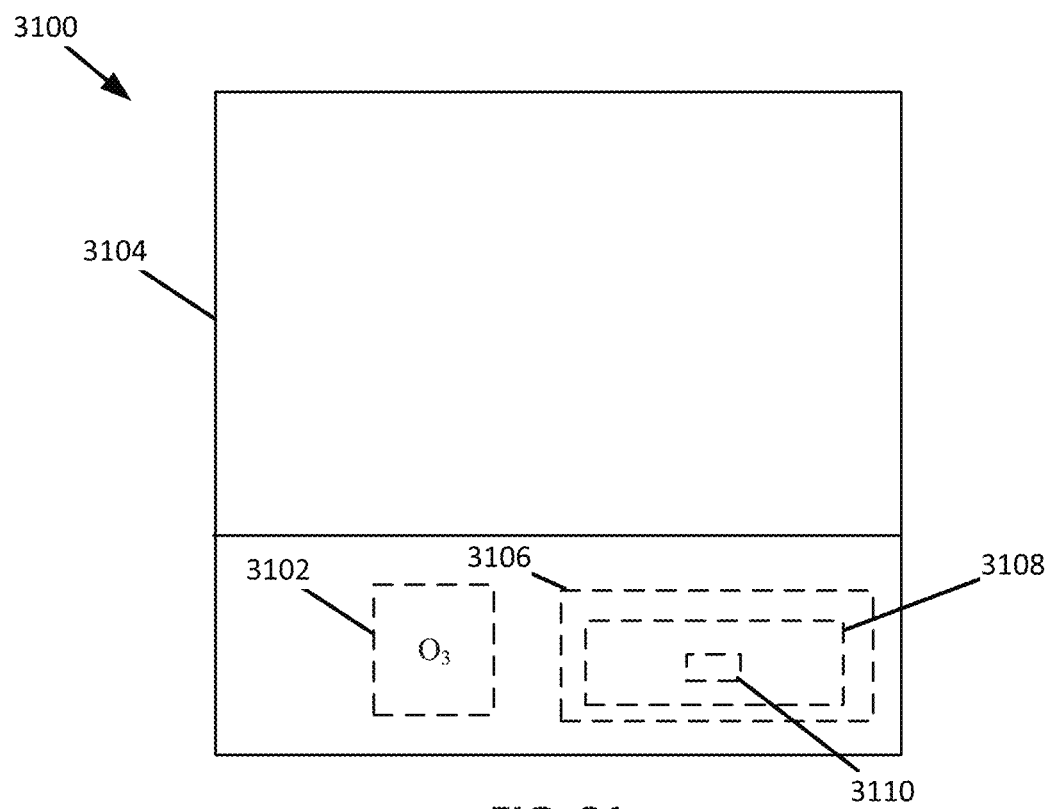
FIG. 31 shows a schematic example of a disinfection device, consistent with embodiments of the present disclosure.

FIG. 31 shows a schematic example of a disinfection device 3100, which is an example of the disinfection device 200 of FIG. 2.

The disinfection device 3100 includes an ozone generator 3102, a disinfection chamber 3104, and a humidifier 3106. The humidifier 3106 includes a water chamber 3108 and a bubbler 3110 within the water chamber 3108 that is configured to bubble ozonated air through water within the water chamber 3108. Bubbling of ozonated air through water may result in the addition of humidity to the ozonated air. The humidified ozonated air may enter the disinfection chamber 3104.

Figure 32:
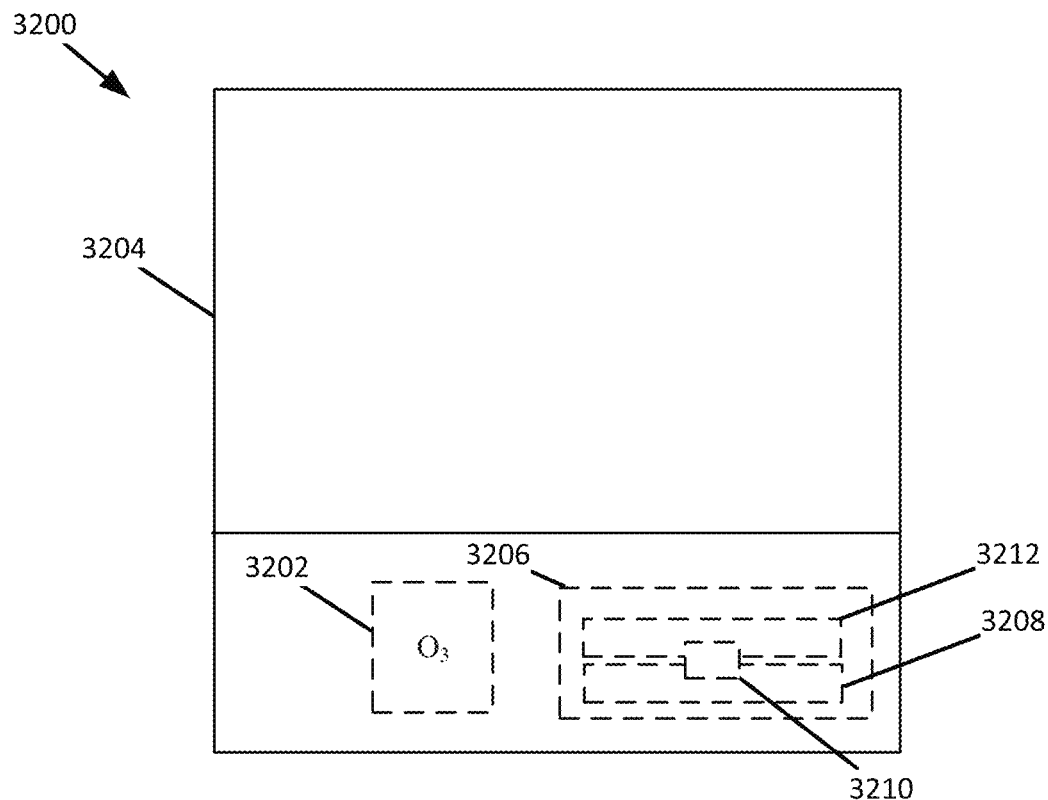
FIG. 32 shows a schematic example of a disinfection device, consistent with embodiments of the present disclosure.

FIG. 32 shows a schematic example of a disinfection device 3200, which is an example of the disinfection device 200 of FIG. 2.

The disinfection device 3200 includes an ozone generator 3202, a disinfection chamber 3204, and a humidifier 3206. The humidifier 3206 includes a water chamber 3208, an atomizer nozzle 3210 fluidly coupled to the water chamber 3208, and a humidification chamber 3212. The atomizer nozzle 3210 is configured to emit atomized water into the humidification chamber 3212 in a direction transverse to (e.g., perpendicular to) a flow of ozonated air entering the humidification chamber 3212 to humidify the ozonated air. The humidified ozonated air may enter the disinfection chamber 3204.

Figure 33:
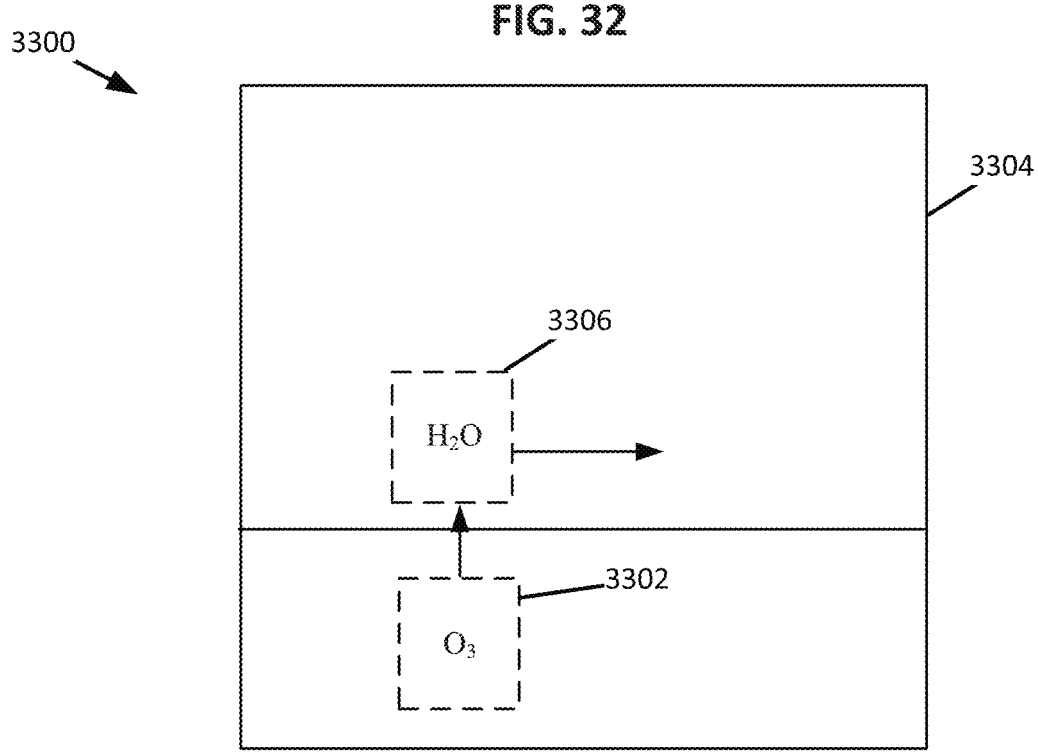
FIG. 33 shows a schematic example of a disinfection device, consistent with embodiments of the present disclosure.

FIG. 33 shows a schematic example of a disinfection device 3300, which is an example of the disinfection device 200 of FIG. 2. As shown, the disinfection device 3300 includes an ozone generator 3302, a disinfection chamber 3304, and a humidifier 3306. At least a portion of the humidifier 3306 is disposed within the disinfection chamber 3304. As such, the humidifier 3306 may be configured to emit humidified air and/or humidified ozonated air directly into the disinfection chamber 3304.

Figure 34:
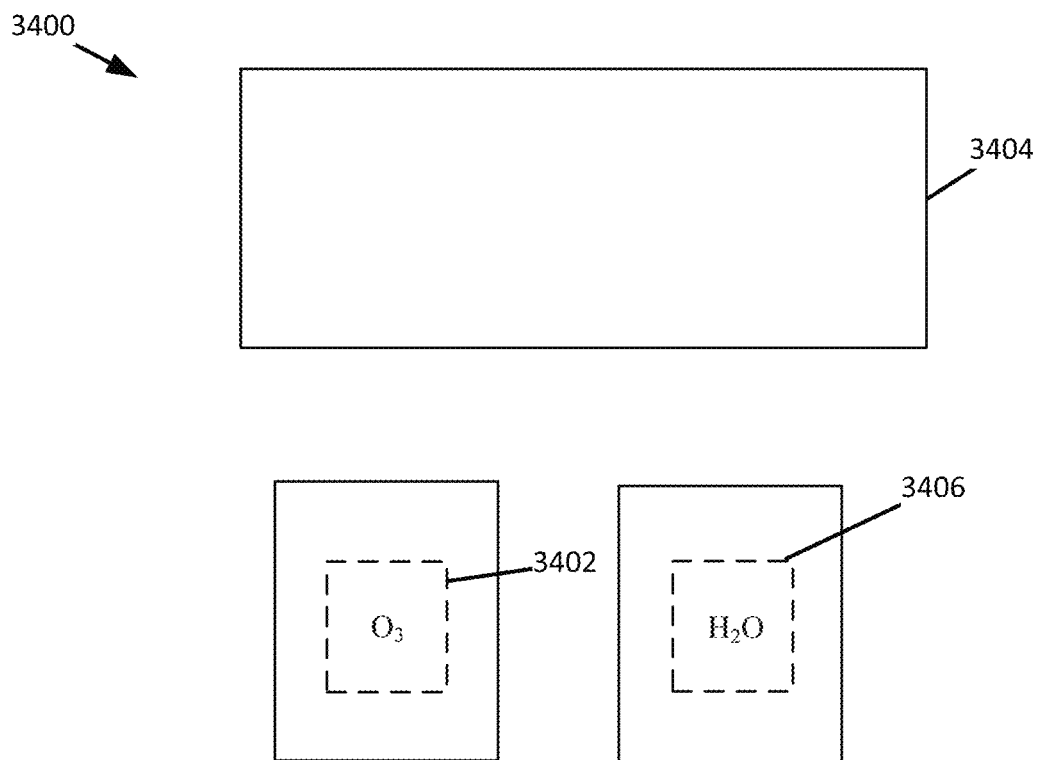
FIG. 34 shows a schematic example of a disinfection device, consistent with embodiments of the present disclosure

FIG. 34 shows a schematic example of a disinfection device 3400, which is an example of the disinfection device 200 of FIG. 2. As shown, the disinfection device 3400 includes an ozone generator 3402, a disinfection chamber 3404, and a humidifier 3406. As shown, the humidifier 3406 may be separate from one or more of the disinfection chamber 3404 and/or the ozone generator 3402. Such a configuration may allow, for example, the humidifier 3406 to be moved independently of one or more of the disinfection chamber 3404 and/or the ozone generator 3402. In some instances, such a configuration may allow the humidifier 3406 to be used as a module for a disinfection device 3400 which does not have a humidifier.

In some instances, the ozone generator 3402 and the humidifier 3406 may be coupled together and separate from the disinfection chamber 3404. Such a configuration may allow the ozone generator 3402 and the humidifier 3406 to be moved independently of the disinfection chamber 3404. In these instances, the disinfection chamber 3404 may be collapsible or compressible (e.g., a flexible bag).

Figure 35:
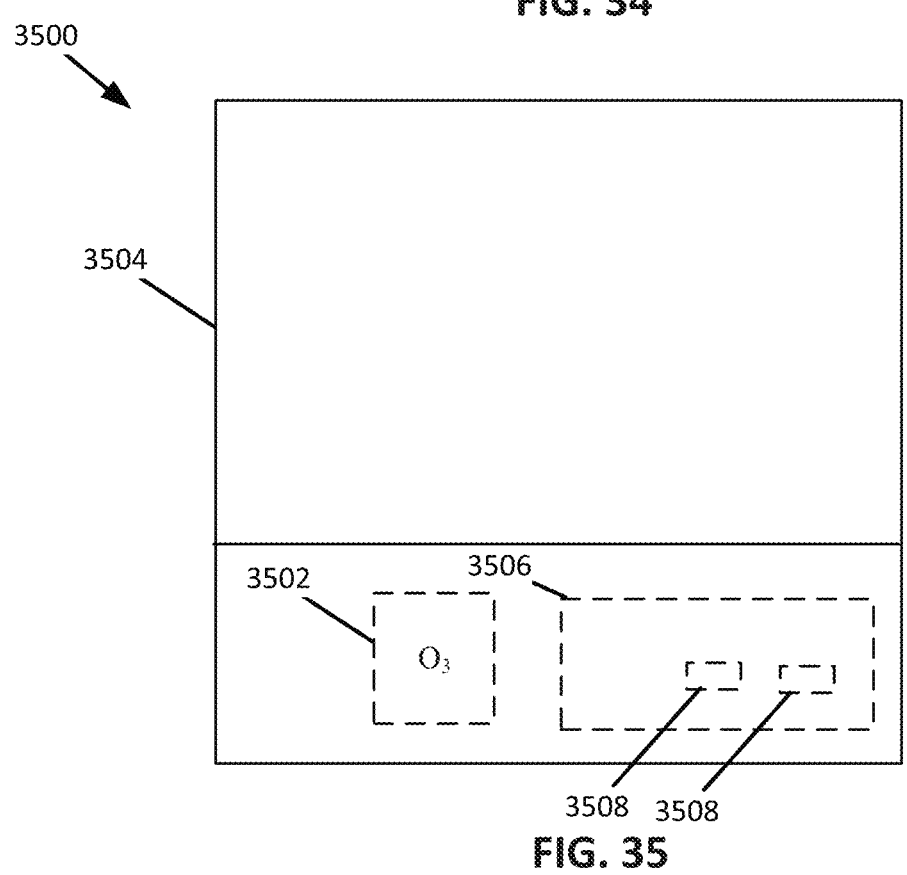
FIG. 35 shows a schematic example of a disinfection device, consistent with embodiments of the present disclosure.

FIG. 35 shows a schematic example of a disinfection device 3500, which is an example of the disinfection device 200 of FIG. 2. As shown, the disinfection device 3500 includes an ozone generator 3502, a disinfection chamber 3504, and a humidifier 3506. As shown, the humidifier 3506 includes a plurality of humidity generators 3508 (e.g., a plurality of atomizers and associated wicks).

Figure 36:
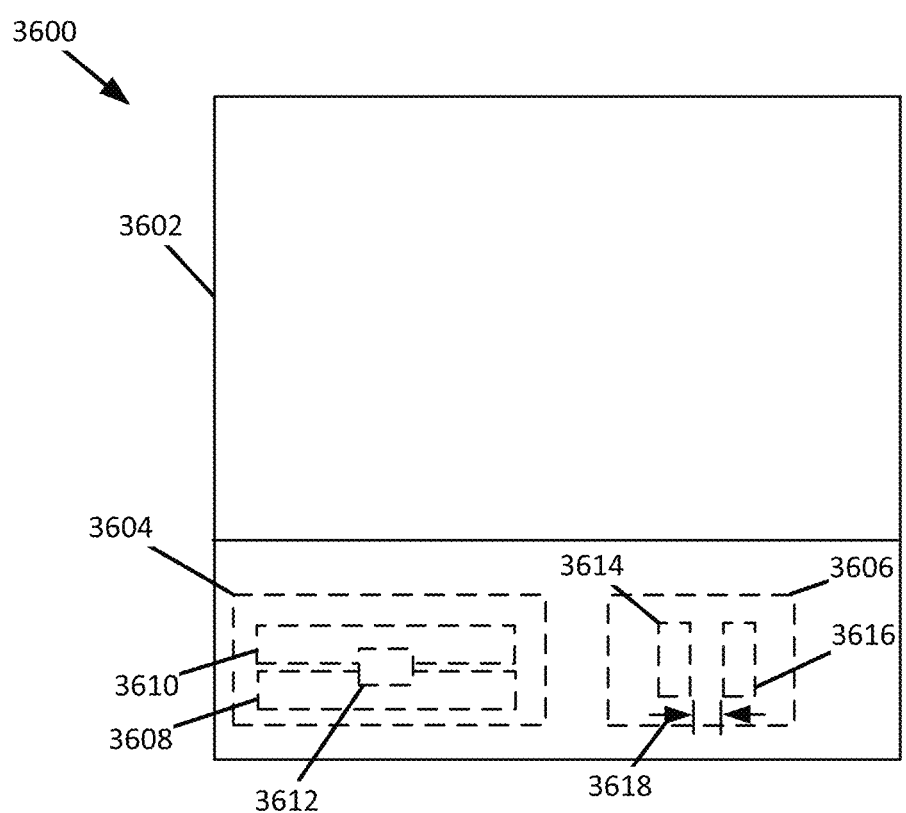
FIG. 36 shows a schematic example of a disinfection device, consistent with embodiments of the present disclosure.

FIG. 36 shows a schematic example of a disinfection device 3600. As shown, the disinfection device includes a disinfection chamber 3602, a humidifier 3604, and an electrolytic cell 3606. The humidifier 3604 includes a liquid reservoir 3608, a humidification chamber 3610, and a humidity generator 3612 configured to generate humidity within the humidification chamber 3610. The electrolytic cell 3606 is configured to generate hypochlorous acid and to emit the hypochlorous acid into the humidification chamber 3610 to mix with humidity generated by the humidity generator 3612. For example, the humidity generator 3612 may be configured to emit atomized water into the humidification chamber 3610 and the electrolytic cell 3606 may be configured to emit atomized hypochlorous acid into the humidification chamber 3610 such that the atomized water and the atomized hypochlorous acid mix. The electrolytic cell 3606 may be upstream or downstream of the humidity generator 3612 and/or the humidification chamber 3610. The mixing of hypochlorous acid with humidity may be accomplished in a similar manner as discussed herein in relation to ozone. As such, in some instances, one or more of the ozone based embodiments disclosed herein may use the electrolytic cell 3606 instead of (or in addition to) an ozone generator.

As shown, the electrolytic cell 3606 includes an anode 3614 and a cathode 3616 spaced apart by an anode-cathode separation distance 3618. The anode-cathode separation distance 3618 may be, for example, in a range of about 1 millimeter (mm) to about 10 mm. By way of further example, the anode-cathode separation distance 3618 may be in a range of about 2 mm to about 4 mm. A close proximity of the anode 3614 to the cathode 3616 may encourage generation of hypochlorous acid.

In response to a current running between the anode 3614 and the cathode 3616 in the presence of water, the electrolytic cell 3606 may generate hypochlorous acid. In some instances, use of chlorinated water may improve the generation of hypochlorous acid.

The mixing of hypochlorous acid with humidity may be accomplished in a similar manner as discussed herein in relation to ozone. As such, in some instances, one or more of the ozone based embodiments disclosed herein may use the electrolytic cell 3606 instead of (or in addition to) an ozone generator. As such, ozone and hypochlorous acid may be generally referred to herein as a disinfection fluid which may be generated by a disinfection fluid generator (e.g., an electrolytic cell, such that the electrolytic cell 3606, or an ozone generator, such as the ozone generator 202). In other words, the embodiments disclosed in relation to, for example, FIGS. 1-36 utilize at least one disinfection fluid to achieve a desired level of disinfection performance.

The disinfection fluid described herein may be used as a disinfectant for a variety of home or industrial products including but not limited to: dentistry and orthodontic appliances and equipment, surgical tools, ventilators, respirators, nebulizers, hospital equipment, rooms, toys, daycare appliances, baby products (e.g. bottles, pumps, pump equipment, pacifiers), kitchen equipment, fruits and vegetables, sports equipment and apparel and other uses where the systems and methods described herein may readily be incorporated into a disinfection device and improve disinfection of an object over existing disinfection methods.

An example of a disinfection device, consistent with the present disclosure, may include a disinfection chamber, a disinfection fluid generator (e.g., an ozone generator and/or an electrolytic cell) configured to generate a disinfection fluid, and a humidifier fluidly coupled to the disinfection chamber and the disinfection fluid generator, the humidifier being downstream of the disinfection fluid generator and upstream of the disinfection chamber.

In some instances, the humidifier may include a piezoelectric atomizer configured to generate droplets having a droplet size in a range of about 1.5 microns to about 4.5 microns. In some instances, the piezo-electric atomizer may be configured to generate droplets having a droplet size of about 2.5 microns. In some instances, the piezo-electric atomizer may include a protective coating. In some instances, the humidifier may include an inlet connector configured to introduce a turbulent flow to air passing therethrough and an outlet downstream of the inlet connector. In some instances, air may exit the inlet connector along an injection axis and the humidifier further includes an atomizer having an emission axis, the emission axis extending transverse to the injection axis. In some instances, the emission axis may be substantially perpendicular to the injection axis. In some instances, the humidifier may include a liquid reservoir, a wick assembly removably coupled to the liquid reservoir, and a piezo-electric atomizer configured to engage the wick assembly. In some instances, the humidifier may include a liquid reservoir access that includes a carriage for receiving the liquid reservoir, the carriage being configured to move along an insertion axis and a coupling axis, the coupling axis extending transverse to the insertion axis. In some instances, movement of the carriage along the coupling axis may move the wick assembly into and out of engagement with the piezo-electric atomizer. In some instances, the humidifier may include a humidification chamber and an atomizer, the humidification chamber having a bottom wall, a top wall, and one or more sidewalls extending between the bottom wall and the top wall, wherein the atomizer is coupled to the bottom wall. In some instances, at least a portion of the top wall may be sloped to direct liquid condensed thereon in a direction of at least one of the one or more sidewalls such that the liquid flows down the at least one of the one or more sidewalls to collect on the bottom wall.

An example of a disinfection device, consistent with the present disclosure, may include a disinfection chamber, an ozone generator, and a humidifier fluidly coupled to the disinfection chamber and the ozone generator, the humidifier being downstream of the ozone generator and upstream of the disinfection chamber.

In some instances, the humidifier may include a piezo-electric atomizer configured to generate droplets having a droplet size in a range of about 1.5 microns to about 4.5 microns. In some instances, the piezo-electric atomizer may be configured to generate droplets having a droplet size of about 2.5 microns. In some instances, the piezo-electric atomizer may include a protective coating. In some instances, the humidifier may include an inlet connector configured to introduce a turbulent flow to air passing therethrough and an outlet downstream of the inlet connector. In some instances, air may exit the inlet connector along an injection axis and the humidifier further includes an atomizer having an emission axis, the emission axis extending transverse to the injection axis. In some instances, the emission axis may be substantially perpendicular to the injection axis. In some instances, the humidifier may include a liquid reservoir, a wick assembly removably coupled to the liquid reservoir, and a piezo-electric atomizer configured to engage the wick assembly. In some instances, the humidifier may include a liquid reservoir access that includes a carriage for receiving the liquid reservoir, the carriage being configured to move along an insertion axis and a coupling axis, the coupling axis extending transverse to the insertion axis. In some instances, movement of the carriage along the coupling axis may move the wick assembly into and out of engagement with the piezo-electric atomizer. In some instances, the humidifier may include a humidification chamber and an atomizer, the humidification chamber having a bottom wall, a top wall, and one or more sidewalls extending between the bottom wall and the top wall, wherein the atomizer is coupled to the bottom wall. In some instances, at least a portion of the top wall may be sloped to direct liquid condensed thereon in a direction of at least one of the one or more sidewalls such that the liquid flows down the at least one of the one or more sidewalls to collect on the bottom wall.

Another example of a disinfection device, consistent with the present disclosure, may include a disinfection chamber, an ozone generator, and a humidifier fluidly coupled to the disinfection chamber and the ozone generator, the humidifier including a liquid reservoir, a humidification chamber, and a piezo-electric atomizer configured to emit atomized droplets into the humidification chamber along an emission axis.

In some instances, piezo-electric atomizer may be configured to generate droplets having a droplet size in a range of about 1.5 microns to about 4.5 microns. In some instances, the piezo-electric atomizer may be configured to generate droplets having a droplet size of about 2.5 microns. In some instances, the piezo-electric atomizer may include a protective coating. In some instances, the humidifier may include an inlet connector configured to introduce a turbulent flow to air passing therethrough and an outlet downstream of the inlet connector. In some instances, air may exit the inlet connector along an injection axis that extends transverse to the emission axis. In some instances, the emission axis may be substantially perpendicular to the injection axis. In some instances, the humidifier may include a wick assembly removably coupled to the liquid reservoir and configured to engage the piezo-electric atomizer. In some instances, the humidifier may include a liquid reservoir access that includes a carriage for receiving the liquid reservoir, the carriage being configured to move along an insertion axis and a coupling axis, the coupling axis extending transverse to the insertion axis. In some instances, movement of the carriage along the coupling axis may move a wick assembly into and out of engagement with the piezo-electric atomizer. In some instances, the humidification chamber may include a bottom wall, a top wall, and one or more sidewalls extending between the bottom wall and the top wall, wherein the piezo-electric atomizer is coupled to the bottom wall. In some instances, at least a portion of the top wall may be sloped to direct liquid condensed thereon in a direction of at least one of the one or more sidewalls such that the liquid flows down the at least one of the one or more sidewalls to collect on the bottom wall. In some instances, liquid collected on the bottom wall may be returned to the liquid reservoir.

Another example of a disinfection device, consistent with the present disclosure, may include a disinfection chamber having a disinfection chamber outlet, an ozone reduction filter fluidly coupled to the disinfection chamber outlet, an ozone generator, and a humidifier fluidly coupled to the disinfection chamber and the ozone generator. The humidifier may include a liquid reservoir, a humidification chamber having an inlet connector configured to introduce a turbulent flow to air passing therethrough and an outlet downstream of the inlet connector, and a piezo-electric atomizer configured to emit atomized droplets into the humidification chamber along an emission axis.

In some instances, the inlet connector may include a connector inlet axis and a connector outlet axis, the connector inlet axis extending transverse to the connector outlet axis. In some instances, the connector inlet axis may be perpendicular to the connector outlet axis. In some instances, the piezo-electric atomizer may include a protective coating. In some instances, the piezo-electric atomizer may be configured to generate droplets having a droplet size in a range of about 1.5 microns to about 4.5 microns.

Another example of a disinfection device, consistent with the present disclosure, may include a disinfection chamber, an ozone generator, and a humidifier fluidly coupled to the disinfection chamber and the ozone generator such that the humidifier is downstream of the ozone generator and upstream of the disinfection chamber, the humidifier including a piezo-electric atomizer.

In some instances, the piezo-electric atomizer may include a protective coating. In some instances, the protective coating may have a thickness in a range of about 2 microns to about 12 microns. In some instances, the protective coating may be a Parylene coating. In some instances, the protective coating may be hydrophobic. In some instances, the piezo-electric atomizer may include a hydrophobic coating. In some instances, the piezo-electric atomizer may be formed from one or more durable materials. In some instances, the piezo-electric atomizer may include a protective coating. In some instances, the humidifier may include a piezo-electric atomizer configured to generate droplets having a droplet size in a range of about 1.5 microns to about 4.5 microns. In some instances, the piezo-electric atomizer may be configured to generate droplets having a droplet size of about 2.5 microns. In some instances, the piezo-electric atomizer may include a protective coating. In some instances, the humidifier may include an inlet connector configured to introduce a turbulent flow to air passing therethrough and an outlet downstream of the inlet connector. In some instances, air may exit the inlet connector along an injection axis that extends transverse to an emission axis of the piezo-electric atomizer. In some instances, the emission axis may be substantially perpendicular to the injection axis. In some instances, the humidifier may include a liquid reservoir, a wick assembly removably coupled to the liquid reservoir and configured to engage the piezo-electric atomizer. In some instances, the humidifier may include a liquid reservoir access that includes a carriage for receiving the liquid reservoir, the carriage being configured to move along an insertion axis and a coupling axis, the coupling axis extending transverse to the insertion axis. In some instances, movement of the carriage along the coupling axis may move the wick assembly into and out of engagement with the piezo-electric atomizer. In some instances, the humidifier may include a humidification chamber having a bottom wall, a top wall, and one or more sidewalls extending between the bottom wall and the top wall, wherein the atomizer is coupled to the bottom wall. In some instances, at least a portion of the top wall may be sloped to direct liquid condensed thereon in a direction of at least one of the one or more sidewalls such that the liquid flows down the at least one of the one or more sidewalls to collect on the bottom wall.

Another example of a disinfection device, consistent with the present disclosure, may include a disinfection chamber, an ozone generator, and a humidifier fluidly coupled to the disinfection chamber and the ozone generator, the humidifier including a liquid reservoir, a humidification chamber, and a piezo-electric atomizer fluidly coupled to the liquid reservoir and configured to emit atomized droplets into the humidification chamber along an emission axis.

In some instances, the piezo-electric atomizer may include a protective coating. In some instances, the protective coating may have a thickness in a range of about 2 microns to about 12 microns. In some instances, the protective coating may be a Parylene coating. In some instances, the protective coating may be hydrophobic. In some instances, the piezo-electric atomizer may include a hydrophobic coating. In some instances, the piezo-electric atomizer may be formed from one or more durable materials. In some instances, the piezo-electric atomizer may include a protective coating. In some instances, the piezo-electric atomizer may be configured to generate droplets having a droplet size in a range of about 1.5 microns to about 4.5 microns. In some instances, the piezo-electric atomizer may be configured to generate droplets having a droplet size of about 2.5 microns. In some instances, the piezo-electric atomizer may include a protective coating.

Another example of a disinfection device, consistent with the present disclosure, may include a disinfection chamber, an ozone generator fluidly coupled to the disinfection chamber, a humidifier fluidly coupled to the disinfection chamber and the ozone generator, the humidifier being downstream of the ozone generator and upstream of the disinfection chamber, and a controller configured to control operation of the ozone generator and the humidifier according to a disinfection cycle.

In some instances, the disinfection cycle may include a first period, a second period, and a third period, wherein during the first period the controller causes the both the ozone generator and the humidifier to operate concurrently. In some instances, the humidifier may be disabled during the second period. In some instances, during the second period, the controller may selectively enable and disable the ozone generator, causing the ozone generator to generate ozone pulses. In some instances, the humidifier and the ozone generator may be disabled during the third period. In some instances, to generate the ozone pulses, the controller may alternate between enabling the ozone generator for about 10 seconds and disabling the ozone generator for about 65 seconds. In some instances, the controller may be configured to cause the ozone generator to generate the ozone pulses at a pulse rate, wherein the pulse rate is configured such that a quantity of ozone within the disinfection chamber is in a range of about 80 parts-per-million (ppm) to about 150 ppm. In some instances, the first period may be about 6 minutes, the second period may be about 72 minutes, and the third period may be about 12 minutes. In some instances, during the first period, the controller may operate the humidifier such that a relative humidity within the disinfection chamber is in a range of about 65% to about 99%. In some instances, the first period may occur before the second period and the second period may occur before the third period. In some instances, the second period may be longer than both the third period and the first period. In some instances, the first period may be shorter than the third period.

Another example of a disinfection device, consistent with the present disclosure, may include a disinfection chamber, an ozone generator fluidly coupled to the disinfection chamber, a pump fluidly coupled to the ozone generator and upstream of the ozone generator, a fan fluidly coupled to the ozone generator and downstream of the ozone generator, a humidifier fluidly coupled to the disinfection chamber and the ozone generator, the humidifier being downstream of the ozone generator and upstream of the disinfection chamber, and a controller configured to control operation of the ozone generator, the humidifier, the pump, and the fan according to a disinfection cycle, the disinfection cycle including a first period, a second period, and a third period.

In some instances, the controller may cause the fan to operate at a fan flow rate and the pump to operate at a pump flow rate, the pump flow rate being different from the fan flow rate during at least one of the first period, the second period, and/or the third period. In some instances, the fan flow rate may be less than the pump flow rate during the first period and the second period. In some instances, a ratio of the fan flow rate to the pump flow rate during the first period and the second period may be about 0.9. In some instances, the fan flow rate may be greater than the pump flow rate during the third period. In some instances, the pump flow rate may be in a range of about 1 standard liter per minute (SLPM) to about 1.6 SLPM during the first period and the second period. In some instances, the fan flow rate may be about 0.1 SLPM to about 0.15 SLPM less than the pump flow rate during the first period and the second period. In some instances, during the first period the controller may cause the both the ozone generator and the humidifier to operate concurrently. In some instances, the humidifier may be disabled during the second period. In some instances, during the second period, the controller may selectively enable and disable the ozone generator, causing the ozone generator to generate ozone pulses. In some instances, the humidifier and the ozone generator may be disabled during the third period. In some instances, to generate the ozone pulses, the controller may alternate between enabling the ozone generator for about 10 seconds and disabling the ozone generator for about 65 seconds. In some instances, the controller may be configured to cause the ozone generator to generate the ozone pulses at a pulse rate, wherein the pulse rate is configured such that a quantity of ozone within the disinfection chamber is in a range of about 80 parts-per-million (ppm) to about 150 ppm. In some instances, the first period may be about 6 minutes, the second period may be about 72 minutes, and the third period may be about 12 minutes. In some instances, during the first period, the controller may operate the humidifier such that a relative humidity within the disinfection chamber is in a range of about 65% to about 99%. In some instances, the first period may occur before the second period and the second period may occur before the third period. In some instances, the second period may be longer than both the third period and the first period. In some instances, the first period may be shorter than the third period.

Another example of a disinfection device, consistent with the present disclosure, may include a disinfection chamber, an ozone generator, and a humidifier fluidly coupled to the disinfection chamber and the ozone generator, the humidifier including a humidification chamber and a liquid reservoir.

In some instances, the humidification chamber may include a bottom wall, a top wall, and one or more sidewalls extending between the bottom wall and the top wall. In some instances, at least a portion of the top wall may be sloped to direct liquid condensed thereon in a direction of at least one of the one or more sidewalls such that the liquid flows down the at least one of the one or more sidewalls to collect on the bottom wall. In some instances, liquid collected on the bottom wall may be returned to the liquid reservoir. In some instances, the humidifier may further include a piezo-electric atomizer coupled to the bottom wall and configured to emit atomized droplets along an emission axis that extends in a direction of the top wall. In some instances, the piezo-electric atomizer may be configured to generate droplets having a droplet size in a range of about 1.5 microns to about 4.5 microns. In some instances, the piezo-electric atomizer may be configured to generate droplets having a droplet size of about 2.5 microns. In some instances, the piezo-electric atomizer may include a protective coating. In some instances, the humidification chamber may include an inlet connector configured to introduce a turbulent flow to air passing therethrough and an outlet downstream of the inlet connector. In some instances, air may exit the inlet connector along an injection axis and the humidifier further includes an atomizer having an emission axis, the emission axis extending transverse to the injection axis. In some instances, the emission axis may be substantially perpendicular to the injection axis. In some instances, the humidifier may further include a wick assembly removably coupled to the liquid reservoir and a piezo-electric atomizer configured to engage the wick assembly. In some instances, the humidifier may further include a liquid reservoir access that includes a carriage for receiving the liquid reservoir, the carriage being configured to move along an insertion axis and a coupling axis, the coupling axis extending transverse to the insertion axis. In some instances movement of the carriage along the coupling axis may move the wick assembly into and out of engagement with the piezo-electric atomizer.

Another example of a disinfection device, consistent with the present disclosure, may include a disinfection chamber, an ozone generator fluidly coupled to the disinfection chamber, a humidifier fluidly coupled to the disinfection chamber and the ozone generator, the humidifier being downstream of the ozone generator and upstream of the disinfection chamber, and a controller configured to control operation of the ozone generator and the humidifier, wherein the controller is configured to cause the both the ozone generator and the humidifier to operate concurrently for a first period of time and to cause the ozone generator to operate independent of the humidifier for a second period of time.

In some instances, the second period of time may be greater than the first period of time. In some instances, the humidifier may include an inlet connector configured to introduce a turbulent flow to air passing therethrough and an outlet downstream of the inlet connector. In some instances, air may exit the inlet connector along an injection axis and the humidifier further includes an atomizer having an emission axis, the emission axis extending transverse to the injection axis. In some instances, the emission axis may be substantially perpendicular to the injection axis. In some instances, the humidifier may include a liquid reservoir, a wick assembly removably coupled to the liquid reservoir, and a piezo-electric atomizer configured to engage the wick assembly. In some instances, the humidifier may include a liquid reservoir access that includes a carriage for receiving the liquid reservoir, the carriage being configured to move along an insertion axis and a coupling axis, the coupling axis extending transverse to the insertion axis. In some instances, movement of the carriage along the coupling axis may move the wick assembly into and out of engagement with the piezo-electric atomizer. In some instances, the humidifier may further include a humidification chamber having a bottom wall, a top wall, and one or more sidewalls extending between the bottom wall and the top wall, wherein the atomizer is coupled to the bottom wall. In some instances, the top wall may be sloped to direct liquid condensed thereon in a direction of at least one of the one or more sidewalls such that the liquid flows down the at least one of the one or more sidewalls to collect on the bottom wall. In some instances, liquid collected on the bottom wall may be returned to the liquid reservoir.

An example of a disinfection device for cleaning one or more components of a continuous positive airway pressure (CPAP) machine, consistent with the present disclosure, may include a disinfection chamber, an ozone generator fluidly coupled to the disinfection chamber, a humidifier fluidly coupled to the ozone generator, the humidifier being downstream of the ozone generator, a CPAP hose fluidly coupling the humidifier to the disinfection chamber, and a controller configured to control operation of the ozone generator and the humidifier.

In some instances, the controller may be configured to cause the both the ozone generator and the humidifier to operate concurrently for a first period of time and to cause the ozone generator to operate independent of the humidifier for a second period of time, the second period of time being greater than the first period of time. In some instances, the humidifier may include an inlet connector configured to introduce a turbulent flow to air passing therethrough and an outlet downstream of the inlet connector. In some instances, air may exit the inlet connector along an injection axis and the humidifier further includes an atomizer having an emission axis, the emission axis extending transverse to the injection axis. In some instances, the emission axis may be substantially perpendicular to the injection axis. In some instances, the humidifier may include a liquid reservoir, a wick assembly removably coupled to the liquid reservoir, and a piezo-electric atomizer configured to engage the wick assembly. In some instances, the humidifier may include a liquid reservoir access that includes a carriage for receiving the liquid reservoir, the carriage being configured to move along an insertion axis and a coupling axis, the coupling axis extending transverse to the insertion axis. In some instances, movement of the carriage along the coupling axis may move the wick assembly into and out of engagement with the piezo-electric atomizer. In some instances, the humidifier may further include a humidification chamber having a bottom wall, a top wall, and one or more sidewalls extending between the bottom wall and the top wall, wherein the atomizer is coupled to the bottom wall. In some instances, the top wall may be sloped to direct liquid condensed thereon in a direction of at least one of the one or more sidewalls such that the liquid flows down the at least one of the one or more sidewalls to collect on the bottom wall. In some instances, liquid collected on the bottom wall may be returned to the liquid reservoir.

An example of a humidifier for use with a disinfection device, consistent with the present disclosure, may include an atomizer, a liquid reservoir, and a humidification chamber, the atomizer configured to emit atomized liquid from the liquid reservoir into the humidification chamber, the humidification chamber having a bottom wall, a top wall, and one or more sidewalls extending between the bottom wall and the top wall, at least a portion of the top wall is sloped to direct liquid condensed thereon in a direction of at least one of the one or more sidewalls such that the liquid flows down the at least one of the one or more sidewalls to collect on the bottom wall.

In some instances, liquid collected on the bottom wall may be returned to the liquid reservoir. In some instances, the atomizer may be coupled to the bottom wall of the humidification chamber. In some instances, the atomizer may be configured to emit atomized droplets along an emission axis that extends in a direction of the top wall. In some instances, the humidification chamber may include an inlet connector configured to introduce a turbulent flow to air passing therethrough and an outlet downstream of the inlet connector. In some instances, air may exit the inlet connector along an injection axis, the injection axis extending transverse to the emission axis. In some instances, the emission axis may be substantially perpendicular to the injection axis. In some instances, the atomizer may be configured to generate droplets having a droplet size in a range of about 1.5 microns to about 4.5 microns. In some instances, the atomizer may be configured to generate droplets having a droplet size of about 2.5 microns. In some instances, the atomizer may be a piezo-electric atomizer. In some instances, the atomizer may include a protective coating. In some instances, the humidifier may further include a wick assembly removably coupled to the liquid reservoir and the atomizer is a piezo-electric atomizer that is configured to engage the wick assembly. In some instances, the humidifier may further include a liquid reservoir access that includes a carriage for receiving the liquid reservoir, the carriage being configured to move along an insertion axis and a coupling axis, the coupling axis extending transverse to the insertion axis.

Another example of a disinfection device, consistent with the present disclosure, may include a disinfection chamber, an ozone generator configured to generate ozone, and a humidifier configured to generate humidity and configured to be fluidly coupled to the disinfection chamber and the ozone generator, the humidifier being configured to encourage a mixing of generated ozone with generated humidity.

In some instances, the disinfection chamber may be fluidly coupled to the humidifier via a continuous positive air pressure (CPAP) hose. In some instances, a first hose end of the CPAP hose may be coupled to the humidifier and a second hose end of the CPAP hose may be coupled to a CPAP mask, the disinfection chamber being configured to receive the CPAP mask. In some instances, the humidifier may include a liquid reservoir, a humidification chamber, and a humidity generator, the humidity generator configured to urge liquid from the liquid reservoir into the humidification chamber. In some instances, the humidity generator may include an atomizer. In some instances, the atomizer may be configured to generate droplets having a droplet size in a range of about 1.5 microns to about 4.5 microns. In some instances, the atomizer may be configured to generate droplets having a droplet size of about 2.5 microns. In some instances, the ozone generator may be configured to generate a quantity of ozone in a range of about 200 parts-per-million (ppm) to about 300 ppm. In some instances, the humidifier may be downstream of the ozone generator and may include an inlet connector configured to introduce a turbulent flow to air passing therethrough. In some instances, the mixing of generated ozone with generated humidity may result in at least a portion of the generated ozone becoming entrained within droplets of moisture generated by the humidifier. In some instances, a pump may be fluidly coupled to the disinfection chamber at location upstream of the disinfection chamber and a fan may be fluidly coupled to the disinfection chamber at a location downstream of the disinfection chamber. In some instances, for at least a portion of a disinfection cycle, the fan may be operated at a fan flow rate and the pump may be operated at a pump flow rate, the fan flow rate may be less than the pump flow rate.

Another example of a disinfection device, consistent with the present disclosure, may include a disinfection chamber configured to receive a continuous positive air pressure (CPAP) mask and at least a portion of a CPAP hose, an ozone generator configured to generate ozone, and a humidifier configured to generate humidity and configured to be fluidly coupled to the disinfection chamber and the ozone generator, the humidifier being configured to encourage a mixing of generated ozone with generated humidity.

In some instances, the disinfection chamber may be fluidly coupled to the humidifier via the CPAP hose. In some instances, a first hose end of the CPAP hose may be coupled to the humidifier and a second hose end of the CPAP hose may be coupled to the CPAP mask. In some instances, the humidifier may include a liquid reservoir, a humidification chamber, and a humidity generator, the humidity generator configured to urge liquid from the liquid reservoir into the humidification chamber. In some instances, the humidity generator may include an atomizer. In some instances, the atomizer may be configured to generate droplets having a droplet size in a range of about 1.5 microns to about 4.5 microns. In some instances, the atomizer may be configured to generate droplets having a droplet size of about 2.5 microns. In some instances, the ozone generator may be configured to generate a quantity of ozone in a range of about 200 parts-per-million (ppm) to about 300 ppm. In some instances, the humidifier may be downstream of the ozone generator and may include an inlet connector configured to introduce a turbulent flow to air passing therethrough. In some instances, the mixing of generated ozone with generated humidity may result in at least a portion of the generated ozone becoming entrained within droplets of moisture generated by the humidifier. In some instances, a pump may be fluidly coupled to the disinfection chamber at location upstream of the disinfection chamber and a fan may be fluidly coupled to the disinfection chamber at a location downstream of the disinfection chamber. In some instances, for at least a portion of a disinfection cycle, the fan may be operated at a fan flow rate and the pump may be operated at a pump flow rate, the fan flow rate may be less than the pump flow rate.

Another example of a disinfection device, consistent with the present disclosure, may include a disinfection chamber configured to receive a continuous positive air pressure (CPAP) mask, the disinfection chamber including a hose passthrough configured such that a CPAP hose can pass therethrough, an ozone generator configured to generate ozone, a humidifier configured to generate humidity and configured to be fluidly coupled to the disinfection chamber and the ozone generator, the humidifier being configured to encourage a mixing of generated ozone with generated humidity such that at least a portion of the generated ozone becomes entrained within droplets of moisture generated by the humidifier, wherein a first end of the CPAP hose is coupled to the humidifier and a second end of the CPAP hose is coupled to the CPAP mask, a pump fluidly coupled to the disinfection chamber at location upstream of the disinfection chamber, and a fan fluidly coupled to the disinfection chamber at a location downstream of the disinfection chamber, wherein, for at least a portion of a disinfection cycle, the fan is operated at a fan flow rate and the pump is operated at a pump flow rate, the fan flow rate being less than the pump flow rate.

In some instances, the humidifier may include a liquid reservoir, a humidification chamber, and an atomizer. In some instances, the atomizer may be configured to generate droplets having a droplet size in a range of about 1.5 microns to about 4.5 microns. In some instances, the atomizer may be configured to generate droplets having a droplet size of about 2.5 microns. In some instances, the ozone generator may be configured to generate a quantity of ozone in a range of about 200 parts-per-million (ppm) to about 300 ppm. In some instances, the humidifier may be downstream of the ozone generator and includes an inlet connector configured to introduce a turbulent flow to air passing therethrough.

Another example of a disinfection device, consistent with the present disclosure, may include a disinfection chamber, an ozone generator, and a humidifier configured to generate humidity and configured to be fluidly coupled to the disinfection chamber and the ozone generator, the humidifier being configured to encourage a mixing of generated ozone with generated humidity.

In some instances, the humidifier may include a humidity generator configured to generate droplets having a droplet size in a range of about 1.5 microns to about 4.5 microns. In some instances, the humidity generator may be configured to generate droplets having a droplet size of about 2.5 microns. In some instances, the humidity generator may include a protective coating. In some instances, the humidifier may include an inlet connector configured to introduce a turbulent flow to air passing therethrough and an outlet downstream of the inlet connector. In some instances, air may exit the inlet connector along an injection axis and the humidifier may further include an atomizer having an emission axis, the emission axis extending transverse to the injection axis. In some instances, the emission axis may be substantially perpendicular to the injection axis. In some instances, the humidifier may include a liquid reservoir, a wick assembly removably coupled to the liquid reservoir, and a piezo-electric atomizer configured to engage the wick assembly. In some instances, the humidifier may include a liquid reservoir access that includes a carriage for receiving the liquid reservoir, the carriage being configured to move along an insertion axis and a coupling axis, the coupling axis extending transverse to the insertion axis. In some instances, movement of the carriage along the coupling axis may move the wick assembly into and out of engagement with the piezo-electric atomizer. In some instances, the humidifier may include a humidification chamber and an atomizer, the humidification chamber having a bottom wall, a top wall, and one or more sidewalls extending between the bottom wall and the top wall, wherein the atomizer is coupled to the bottom wall. In some instances, at least a portion of the top wall may be sloped to direct liquid condensed thereon in a direction of at least one of the one or more sidewalls such that the liquid flows down the at least one of the one or more sidewalls to collect on the bottom wall.

Another example of a disinfection device, consistent with the present disclosure, may include a disinfection chamber, an ozone generator, and a humidifier fluidly coupled to the ozone generator and configured to be fluidly coupled to the disinfection chamber via a continuous positive air pressure (CPAP) hose, the humidifier including a liquid reservoir, a humidification chamber, and a humidity generator.

In some instances, the humidity generator may be configured to generate droplets having a droplet size in a range of about 1.5 microns to about 4.5 microns. In some instances, the humidity generator may be configured to generate droplets having a droplet size of about 2.5 microns. In some instances, the humidity generator may include a protective coating. In some instances, the humidifier may include an inlet connector configured to introduce a turbulent flow to air passing therethrough and an outlet downstream of the inlet connector. In some instances, air may exit the inlet connector along an injection axis that extends transverse to an emission axis of the humidity generator. In some instances, the emission axis may be substantially perpendicular to the injection axis. In some instances, the humidifier may further include a wick assembly removably coupled to the liquid reservoir. In some instances, the humidifier may include a liquid reservoir access that includes a carriage for receiving the liquid reservoir, the carriage being configured to move along an insertion axis and a coupling axis, the coupling axis extending transverse to the insertion axis. In some instances, movement of the carriage along the coupling axis may move a wick assembly into and out of engagement with a liquid disperser of the humidity generator. In some instances, the humidification chamber may include a bottom wall, a top wall, and one or more sidewalls extending between the bottom wall and the top wall, wherein at least a portion of the humidity generator is coupled to the bottom wall. In some instances, at least a portion of the top wall may be sloped to direct liquid condensed thereon in a direction of at least one of the one or more sidewalls such that the liquid flows down the at least one of the one or more sidewalls to collect on the bottom wall. In some instances, liquid collected on the bottom wall may be returned to the liquid reservoir.

Another example of a disinfection device, consistent with the present disclosure, may include a disinfection chamber having a disinfection chamber outlet, an ozone reduction filter fluidly coupled to the disinfection chamber outlet, an ozone generator, and a humidifier fluidly coupled to the disinfection chamber and the ozone generator. The humidifier may include a liquid reservoir, a humidification chamber having an inlet connector configured to introduce a turbulent flow to air passing therethrough and an outlet downstream of the inlet connector, and a humidity generator configured to emit droplets into the humidification chamber along an emission axis.

In some instances, the inlet connector may include a connector inlet axis and a connector outlet axis, the connector inlet axis extending transverse to the connector outlet axis. In some instances, the connector inlet axis may be perpendicular to the connector outlet axis. In some instances, the humidity generator may include a protective coating. In some instances, humidity generator may be configured to generate droplets having a droplet size in a range of about 1.5 microns to about 4.5 microns.

Another example of a disinfection device, consistent with the present disclosure, may include a disinfection chamber, an ozone generator, and a humidifier fluidly coupled to the disinfection chamber and the ozone generator, the humidifier including a humidity generator having a protective coating.

In some instances, the humidity generator may include a piezo-electric atomizer. In some instances, the protective coating may have a thickness in a range of about 2 microns to about 12 microns. In some instances, the protective coating may be a Parylene coating. In some instances, the protective coating may be hydrophobic. In some instances, the humidifier may include a piezo-electric atomizer configured to generate droplets having a droplet size in a range of about 1.5 microns to about 4.5 microns. In some instances, the piezo-electric atomizer may be configured to generate droplets having a droplet size of about 2.5 microns. In some instances, the piezo-electric atomizer may include the protective coating. In some instances, the humidifier may include an inlet connector configured to introduce a turbulent flow to air passing therethrough and an outlet downstream of the inlet connector. In some instances, air may exit the inlet connector along an injection axis that extends transverse to an emission axis of the humidity generator. In some instances, the emission axis may be substantially perpendicular to the injection axis. In some instances, the humidifier may include a liquid reservoir, a wick assembly removably coupled to the liquid reservoir. In some instances, the humidifier may include a liquid reservoir access that includes a carriage for receiving the liquid reservoir, the carriage being configured to move along an insertion axis and a coupling axis, the coupling axis extending transverse to the insertion axis. In some instances, movement of the carriage along the coupling axis may move the wick assembly into and out of engagement with a liquid disperser of the humidity generator. In some instances, the humidifier may include a humidification chamber having a bottom wall, a top wall, and one or more sidewalls extending between the bottom wall and the top wall and wherein at least a portion of the humidity generator is coupled to the bottom wall. In some instances, at least a portion of the top wall may be sloped to direct liquid condensed thereon in a direction of at least one of the one or more sidewalls such that the liquid flows down the at least one of the one or more sidewalls to collect on the bottom wall.

Another example of a disinfection device, consistent with the present disclosure, may include a disinfection chamber, an ozone generator, and a humidifier fluidly coupled to the ozone generator and configured to be fluidly coupled to disinfection chamber via a continuous positive air pressure (CPAP) hose, the humidifier including a liquid reservoir, a humidification chamber, and humidity generator fluidly coupled to the liquid reservoir and configured to emit droplets into the humidification chamber along an emission axis.

In some instances, the humidity generator may include a protective coating. In some instances, the protective coating may have a thickness in a range of about 2 microns to about 12 microns. In some instances, the protective coating may be a Parylene coating. In some instances, the protective coating may be hydrophobic. In some instances, the humidity generator may include a piezo-electric atomizer having a protective coating. In some instances, humidity generator may be configured to generate droplets having a droplet size in a range of about 1.5 microns to about 4.5 microns. In some instances, the humidity generator may be configured to generate droplets having a droplet size of about 2.5 microns. In some instances, the humidity generator may include a piezo-electric atomizer having a protective coating. In some instances, the disinfection chamber may be configured to receive a CPAP mask coupled to the CPAP hose.

Another example of a disinfection device, consistent with the present disclosure, may include a disinfection chamber, an ozone generator fluidly coupled to the disinfection chamber, a humidifier fluidly coupled to the disinfection chamber and the ozone generator, the humidifier being upstream of the disinfection chamber, and a controller configured to control operation of the ozone generator and the humidifier according to a disinfection cycle.

In some instances, the disinfection cycle may include a first period, a second period, and a third period, wherein during the first period the controller causes the both the ozone generator and the humidifier to operate concurrently. In some instances, the humidifier may be disabled during the second period. In some instances, during the second period, the controller may selectively enable and disable the ozone generator, causing the ozone generator to generate ozone pulses. In some instances, the humidifier and the ozone generator may be disabled during the third period. In some instances, to generate the ozone pulses, the controller may alternate between enabling the ozone generator for about 10 seconds and disabling the ozone generator for about 65 seconds. In some instances, the controller may be configured to cause the ozone generator to generate the ozone pulses at a pulse rate, wherein the pulse rate is configured such that a quantity of ozone within the disinfection chamber is in a range of about 80 parts-per-million (ppm) to about 150 ppm. In some instances, the first period may be about 6 minutes, the second period may be about 72 minutes, and the third period may be about 12 minutes. In some instances, during the first period, the controller may operate the humidifier such that a relative humidity within the disinfection chamber is in a range of about 65% to about 99%. In some instances, the first period may occur before the second period and the second period may occur before the third period. In some instances, the second period may be longer than both the third period and the first period. In some instances, the first period may be shorter than the third period.

Another example of a disinfection device, consistent with the present disclosure, may include a disinfection chamber, an ozone generator fluidly coupled to the disinfection chamber, a pump fluidly coupled to the ozone generator and upstream of the ozone generator, a fan fluidly coupled to the ozone generator and downstream of the ozone generator, a humidifier fluidly coupled to the disinfection chamber and the ozone generator, the humidifier being upstream of the disinfection chamber, and a controller configured to control operation of the ozone generator, the humidifier, the pump, and the fan according to a disinfection cycle, the disinfection cycle including a first period, a second period, and a third period.

In some instances, the controller may cause the fan to operate at a fan flow rate and the pump to operate at a pump flow rate, the pump flow rate being different from the fan flow rate during at least one of the first period, the second period, and/or the third period. In some instances, the fan flow rate may be less than the pump flow rate during the first period and the second period. In some instances, a ratio of the fan flow rate to the pump flow rate during the first period and the second period may be about 0.9. In some instances, the fan flow rate may be greater than or equal to the pump flow rate during the third period. In some instances, the pump flow rate may be in a range of about 1 standard liter per minute (SLPM) to about 1.6 SLPM during the first period and the second period. In some instances, the fan flow rate may be about 0.1 SLPM to about 0.15 SLPM less than the pump flow rate during the first period and the second period. In some instances, during the first period the controller may cause the both the ozone generator and the humidifier to operate concurrently. In some instances, the humidifier may be disabled during the second period. In some instances, during the second period, the controller may selectively enable and disable the ozone generator, causing the ozone generator to generate ozone pulses. In some instances, the humidifier and the ozone generator may be disabled during the third period. In some instances, to generate the ozone pulses, the controller may alternate between enabling the ozone generator for about 10 seconds and disabling the ozone generator for about 65 seconds. In some instances, the controller may be configured to cause the ozone generator to generate the ozone pulses at a pulse rate, wherein the pulse rate is configured such that a quantity of ozone within the disinfection chamber is in a range of about 80 parts-per-million (ppm) to about 150 ppm. In some instances, the first period may be about 6 minutes, the second period may be about 72 minutes, and the third period may be about 12 minutes. In some instances, during the first period, the controller may operate the humidifier such that a relative humidity within the disinfection chamber is in a range of about 65% to about 99%. In some instances, the first period may occur before the second period and the second period may occur before the third period. In some instances, the second period may be longer than both the third period and the first period. In some instances, the first period may be shorter than the third period.

Another example of a disinfection device, consistent with the present disclosure, may include a disinfection chamber, an ozone generator, and a humidifier being configured to be fluidly coupled to the disinfection chamber via a continuous positive air pressure (CPAP) hose and configured to be fluidly coupled to the ozone generator, the humidifier including a humidification chamber and a liquid reservoir, the humidifier being configured to encourage a mixing of generated ozone with generated humidity.

In some instances, the humidification chamber may include a bottom wall, a top wall, and one or more sidewalls extending between the bottom wall and the top wall. In some instances, at least a portion of the top wall may be sloped to direct liquid condensed thereon in a direction of at least one of the one or more sidewalls such that the liquid flows down the at least one of the one or more sidewalls to collect on the bottom wall. In some instances, liquid collected on the bottom wall may be returned to the liquid reservoir. In some instances, the humidifier further may include a liquid disperser coupled to the bottom wall and configured to emit droplets along an emission axis that extends in a direction of the top wall. In some instances, the liquid disperser may be configured to generate droplets having a droplet size in a range of about 1.5 microns to about 4.5 microns. In some instances, the liquid disperser may be configured to generate droplets having a droplet size of about 2.5 microns. In some instances, the liquid disperser may include a protective coating. In some instances, the humidification chamber may include an inlet connector configured to introduce a turbulent flow to air passing therethrough and an outlet downstream of the inlet connector. In some instances, air may exit the inlet connector along an injection axis and the humidifier further includes a liquid disperser having an emission axis, the emission axis extending transverse to the injection axis. In some instances, the emission axis may be substantially perpendicular to the injection axis. In some instances, the humidifier may further include a wick assembly removably coupled to the liquid reservoir and a liquid disperser configured to engage the wick assembly. In some instances, the humidifier may further include a liquid reservoir access that includes a carriage for receiving the liquid reservoir, the carriage being configured to move along an insertion axis and a coupling axis, the coupling axis extending transverse to the insertion axis. In some instances, movement of the carriage along the coupling axis may move the wick assembly into and out of engagement with the liquid disperser.

Another example of a humidifier for use with a disinfection device, consistent with the present disclosure, may include a liquid disperser, a liquid reservoir, and a humidification chamber, the liquid disperser configured to emit liquid from the liquid reservoir into the humidification chamber, the humidification chamber having a bottom wall, a top wall, and one or more sidewalls extending between the bottom wall and the top wall, at least a portion of the top wall is sloped to direct liquid condensed thereon in a direction of at least one of the one or more sidewalls such that the liquid flows down the at least one of the one or more sidewalls to collect on the bottom wall.

In some instances, liquid collected on the bottom wall may be returned to the liquid reservoir. In some instances, the liquid disperser may be coupled to the bottom wall of the humidification chamber. In some instances, the liquid disperser may be configured to emit droplets along an emission axis that extends in a direction of the top wall. In some instances, the humidification chamber may include an inlet connector configured to introduce a turbulent flow to air passing therethrough and an outlet downstream of the inlet connector. In some instances, air may exit the inlet connector along an injection axis, the injection axis extending transverse to the emission axis. In some instances, the emission axis may be substantially perpendicular to the injection axis. In some instances, the liquid disperser may be configured to generate droplets having a droplet size in a range of about 1.5 microns to about 4.5 microns. In some instances, the liquid disperser may be configured to generate droplets having a droplet size of about 2.5 microns. In some instances, the liquid disperser may be a piezo-electric atomizer.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the claims.

What is claimed is:

1. A disinfection device comprising:

a housing;

a disinfection chamber supported by the housing;

an ozone generator configured to generate ozonated air;

a humidifier supported by the housing configured to generate humidity and configured to be fluidly coupled to the disinfection chamber and the ozone generator, the humidifier being configured to encourage a mixing of the generated ozonated air with the generated humidity to generate humidified ozonated air, the humidifier including:
  a humidification chamber, the humidification chamber including a chamber ozone inlet through which the ozonated air enters the humidification chamber and a chamber outlet through which the humidified ozonated air exits the humidification chamber;
  a liquid reservoir configured to receive water; and
  a liquid disperser configured to disperse water from the liquid reservoir directly into the humidification chamber to mix with the ozonated air and generate the humidified ozonated air; and
a controller configured to control operation of the ozone generator and the humidifier according to a disinfection cycle.

2. The disinfection device of claim 1, wherein the disinfection cycle includes an initialization period, an operation period, and a purge period, wherein, during the initialization period, the controller causes both the ozone generator and the humidifier to operate concurrently.

3. The disinfection device of claim 2, wherein the humidifier is disabled during the operation period.

4. The disinfection device of claim 3, wherein, during the operation period, the controller selectively enables and disables the ozone generator, causing the ozone generator to generate ozone pulses.

5. The disinfection device of claim 4, wherein the humidifier and the ozone generator are disabled during the purge period.

6. The disinfection device of claim 4, wherein, to generate the ozone pulses, the controller alternates between enabling the ozone generator for about 10 seconds and disabling the ozone generator for about 65 seconds.

7. The disinfection device of claim 4, wherein the controller is configured to cause the ozone generator to generate the ozone pulses at a pulse rate, wherein the pulse rate is configured such that a quantity of ozone within the disinfection chamber is in a range of about 80 parts-per-million (ppm) to 150 ppm during at least a portion of the disinfection cycle.

8. The disinfection device of claim 2, wherein the initialization period is about 6 minutes, the operation period is about 72 minutes, and the purge period is in a range of about 1 minute to about 20 minutes.

9. The disinfection device of claim 2, wherein, during the initialization period, the controller operates the humidifier such that a relative humidity within the disinfection chamber is in a range of about 65% to about 99%.

10. The disinfection device of claim 2, wherein the initialization period occurs before the operation period and the operation period occurs before the purge period.

11. The disinfection device of claim 10, wherein the operation period is longer than both the purge period and the initialization period.

12. The disinfection device of claim 11, wherein the initialization period is shorter than the purge period.

13. A disinfection device comprising:
  a housing;
  a disinfection chamber supported by the housing and configured to receive a continuous positive air pressure (CPAP) mask, the disinfection chamber including a hose passthrough configured such that a CPAP hose can pass therethrough;
  an ozone generator configured to generate ozonated air;
  a humidifier supported by the housing and configured to generate humidity and configured to be fluidly coupled to the disinfection chamber and the ozone generator, the humidifier being configured to encourage a mixing of the generated ozonated air with the generated humidity to generate humidified ozonated air the humidifier including:
    a humidification chamber, the humidification chamber including a chamber ozone inlet through which the ozonated air enters the humidification chamber and a chamber outlet through which the humidified ozonated air exits the humidification chamber, the chamber outlet being configured to be selectively fluidly coupled to the disinfection chamber through the CPAP hose;
    a liquid reservoir configured to receive water; and
    a liquid disperser configured to disperse water from the liquid reservoir into the humidification chamber to mix with the ozonated air and generate the humidified ozonated air, wherein ozone becomes entrained within the dispersed water;
  a pump fluidly coupled to the disinfection chamber at a location upstream of the disinfection chamber;
  a fan fluidly coupled to the disinfection chamber at a location downstream of the disinfection chamber, wherein, for at least a portion of a disinfection cycle, the fan is operated at a fan flow rate and the pump is operated at a pump flow rate, the fan flow rate being less than the pump flow rate; and
  a controller configured to control operation of the ozone generator, the humidifier, the pump, and the fan according to the disinfection cycle, the disinfection cycle including an initialization period, an operation period, and a purge period.

14. The disinfection device of claim 13, wherein the pump flow rate is different from the fan flow rate during at least one of the initialization period, the operation period, and/or the purge period.

15. The disinfection device of claim 13, wherein the fan flow rate is less than the pump flow rate during the initialization period and the operation period.

16. The disinfection device of claim 15, wherein a ratio of the fan flow rate to the pump flow rate during the initialization period and the operation period is about 0.9.

17. The disinfection device of claim 15, wherein the fan flow rate is equal to or greater than the pump flow rate during the purge period.

18. The disinfection device of claim 15, wherein the pump flow rate is in a range of about 1 standard liter per minute (SLPM) to about 1.6 SLPM during the initialization period and the operation period.

19. The disinfection device of claim 18, wherein the fan flow rate is about 0.1 SLPM to about 0.15 SLPM less than the pump flow rate during the initialization period and the operation period.

20. The disinfection device of claim 13, wherein during the initialization period the controller causes both the ozone generator and the humidifier to operate concurrently.

21. The disinfection device of claim 20, wherein the humidifier is disabled during the operation period.

22. The disinfection device of claim 21, wherein, during the operation period, the controller selectively enables and disables the ozone generator, causing the ozone generator to generate ozone pulses.

23. The disinfection device of claim 22, wherein the humidifier and the ozone generator are disabled during the purge period.

24. The disinfection device of claim 22, wherein, to generate the ozone pulses, the controller alternates between enabling the ozone generator for about 10 seconds and disabling the ozone generator for about 65 seconds.

25. The disinfection device of claim 22, wherein the controller is configured to cause the ozone generator to generate the ozone pulses at a pulse rate, wherein the pulse rate is configured such that a quantity of ozone within the disinfection chamber is in a range of about 80 parts-per-million (ppm) to 150 ppm during at least a portion of the disinfection cycle.

26. The disinfection device of claim 13, wherein the initialization period is about 6 minutes, the operation period is about 72 minutes, and the purge period is in a range of about 1 minute to about 20 minutes.

27. The disinfection device of claim 13, wherein, during the initialization period, the controller operates the humidifier such that a relative humidity within the disinfection chamber is in a range of about 65% to about 99%.

28. The disinfection device of claim 13, wherein the initialization period occurs before the operation period and the operation period occurs before the purge period.

29. The disinfection device of claim 28, wherein the operation period is longer than both the purge period and the initialization period.

30. The disinfection device of claim 29, wherein the initialization period is shorter than the purge period.

* * * * *